Figure 2B:
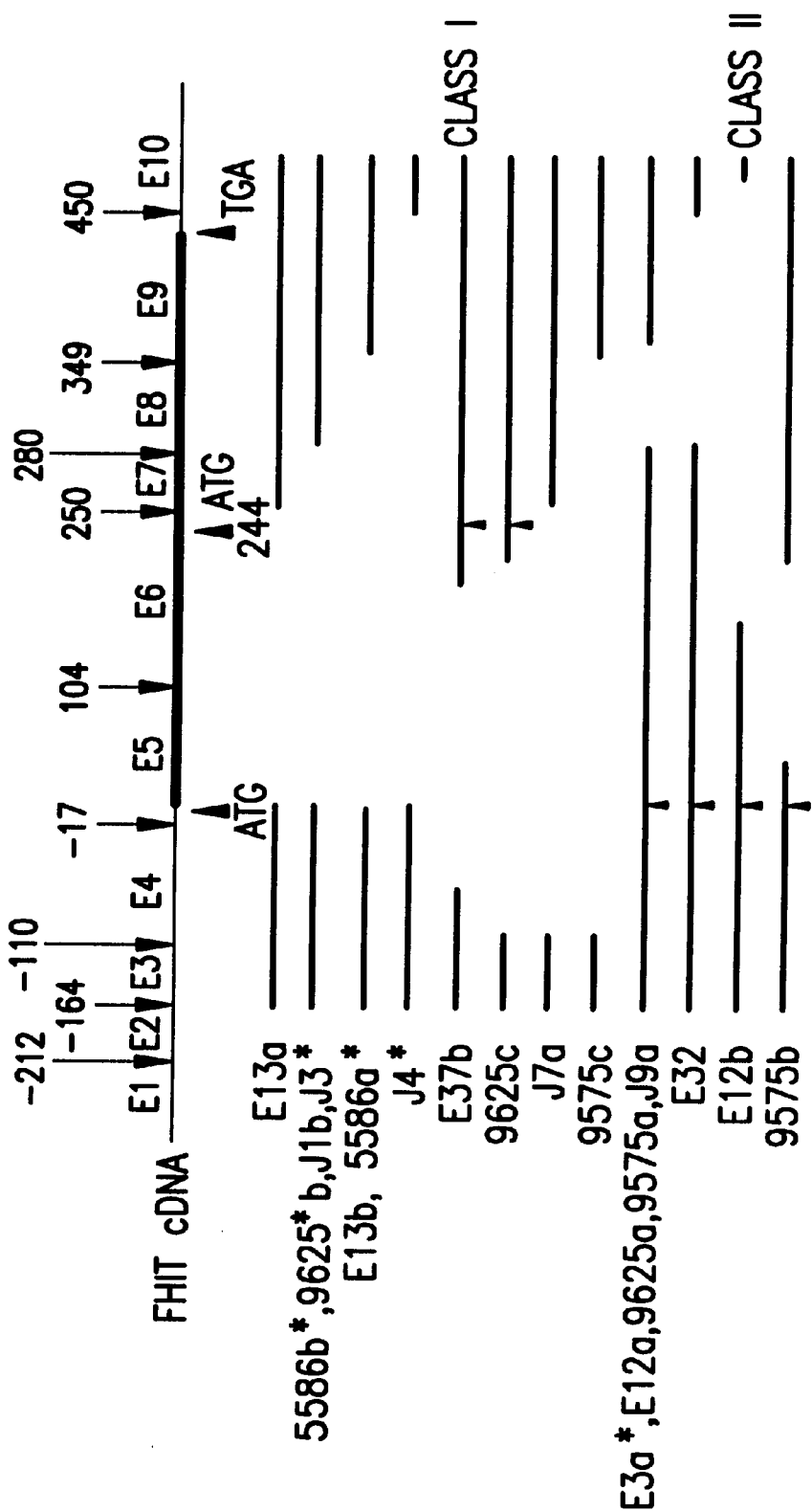

United States Patent [19]
Croce et al.

[11] Patent Number: 5,928,884
[45] Date of Patent: Jul. 27, 1999

[54] FHIT PROTEINS AND NUCLEIC ACIDS AND METHODS BASED THEREON

[76] Inventors: Carlo M. Croce; Frances Kay Huebner, both of 1829 Delancey St., Philadelphia, Pa. 19103

[21] Appl. No.: 08/598,873

[22] Filed: Feb. 9, 1996

[51] Int. Cl.$^6$ .................. G01N 33/574; G01N 33/567; C07H 21/04; C12P 21/08
[52] U.S. Cl. .................. 435/7.23; 435/7.1; 436/503; 436/507; 436/547; 530/387.7; 530/387.9; 536/23.1; 536/23.5; 536/24.33
[58] Field of Search .................. 435/7.1, 7.23; 436/503, 507, 547; 536/23.1, 23.5, 24.33; 530/387.7, 387.9

[56] References Cited

PUBLICATIONS

Hadaczek et al., 1996, Virchows Arch. 429:37–42.
Aburatani et al., 1995, Cytogenet. Cell Genet. 68:137–138.
Bardenheuer et al., 1994, Genomics 19:291–297.
Barsky et al., 1994, Mod. Pathol. 7:633–640.
Baxi et al., 1994, Biochem. 33:14601–14607.
Boldog, 1993, Proc. Natl. Acad. Sci. USA 90:8509–8513.
Boldog et al., 1994, Genes, Chrom. & Cancer 11:216–221.
Brauch et al., 1987, N. Eng. J. Med. 317:1109–1113.
Bullrich et al., 1995, Cytogenet. Cell Genet. 70:250–254.
Chiba et al., 1990, Oncogene 5:1603–1610.
Chung et al., 1993, Nature Genet. 5:254–258.
Cohen et al., 1979, N. Eng. J. Med. 301:592–595.
Daly et al., 1991, Genomics 9:113–119.
Daly et al., 1993, Oncogene 8:1721–1729.
Druck et al., 1995, Cancer Res. 55:5348–5353.
Ebina et al., 1994, Cancer Res. 54:2496–2503.
Fong et al., 1978, J. Natl. Canc. Inst. 61:145–150.
Fu et al., 1991, Cell 67:1047–1058.
Glover et al., 1988, Cancer Genet. Cytogenet. 31:69–73.
Gemmill et al., 1995, Cytogenet. Cell Genet. 68:137.
Gnarra et al., 1994, Nature Genet. 7:85–90.
Graphodatsky et al., 1995, Cytogenet. Cell Genet. 68:142.
Hahn et al., 1996, Science 271:350–353.
Harbour et al., 1988, Science 241:353–357.
Hibi et al., 1992, Oncogene 7:445–449.
Horio et al., 1993, Cancer Res. 53:1–4.
Huang et al., 1995, Biochem. J. 312:925–932.
Hung et al., 1995, JAMA 273:558–563.
International Union Against Cancer, 1989, "TNM classification of malignant tumors," 3rd ed., Geneva: World Health Organization, table of contents.
Jones et al., 1994, Hum. Mol. Genet. 3:2123–2130.
Jones et al., 1995, Nature 376:145–149.
Kastury et al., 1996, Genomics 32:225–235.
Kastury et al., 1996, Cancer Res. 56:978–983.
Killary et al., 1992, Proc. Natl. Acad. Sci. USA 89:10877–10881.
Kim et al., 1993, Am. J. Pathol. 142:307–317.
Kok et al., 1987, Nature 330:578–581.
Kok et al., 1993, Proc. Natl. Acad. Sci. USA 90:6071–6075.
Kok et al., 1994, Cancer Res. 54:4183–4187.
Kok et al., 1995, Cytogenet. Cell Genet. 68:144.
Knight et al., 1993, Cell 74:127–134.
Kremer et al., 1991, Science 252:1711–1714.
Kuzmin et al., 1995, Cytogenet. Cell Genet. 68:145.
LaForgia et al., 1991, Proc. Natl. Acad. Sci. USA 88:5036–5040.
LaForgia et al., 1993, Cancer Res. 53:3118–3124.
Li et al., 1993, Annals of Internal Med. 118(2):106–111.
Leach et al., 1995, Cytogenet. Cell Genet. 68:140.
Lisitsyn et al., 1993, Science 259:946–951.
Lisitsyn et al., 1995, Proc. Natl. Acad. Sci. USA 92:151–155.
Lo et al., 1994, Int. J. Oncol. 4:1359–1364.
Lubinski et al., 1994, Cancer Res. 54:3710–3713.
Lux et al., 1995, Cytogenet. Cell Genet. 68:142.
Maher, 1995, Cytogenet. Cell Genet. 68:145.
Mahyer, 1995, Cytogenet. Cell Genet. 68:145.
McAlpine et al., 1995, Cytogenet. Cell Genet. 68:146.
Michaelis et al., 1995, Cancer Genet. Cytogenet. 81:1–12.
Mitsudomi et al., 1992, Oncogene 7:171–180.
Mozier et al., 1991, FEBS 279(1):14–18.
Murata et al., 1992, Jpn. J. Hum. Genet. 37:205–213.
Murray et al., 1995, Cytogenet. Cell Genet. 68:140.
Naylor et al., 1987, Nature 329:451–454.
O'Connell et al., 1995, Cytogenet. Cell Genet. 68:137.
Ohta et al., 1995, Int. J. Cancer 65:762–767.
Ohta et al., Feb. 23, 1996, Cell 84(4):587–597.
Paradee et al., 1995, Genomics 27:358–361.
Paradee et al., 1995, Cytogenet. Cell Genet. 68:143.
Pathak et al., 1995, Cancer Genet. Cytogenet. 83:172–173.
Pearson et al., 1990, J. Biol. Chem. 265(8):4583–4591.
Pekarsky et al., 1995, Cytogenet. Cell Genet. 68:144–145.
Rabbitts et al., 1989, Genes Chrom. Cancer 1:95–105.
Rabbitts et al., 1990, Gene Chrom. Cancer 2:231–238.
Rassool et al., 1992, Am. J. Hum. Genet. 50:1243–1251.
Rassool et al., 1995, Cytogenet. Cell Genet. 68:142–143.
Reichel et al., 1994, Mol. Carcinog. 9:105–109.
Roche et al., 1994, Hum. Mol. Genet. 3:215.
Sanchez et al., 1995, Cytogenet. Cell Genet. 68:146.
Schnittger, 1995, Cytogenet Cell Genet. 68:142.
Sekido et al., 1994, Oncogene 9:1599–1604.
Séraphin, 1992, J. DNA Sequencing & Mapping 3:177–179.
Shridhar et al., 1995, Cytogenet. Cell Genet. 68:144.
Smith et al., 1995, Cytogenet. Cell Genet. 68:126–146.
Sozzi et al., 1991, Cancer Res. 51:400–404.
Sundaresan et al., 1992, Oncogene 7:1989–1997.

(List continued on next page.)

*Primary Examiner*—Lila Feisee
*Assistant Examiner*—Geetha P. Bansal
*Attorney, Agent, or Firm*—Pennie & Edmonds LLP

[57] ABSTRACT

The present invention relates to nucleotide sequences of FHIT genes and amino acid sequences of their encoded proteins, as well as derivatives and analogs thereof, and antibodies thereto. The FHIT gene sequence is mutated in diseases involving cell overproliferation, particularly malignancies of the digestive tract. The present invention further relates to the use of FHIT genes and their encoded proteins as diagnostic and therapeutic reagents for the detection and treatment of disease states associated with cell overproliferation.

24 Claims, 16 Drawing Sheets

OTHER PUBLICATIONS

Sutherland, 1991, Genet. Anal. Tech. Appl. 8(6):1616–166.
Takahashi et al., 1989, Science 246:491–494.
Testa et al., 1994, Genes Chrom. Cancer 11:178–194.
Thorne et al., 1995, Biochem. J. 311:717–721.
van den Berg et al., 1995, Cytogenet. Cell Genet. 68:144.
Verkerk et al., 1991, Cell 65:905–914.
Wang and Perkins, 1984, Cancer Genet. Cytogenet. 11:479–481.
Wang et al., 1993, Genomics 17:341–347.
Wary et al., 1993, Cancer Res. 53:1498–1502.
Weinmann–Dorsch et al., 1984, Eur. J. Biochem. 138:179–185.
WhangPeng et al., 1982, Science 215:181–182.
Wilhelm et al., 1995, Cancer Res. 55:5383–5385.
Wilke et al., 1994, Genomics 22:319–326.
Wilke et al., 1995, Cytogenet. Cell Genet. 68:143.
World Health Organization, 1981, "Histological typing of lung tumors," 2nd ed., Geneva:World Health Organization, table of contents.
Xu et al., 1994, J. Natl. Cancer Inst. 86(9):695–699.
Yang, 1980, Cancer Res. 40:2633–2644.
Yang et al., 1987 J. Natl. Cancer Inst. 79(6):1241–1246.
Yokota et al., 1987, Proc. Natl. Acad. Sci. USA 84:9252–9256.
Yokota et al., 1989, Cancer Res. 49:3598–3601.
Yokoyama et al., 1992, Cancer Res. 52:873–877.
Yu et al., 1991, Science 252:1179–1181.
Yunis and Soreng, 1984, Science 226:1199–1204.
Zabarovsky et al., 1995, Cytogenet. Cell Genet. 68:141.
Zahkaryev et al., 1995, Cytogenet. Cell Genet. 68:141.

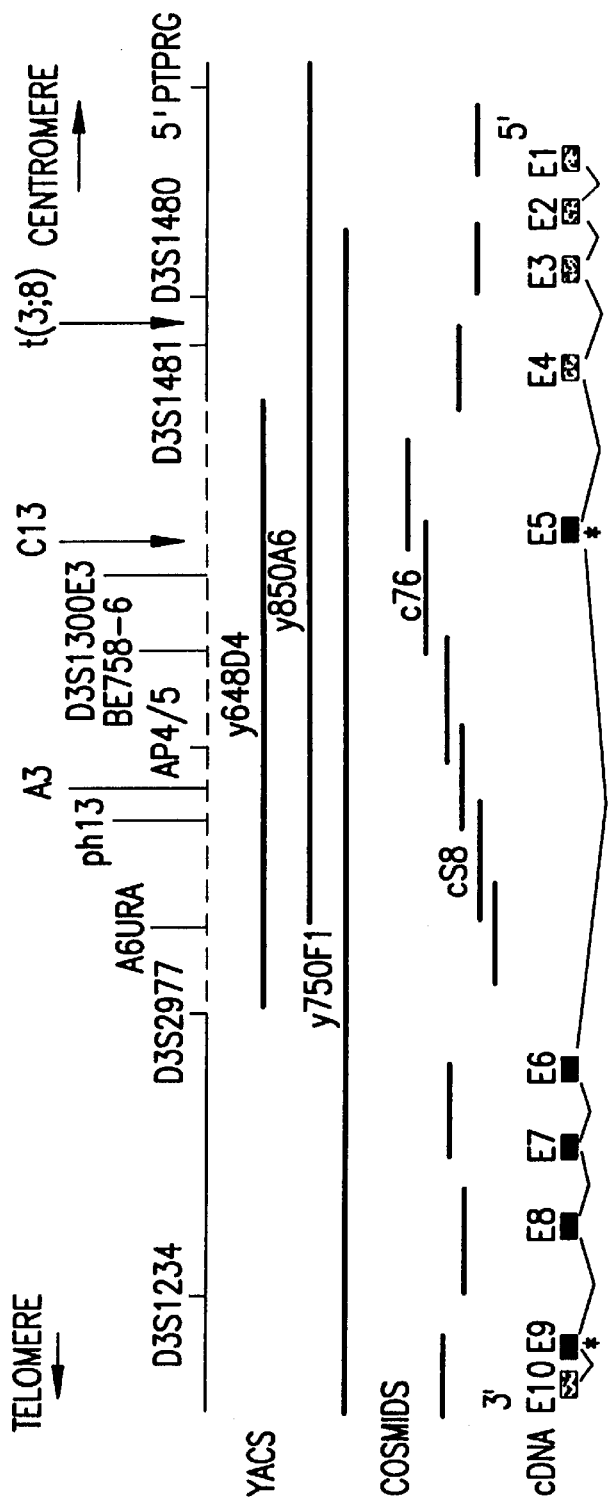
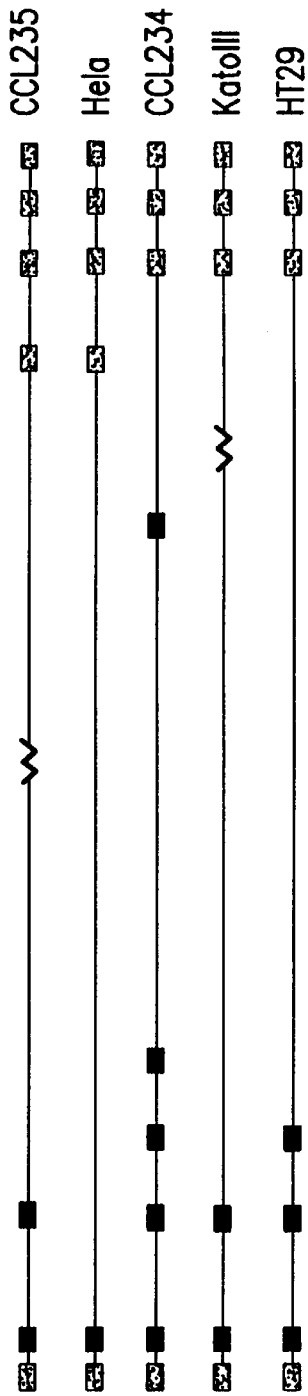
FIG. 1A
FIG. 1B

FIG. 2A

FIG. 4A

```
             1                                                       50
r50713       ..........  ..........  ..........  ..........  ..........
CDNA7F1      TCCCCGCTCT  GCTCTGTCCG  GTCACAGGAC  TTTTTGCCCT  CTGTTCCCGG
r11128       ..........  ..........  ..........  ..........  ..........

51                                                      100
r50713       ..........  ..........  ..........  ..........  ..........
CDNA7F1      GTCCCTCAGG  CGGCCACCCA  GTGGGCACAC  TCCCAGGCGG  CGCTCCGGCC
r11128       ..........  ..........  ..........  ..........  ..........

101                                                     150
r50713       ..........  ..........  ..........  ..........  ..........
CDNA7F1      CCGCGCTCCC  TCCCTCTGCC  TTTCATTCCC  AGCTGTCAAC  ATCCTGGAAG
r11128       ..........  ..........  ..........  ..........  ..........

151                                                     200
r50713       ..........  ..........  ..........  ..........  ..........
CDNA7F1      CTTTGAAGCT  CAGGAAAGAA  GAGAAATCCA  CTGAGAACAG  TCTGTAAAGG
r11128       ..........  ..........  .....ATCCA  CTGAGAACAG  TCTGTAAAGG 201                                                     250
r50713       ..........  ..........  ..........  ..........  ..........
CDNA7F1      TCCGTAGTGC  TATCTACATC  CAGACGGTGG  AAGGGAGAGA  AAGAGAAAGA
r11128       TCCGTAGTGC  TATCTACATC  CAGACGGTGG  AAGGGAGAGA  AAGAGAAAGA 251                                                     300
r50713       ..........  ..........  ..........  ..........  ..........
CDNA7F1      AGGTATCCTA  GGAATACCTG  CCTGCTTAGA  CCCTCTATAA  AAGCTCTGTG
r11128       AGGTATCCTA  GGAATACCTG  CCTGCTTAGA  CCCTCTATAA  AAGCTCTGTG 301                                                     350
r50713       ..........  ..........  ..........  ..........  ..........
CDNA7F1      CATCCTGCCA  CTGAGGACTC  CGAAGAGGTA  GCAGTCTTCT  GAAAGACTTC
r11128       CATCCTGCCA  CTGAGGACTC  CGAAGAGGTA  GCAGTCTTCT  GAAAGACTTC 351                                                     400
r50713       ..........  ..........  ..........  ..........  ..........
CDNA7F1      AACTGTGAGG  ACATGTCGTT  CAGATTTGGC  CAACATCTCA  TCAAGCCCTC
r11128       AACTGTGAGG  ACATGTCGTT  CAGATTTGGC  CAACATCTCA  TCAAGCCCTC 401                                                     450
r50713       ..........  ..........  ..........  ..........  ..........
CDNA7F1      TGTAGTGTTT  CTCAAAACAG  AACTGTCCTT  CGCTCTTGTG  AATAGGAAAC
r11128       TGTAGTGTTT  CTCAAAACAG  AACTGTCCTT  CGCTCTTGTG  AATAGGAAAC 451                                                     500
r50713       ..........  ..........  ..........  ..........  ..........
CDNA7F1      CTGTGGTACC  A.GGACATGT  CCTTGTGTGC  CCGCTGCGGC  CAGT.GGAGC
r11128       CTGTGGTACC  AGGGACATGT  CCTTGTGTGC  CCGCTGCGGC  CAGTGGGAGC 501                                                     550
r50713       ..........  ..........  ..........  ..........  ..........
CDNA7F1      GCTTCCATGA  CCTGCGTCCT  GATGAAGT.G  GCCGATTTGT  TTCAGACGAC
r11128       GCTTCCATGA  CCTGCGTCCT  GATGAAGTGG  GCCGATTTGT  TTCAGACGAC 551                                                     600
r50713       ..........  ..........  ..........  ..........  ..........
```

FIG.7A

```
CDNA7F1   CCAGAGAGT. .CGGGACAGT GGTGGAAAAA CATTTCCATG GGACCTCTCT
r11128    CCAGAGAGTT CGGGACAGTG GTTGGANAAA CATTTTCCTG GGGAC.....

601                                                    650
r50713    .......... .......... ..AAGAAAAC CGGANAGACT TTGAAGCACG
CDNA7F1   CACCTTTTCC ATGCAGGATG GCCCCGAAGC CGGACAGACT GTGAAGCACG
r11128    .......... .......... .......... .......... ..........

651                                                    700
r50713    TTCACGTCCA CGTTNTTCCC GGGAAGGCTG GAAAACTTTC ACAGGAATGA
CDNA7F1   TTCACGTCCA TGTTCTTCCC AGGAAGGCTG G.AGACTTTC ACAGGAATGA
r11128    .......... .......... .......... .......... ..........

701                                                    750
r50713    CAGCATCTAT GAGGAGCTCC CAGAAANATG ACAAGGAGGA CTTTCCTGCC
CDNA7F1   CAGCATCTAT GAGGAGCT.C CAGAAACATG ACAAGGAGGA CTTTCCTGCC
r11128    .......... .......... .......... .......... ..........

751                                                    800
r50713    TCTTGGAGAT CAGAGGAGGA AATGGCAGCA GAAAGCCGCA GCTCTGCGGG
CDNA7F1   TCTTGGAGAT CAGAGGAGGA AATGGCAGCA G.AAGCCGCA GCTCTGCGGG
r11128    .......... .......... .......... .......... ..........

801                                                    850
r50713    TCTACTTTCA GTGACA.... .......CAG ATCCTGAATT CCAGCAAAAG
CDNA7F1   TCTACTTTCA GTGACACAGA TGTTTTTCAG ATCCTGAATT CCAGCAAAAG
r11128    .......... .......... .......... .......... ..........

851                                                    900
r50713    AGCTATTGCC AACCAGTTTG AANACCGCCC CCCCGCCTCT CCCCAAGAGG
CDNA7F1   AGCTATTGCC AACCAGTTTG AAGACCGCCC CCCCGCCTCT CCCCAAGAGG
r11128    .......... .......... .......... .......... ..........

901                                                    950
r50713    AACTGAATCA GCATGAAAAT GCAGTTTCTT CATCTCACCA TCCTGTANTC
CDNA7F1   AACTGAATCA GCATGAAAAT GCAGTTTCTT CATCTCACCA TCCTGTATTC
r11128    .......... .......... .......... .......... ..........

951                                                   1000
r50713    TTCAACCAGT GATCCCCCAC CTCGGTCACT CCAACTCCCT TAAAATACCT
CDNA7F1   TTCAACCAGT GATCCCCCAC CTCGGTCACT CCAACTCCCT TAAAATACCT
r11128    .......... .......... .......... .......... ..........

1001                                                  1050
r50713    AGACCTAAAC GGCTCAGACA GGCAGATTTG AGGTTTCCCC CTGTCTCCTT
CDNA7F1   AGACCTAAAC GGCTCAGACA GGCAGATTTG AGGTTTCCCC CTGTCTCCTT
r11128    .......... .......... .......... .......... ..........
```

FIG.7B

```
         1051                                                    1100
r50713   ATTCGGCAGC CTTATGATTA AACTTCCNNC TCTGCTGC.. ..........
CDNA7F1  ATTCGGCAGC CTTATGATTA AACTTCCTTC TCTGCTGCAA AAAAAAAAAA
r11128   .......... .......... .......... .......... ..........

1101
r50713   ...
CDNA7F1  AAA
r11128   ...
```

FIG.7C

5'3' Frame 1
A AEXE V Stop S Stop G CRIRR Q GETSNLPV Stop AV Stop VF Stop GSWSDRGGGSL
VEXYR Met VR Stop RNCIFMetLIQFLLGRGGGAXFKLVGNSSFAGIQDLCH Stop K
Stop TRRAAFCCHFLL Stop SPRGRKVLLVXFLGAPHRCCHSCESFPAFPGXTWT
Stop TCFKVXPVF 5'3' Frame 2
QQXXKFNHKAAE Stop GDRGKPQICLSEPFRSRYFKGVGVTEVGDHWLKXTGW
Stop DEETAFSC Stop FSSSWGEAGGRXSNWLAIALLEFRICVTESRPAELRLSAAIS
SSDLQEAGKSSLSXFWELLIDAVIPVKVFQPSREXRGRERASKSXRFS 5'3' Frame 3
SRXGSLIIRLPNKETGGNLKSACLSRLGLGILRELE Stop PR WGITG Stop RXQDGE
Met KKLHFHADSVPLGERRGGGXQTGWQ Stop LFCWNSGSVSLKVDPQSCGFLLPF
PPLISKRQESPPCHXSGSSS Stop Met LSFL Stop KFSSLPGXNVDVNVLQSXSGFL 3'5' Frame 1
KKTGXTLKHVHVHVXPGKAGKLSQE Stop QHL Stop GAPR X Met TRRTFLPLGDQRR
KWQQKAAALR VYFQ Stop HRS Stop IPAKELLPTSLXTAPPPLPKRN Stop IS Met K Met Q
FLHLTILXSSTSDPPPRSLQLP Stop NT Stop T AQTGRFEVSPCLLIRQPYD Stop T
SXSA 3'5' Frame 2
RKPXRL Stop STFTSTXFPGRLENFHRNDSIYEELPEX Stop QGGLSCLLEIRGGNGS
RKPQLCGSTFSDTDPEFQQKSYCQPV Stop XPPPRLSPRGTESA Stop KCSFFTSPSCX
LQPVIPHLGHSNSLKIPRPKRLRQADLRFPPVSLFGSLMetIKLXXLL 3'5' Frame 3
ENRXDFEARSRPRXSREGWKTFTG Met TAS Met RSSQKXDKEDFPASWRSEE Met A
AESRSSAGLLSVTQILNSSKRAIANQFEXRPPASPQEELNQHENAVSSSHHPVXFN
Q Stop SPTSVTPTPLKYLDLNGSDRQI Stop GFPLSPYSAAL Stop LNFXLCC

FIG. 8

5'3' Frame 1
IHStopEQSVKVRSAIYIQTVEGRERERRYPRNTCLLRPSIKALCILPLRTPKRStopQ
SSERLQLStopGHVVQIWPTSHQALCSVSQNRTVLRSCEStopETCGTRDMetSLCARC
GQWERFHDLRPDEVGRFVSDDPESSGQWLXKHFPGD

5'3' Frame 2
STENSLStopRSVVLSTSRRWKGEKEKEGILGIPACLDPLStopKLCASCHStopGLRR
GSSLLKDFNCEDMetSFRFGQHLIKPSVVFLKTELSFALVNRKPVVPGTCPCVPAA
ASGSASMetTCVLMetKWADLFQTTQRVRDSGWXNIFLG

5'3' Frame 3
PLRTVCKGPStopCYLHPDGGRERKRKKVSStopEYLPAStopTLYKSSVHPATEDSEE
VAVFStopKTSTVRTCRSDLANISSSPLStopCFSKQNCPSLLStopIGNLWYQGHVLV
CPLRPVGALPStopPASStopSGPICFRRPREFGTVVGXTFSWG

3'5' Frame 1
VPRKMetFXQPLSRTLWVVStopNKSAHFIRTQVMetEALPLAAAGTQGHVPGTTGFL
FTRAKDSSVLRNTTEGLMetRCWPNLNDMetSSQLKSFRRLLPLRSPQWQDAQSFY
RGSKQAGIPRIPSFSFSPFHRLDVDSTTDLYRLFSVD

3'5' Frame 2
SPGKCXSNHCPELSGSSETNRPTSSGRRSWKRSHWPQRAHKDMetSLVPQVSYSQ
ERRTVLFStopETLQRAStopStopDVGQIStopTTCPHSStopSLSEDCYLFGVLSGRMetH
RAFIEGLSRQVFLGYLLSLSLPSTVWMetStopIALRTFTDCSQW

3'5' Frame 3
PQENVXPTTVPNSLGRLKQIGPLHQDAGHGSAPTGRSGHTRTCPWYHRFPIHKSE
GQFCFEKHYRGLDEMetLAKSERHVLTVEVFQKTATSSESSVAGCTELLStopRVStop
AGRYSStopDTFFLFLSLPPSGCRStopHYGPLQTVLSG

FIG.9

```
            1                                                      50
CDNA7F1     ..........  ..........  ..........  ..........  ..........
u32615      GAAACTTGTG  TGCATACGAA  TAATAAAATT  CGATAATATT  GGAATTTTTA 51                                                     100
CDNA7F1     ..........  ..........  ..........  ..........  ..........
u32615      GTCCGCTTTA  TCTGTTCCAT  GATACTGTTA  CTTACATATA  TGCAAGACGC 101                                                    150
CDNA7F1     ..........  ..........  ..........  ..........  ..........
u32615      TATTTTCTCA  TAGTCTGTTT  GTTTTTTAAG  TATATCAATC  TTTCTTATTA 151                                                    200
CDNA7F1     ..........  .....TCCCC  GCTCTGCTCT  GTCCGGTCAC  AGGACTTTTT
u32615      TATTCCATAG  ACACTTTCGC  ACATGACTCT  CCAGGGACTC  CGCGATATGG 201                                                    250
CDNA7F1     GCCCTCTGTT  CCCGGGTCCC  TCAGGCGGCC  ACCCAGTGGG  CACACTCCCA
u32615      GTTGTGAGCA  TCGTGAAGCT  GAATTCAACC  AACAACTTAG  ATTCTTACAA 251                                                    300
CDNA7F1     GGCGGCGCTC  CGGCCCCGCG  CTCCCTCCCT  CTGCCTTTCA  TTCCCAGCTG
u32615      ......TATT  CGTAAGCCAG  AATGCCAAAA  CAGCTATATT  TCTCCAAGTT 301                                                    350
CDNA7F1     TCAACATCCT  GG..AAGCTT  TGAAGCTCAG  GAAAGAAGAG  AAATCCACTG
u32615      TCCTGTTGGA  AGTCAAGTTT  TTTATCGTAC  TAAGGTAAGT  TAACGGTCTC 351                                                    400
CDNA7F1     AGAACAGTCT  GTAAAGGTCC  GT......AG  TGCTATCTAC  ATCCAGACGG
u32615      ATGTGTGTAG  ATATTGGTGT  TTGCAAACTT  TTGTTTGTCA  TTCTTATTTA 401                                                    450
CDNA7F1     TGGAAGGGAG  AGAAAGAGAA  AGAAGGTATC  CTAGGAATAC  CTGCCTGCTT
u32615      TTCTATAACG  GCAGACAGTT  TGTGATTTTT  CTTTGGTTGA  GGTCAGCTGC 451                                                    500
CDNA7F1     AGACCCTCTA  TAAAAGCTCT  GTGCATCCTG  CCACTGAGGA  CTCCGAAGAG
u32615      TAACGATTTT  AGTTATCTGC  CGCGTTTGTA  AACCTGAAAC  CAATTTTACC 501                                                    550
CDNA7F1     GTAGCAGTCT  TCTGAAAGAC  TTCAACTGTG  AGGACATGTC  GTTCAGATTT
u32615      AGGTCATGTT  TTGGTAATTC  CGCAACGGGC  GGTCCCTAGA  TTGAAAGATT 551                                                    600
CDNA7F1     GGCCAACATC  TCATCAAGCC  CTCTGTAGTG  TTTCTCAAAA  CAGAACTGTC
u32615      TGACACCTTC  AGAGGTAGGA  TTCTTATGCT  ATTCGAAAAA  ATAATGGAAT 601                                                    650
CDNA7F1     CTTCGCTCTT  GTGAATAGGA  AACCTGTGGT  ACCAGGACAT  GTCCTTGTGT
u32615      CTGCATACGC  TAACTAATGA  AAACTTAGTT  GACGGATTTG  TTTACTTCTG 651                                                    700
CDNA7F1     GCCCGCTGCG  GCCAGTGGAG  CGCTTCCATG  ACCTGCGTCC  TGATGAAGTG
u32615      TTCGCAAAGT  GCAACAGGTA  ATCGAAAAGG  TGTTTTCGGC  ATCTGCATCA

701                   FIG.10A                          750
```

```
CDNA7F1   GCCGATTTGT TTCA...GAC GACCCAGAGA GTCGGGACAG TGGTGGAAAA
u32615    AACATTGGTA TTCAAGTAAG TACTTTGATA GTCAAGGAAT AAATAAAAAA 751                                                  800
CDNA7F1   AC........ .......... .......... ..........A TTTCCATGGG
u32615    ACATATTCCT TTTCACATTC AAAATAAAAA ATCGTTTTAA TTTAGAAGCT 801                                                  850
CDNA7F1   ACCTCTCTCA CCTTTTCCAT GCAGGATGGC CCCGAAGCCG ACAGACTGT
u32615    GACATTTTGC TTTTAACTCA ATAGGATGGT GTAGACGCTG GTCAAACAGT 851                                                  900
CDNA7F1   GAAGCACGTT CACGTCCATG TTCTTCCCAG GAAGGCTGGA GACTTTCACA
u32615    TCCTCATGTA CATGTTCACA TTATCCCTCG TAAAAAGGCA GATTTTTCAG 901                                                  950
CDNA7F1   GGAATGACAG CATCTATGAG GAGCTCCAGA AACATGACAA GGAGGACTTT
u32615    AAAACGATCT AGTCTACAGT GAGTTGGAAA AAAACG..AA GGAAATCTTG 951                                                 1000
CDNA7F1   CCTGCCTCTT GGAGATCAGA GGAGGAAATG GCAGCAGAAG CCGCAGCTCT
u32615    CTTCCCTTT. ....ATCTTA CGGGAAATGA GCGGTATGCA GGAGATGAGA 1001                                                1050
CDNA7F1   GCGGGTCTAC TTTCAGTGAC ACAGATGTTT TCAGATCCT GAATTCCAGC
u32615    GACCGCCAAC CAGTATGAGG CAAGCTATTC CTAAGGACGA GGATCGTAAG 1051                                                1100
CDNA7F1   AAAAGAGCTA TTGCCAACCA GTTTGAAGAC CGCC...... ...CCCCCGC
u32615    CCAAGAACAC TTGAGGAAAT GGAAAAGGAA GCTCAGTGGT TGAAAGGGTA 1101                                                1150
CDNA7F1   CTCTCCCCAA GAGGAACTGA ATCAGCATGA AAATGCAGTT TCTTCATCTC
u32615    CTTTTCCGAA GAGCAAGAGA AGGAATAAAA AGTTGAAGTA CCTCAATACC 1151                                                1200
CDNA7F1   ACCATCCT.G TATTCTTCAA CCAGTGATCC CCCACCTCGG TCACTCCAAC
u32615    ACAGGGGTAG TGTTTACGTA TGAATTAAGC TAAATATTAT ATGACCCTTT 1201                                                1250
CDNA7F1   TCCCTTAAAA TACCTAGACC TAAACGGCTC AGACAGGCAG ATTTGAGGTT
u32615    TTTTTTATTT CACCCAAGGT TACAAG..AA AAATTTCCTT TTTTCTCTCT 1251                                                1300
CDNA7F1   TCCCCCTGTC TCCTTATTCG GCAGCCTTAT GATTAAACTT CCTTCTCTGC
u32615    ACCCTGCTTA CATTGCATCT GTCTGCTGAG CTTTAGCAAC ACAACGTAAC 1301                                                1350
CDNA7F1   TGCAAAAAAA AAAAAAA.. .......... .......... ..........
u32615    CATACATATT GTGATGAACC CTTCTACAAT TCGATCGAAT TAGCTTCAGT 1351                                                1400
CDNA7F1   .......... .......... .......... .......... ..........
u32615    TCCCTATTTT GATTTGCTC TCTTTCTTTC ATCCTTTCCT CATAACCCTA 1401        1424
CDNA7F1   .......... .......... ....
```

FIG.10B u32615  CTAGATATCC ATCTTTTTGA ATTC

FIG.10C

431 CGCTCTTGTGAATAGGAAACCTGTGGTACCAGGACATGTCCTTGTGTGCC 480
    ||| |||| ||   ||||||  | |||||||| |||||  | ||     |
465 CGCGTTTGTAAACCTGAAACCAATTTTACCAGGTCATGTTTTGGTAATTC 514

481 CGCTGCGGCCAGT 493
    |||  ||| | ||
515 CGCAACGGGCGGT 527

FIG.10D

SEQUENCE LISTING (1) GENERAL INFORMATION:

(iii) NUMBER OF SEQUENCES: 77

(2) INFORMATION FOR SEQ ID NO:1:

(i) SEQUENCE CHARACTERISTICS:
      (A) LENGTH: 1095 base pairs
      (B) TYPE: nucleic acid
      (C) STRANDEDNESS: single
      (D) TOPOLOGY: unknown (ii) MOLECULE TYPE: DNA (ix) FEATURE:
      (A) NAME/KEY: CDS
      (B) LOCATION: 363..803

(xi) SEQUENCE DESCRIPTION: SEQ ID NO:1:

```
TCCCCGCTCT GCTCTGTCCG GTCACAGGAC TTTTTGCCCT CTGTTCCCGG GTCCCTCAGG        60

CGGCCACCCA GTGGGCACAC TCCCAGGCGG CGCTCCGGCC CCGCGCTCCC TCCCTCTGCC       120

TTTCATTCCC AGCTGTCAAC ATCCTGGAAG CTTTGAAGCT CAGGAAAGAA GAGAAATCCA       180

CTGAGAACAG TCTGTAAAGG TCCGTAGTGC TATCTACATC CAGACGGTGG AAGGGAGAGA       240

AAGAGAAAGA AGGTATCCTA GGAATACCTG CCTGCTTAGA CCCTCTATAA AAGCTCTGTG       300

CATCCTGCCA CTGAGGACTC CGAAGAGGTA GCAGTCTTCT GAAAGACTTC AACTGTGAGG       360

AC ATG TCG TTC AGA TTT GGC CAA CAT CTC ATC AAG CCC TCT GTA GTG         407
   Met Ser Phe Arg Phe Gly Gln His Leu Ile Lys Pro Ser Val Val
    1               5                  10                  15

TTT CTC AAA ACA GAA CTG TCC TTC GCT CTT GTG AAT AGG AAA CCT GTG         455
Phe Leu Lys Thr Glu Leu Ser Phe Ala Leu Val Asn Arg Lys Pro Val
                20                  25                  30

GTA CCA GGA CAT GTC CTT GTG TGC CCG CTG CGG CCA GTG GAG CGC TTC         503
Val Pro Gly His Val Leu Val Cys Pro Leu Arg Pro Val Glu Arg Phe
            35                  40                  45

CAT GAC CTG CGT CCT GAT GAA GTG GCC GAT TTG TTT CAG ACG ACC CAG         551
His Asp Leu Arg Pro Asp Glu Val Ala Asp Leu Phe Gln Thr Thr Gln
        50                  55                  60

AGA GTC GGG ACA GTG GTG GAA AAA CAT TTC CAT GGG ACC TCT CTC ACC         599
Arg Val Gly Thr Val Val Glu Lys His Phe His Gly Thr Ser Leu Thr
    65                  70                  75

TTT TCC ATG CAG GAT GGC CCC GAA GCC GGA CAG ACT GTG AAG CAC GTT         647
Phe Ser Met Gln Asp Gly Pro Glu Ala Gly Gln Thr Val Lys His Val
80                  85                  90                  95

CAC GTC CAT GTT CTT CCC AGG AAG GCT GGA GAC TTT CAC AGG AAT GAC         695
His Val His Val Leu Pro Arg Lys Ala Gly Asp Phe His Arg Asn Asp
```

```
              100               105               110
AGC ATC TAT GAG GAG CTC CAG AAA CAT GAC AAG GAG GAC TTT CCT GCC    743
Ser Ile Tyr Glu Glu Leu Gln Lys His Asp Lys Glu Asp Phe Pro Ala
            115                 120                 125

TCT TGG AGA TCA GAG GAG GAA ATG GCA GCA GAA GCC GCA GCT CTG CGG    791
Ser Trp Arg Ser Glu Glu Glu Met Ala Ala Glu Ala Ala Ala Leu Arg
        130                 135                 140

GTC TAC TTT CAG TGACACAGAT GTTTTTCAGA TCCTGAATTC CAGCAAAAGA        843
Val Tyr Phe Gln
        145

GCTATTGCCA ACCAGTTTGA AGACCGCCCC CCCGCCTCTC CCCAAGAGGA ACTGAATCAG  903

CATGAAAATG CAGTTTCTTC ATCTCACCAT CCTGTATTCT TCAACCAGTG ATCCCCCACC  963

TCGGTCACTC CAACTCCCTT AAAATACCTA GACCTAAACG GCTCAGACAG GCAGATTTGA  1023

GGTTTCCCCC TGTCTCCTTA TTCGGCAGCC TTATGATTAA ACTTCCTTCT CTGCTGCAAA  1083

AAAAAAAAAA AA                                                     1095
```

(2) INFORMATION FOR SEQ ID NO:2:

(i) SEQUENCE CHARACTERISTICS:
       (A) LENGTH: 147 amino acids
       (B) TYPE: amino acid
       (D) TOPOLOGY: unknown (ii) MOLECULE TYPE: protein (xi) SEQUENCE DESCRIPTION: SEQ ID NO:2:

```
Met Ser Phe Arg Phe Gly Gln His Leu Ile Lys Pro Ser Val Val Phe
 1               5                  10                  15

Leu Lys Thr Glu Leu Ser Phe Ala Leu Val Asn Arg Lys Pro Val Val
                20                  25                  30

Pro Gly His Val Leu Val Cys Pro Leu Arg Pro Val Glu Arg Phe His
            35                  40                  45

Asp Leu Arg Pro Asp Glu Val Ala Asp Leu Phe Gln Thr Thr Gln Arg
        50                  55                  60

Val Gly Thr Val Val Glu Lys His Phe His Gly Thr Ser Leu Thr Phe
65                  70                  75                  80

Ser Met Gln Asp Gly Pro Glu Ala Gly Gln Thr Val Lys His Val His
                85                  90                  95

Val His Val Leu Pro Arg Lys Ala Gly Asp Phe His Arg Asn Asp Ser
            100                 105                 110

Ile Tyr Glu Glu Leu Gln Lys His Asp Lys Glu Asp Phe Pro Ala Ser
        115                 120                 125

Trp Arg Ser Glu Glu Glu Met Ala Ala Glu Ala Ala Ala Leu Arg Val
    130                 135                 140

Tyr Phe Gln
145
```

(2) INFORMATION FOR SEQ ID NO:3:

(i) SEQUENCE CHARACTERISTICS:
       (A) LENGTH: 168 amino acids
       (B) TYPE: amino acid
       (D) TOPOLOGY: unknown (ii) MOLECULE TYPE: protein (xi) SEQUENCE DESCRIPTION: SEQ ID NO:3:

```
Met Pro Lys Gln Leu Tyr Phe Ser Lys Phe Pro Val Gly Ser Gln Val
 1               5                  10                  15
```

```
Phe Tyr Arg Thr Lys Leu Ser Ala Ala Phe Val Asn Leu Lys Pro Ile
                20                  25                  30

Leu Pro Gly His Val Leu Val Ile Pro Gln Arg Ala Val Pro Arg Leu
            35                  40                  45

Lys Asp Leu Thr Pro Ser Glu Leu Thr Asp Leu Phe Thr Ser Val Arg
 50                  55                  60

Lys Val Gln Ser Ala Ser Ala Ser Asn Ile Gly Ile Gln Asp Gly Val
 65                  70                  75                  80

Asp Ala Gly Gln Thr Val Pro His Val His Val His Ile Ile Pro Arg
                85                  90                  95

Lys Lys Ala Asp Phe Ser Glu Asn Asp Leu Val Tyr Ser Glu Leu Glu
                100                 105                 110

Lys Asn Glu Gly Asn Leu Ala Ser Leu Tyr Leu Thr Gly Asn Glu Arg
                115                 120                 125

Tyr Ala Gly Asp Glu Arg Pro Pro Thr Ser Met Arg Gln Ala Ile Pro
                130                 135                 140

Arg Thr Leu Glu Glu Met Glu Lys Glu Ala Gln Trp Leu Lys Gly Tyr
145                 150                 155                 160

Phe Ser Glu Glu Gln Glu Lys Glu
                165

(2) INFORMATION FOR SEQ ID NO:4:

(i) SEQUENCE CHARACTERISTICS:
        (A) LENGTH: 203 amino acids
        (B) TYPE: amino acid
        (D) TOPOLOGY: unknown (ii) MOLECULE TYPE: protein (xi) SEQUENCE DESCRIPTION: SEQ ID NO:4:

Met Ile Leu Ser Lys Thr Lys Lys Pro Lys Ser Met Asn Lys Pro Ile
 1               5                  10                  15

Tyr Phe Ser Lys Phe Leu Val Thr Glu Gln Val Phe Tyr Lys Ser Lys
                20                  25                  30

Tyr Thr Tyr Ala Leu Val Asn Leu Lys Pro Ile Val Pro Gly His Val
                35                  40                  45

Leu Ile Val Pro Leu Arg Thr Thr Val Leu Asn Leu Ser Asp Leu Thr
 50                  55                  60

Met Pro Glu Ser Gln Asp Tyr Phe Lys Thr Leu Gln Leu Ile His Lys
 65                  70                  75                  80

Ala Asp Ser Ile Asn Val Ala Ile Gln Asp Gly Pro Glu Ala Gly Gln
                85                  90                  95

Ser Val Pro His Leu His Thr His Ile Ile Pro Arg Tyr Lys Ile Asn
                100                 105                 110

Asn Val Gly Asp Leu Ile Tyr Asp Lys Leu Asp His Trp Asp Gly Asn
                115                 120                 125

Gly Thr Leu Thr Asp Trp Gln Gly Arg Arg Asp Glu Tyr Leu Gly Val
                130                 135                 140

Gly Gly Arg Gln Ala Arg Lys Asn Asn Ser Thr Ser Ala Thr Val Asp
145                 150                 155                 160

Gly Asp Glu Leu Ser Gln Gly Pro Asn Val Leu Val Arg Ala Leu Thr
                165                 170                 175

Glu Met Lys Lys Glu Ala Glu Asp Leu Gln Ala Arg Leu Glu Glu Phe
                180                 185                 190

Val Ser Ser Asp Pro Gly Leu Thr Gln Trp Leu
```

```
              195                 200

(2) INFORMATION FOR SEQ ID NO:5:

(i) SEQUENCE CHARACTERISTICS:
         (A) LENGTH: 119 amino acids
         (B) TYPE: amino acid
         (D) TOPOLOGY: unknown (ii) MOLECULE TYPE: protein (xi) SEQUENCE DESCRIPTION: SEQ ID NO:5:

Ala Asp Glu Ile Ala Lys Ala Gln Val Ala Arg Pro Gly Gly Asp Thr
1               5                  10                  15

Ile Phe Gly Lys Ile Ile Arg Lys Glu Ile Pro Ala Lys Ile Ile Tyr
             20                  25                  30

Glu Asp Asp Gln Cys Leu Ala Phe His Asp Ile Ser Pro Gln Ala Pro
         35                  40                  45

Thr His Phe Leu Val Ile Pro Lys Lys Tyr Ile Ser Gln Ile Ser Ala
     50                  55                  60

Ala Glu Asp Asp Glu Ser Leu Leu Gly His Leu Met Ile Val Gly
65                  70                  75                  80

Lys Lys Cys Ala Lys Gly Tyr Arg Met Val Val Asn Glu Gly Ser Asp
                 85                  90                  95

Gly Gly Gln Ser Val Tyr His Val His Leu His Val Leu Gly Gly Arg
             100                 105                 110

Gln Met Asn Trp Pro Pro Gly
             115

(2) INFORMATION FOR SEQ ID NO:6:

(i) SEQUENCE CHARACTERISTICS:
         (A) LENGTH: 108 amino acids
         (B) TYPE: amino acid
         (D) TOPOLOGY: unknown (ii) MOLECULE TYPE: protein (xi) SEQUENCE DESCRIPTION: SEQ ID NO:6:

Met Ser Glu Asp Thr Ile Phe Gly Lys Ile Ile Arg Arg Glu Ile Pro
1               5                  10                  15

Ala Asp Ile Val Tyr Glu Asp Asp Leu Cys Leu Ala Phe Arg Asp Val
             20                  25                  30

Ala Pro Gln Ala Pro Val His Ile Leu Val Ile Pro Lys Gln Pro Ile
         35                  40                  45

Ala Asn Leu Leu Glu Ala Thr Ala Glu His Gln Ala Leu Leu Gly His
     50                  55                  60

Leu Leu Leu Thr Val Lys Ala Ile Ala Glu Gly Tyr Arg Thr Val Ile
65                  70                  75                  80

Asn Thr Gly Pro Ala Gly Gly Gln Thr Val Tyr His Leu His Ile His
                 85                  90                  95

Leu Leu Gly Gly Arg Ser Leu Ala Trp Pro Pro Gly
             100                 105

(2) INFORMATION FOR SEQ ID NO:7:

(i) SEQUENCE CHARACTERISTICS:
         (A) LENGTH: 104 amino acids
         (B) TYPE: amino acid
         (D) TOPOLOGY: unknown (ii) MOLECULE TYPE: protein
```

(xi) SEQUENCE DESCRIPTION: SEQ ID NO:7:

| Met | Asn | Asn | Trp | Gln | Glu | Leu | Phe | Leu | Lys | Ile | Ile | Lys | Arg | Glu |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Glu | Pro | Ala | Thr | Ile | Leu | Tyr | Glu | Asp | Lys | Val | Ile | Ala | Phe | Leu |
|-----|-----|-----|-----|-----|-----|-----|-----|-----|-----|-----|-----|-----|-----|-----|
|     |     |     | 20  |     |     |     |     | 25  |     |     |     | 30  |     |     |

| Asp | Lys | Tyr | Ala | His | Thr | Lys | Gly | His | Phe | Leu | Val | Val | Pro | Lys | Asn |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Tyr | Ser | Arg | Asn | Leu | Phe | Ser | Ile | Ser | Asp | Glu | Asp | Leu | Ser | Tyr | Leu |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ile | Val | Lys | Ala | Arg | Glu | Phe | Ala | Gly | Ala | Thr | Gly | Phe | Lys | Leu | Leu |
|-----|-----|-----|-----|-----|-----|-----|-----|-----|-----|-----|-----|-----|-----|-----|-----|
| 65  |     |     |     | 70  |     |     |     |     | 75  |     |     |     |     | 80  |     |

| Ile | Asn | Asn | Glu | Pro | Asp | Ala | Glu | Gln | Ser | Ile | Phe | His | Thr | His | Val |
|-----|-----|-----|-----|-----|-----|-----|-----|-----|-----|-----|-----|-----|-----|-----|-----|
|     |     |     | 85  |     |     |     |     | 90  |     |     |     |     | 95  |     |     |

| His | Ile | Ile | Pro | Tyr | Tyr | Lys | Lys |
|-----|-----|-----|-----|-----|-----|-----|-----|
|     |     |     | 100 |     |     |     |     |

(2) INFORMATION FOR SEQ ID NO:8:

(i) SEQUENCE CHARACTERISTICS:
        (A) LENGTH: 151 amino acids
        (B) TYPE: amino acid
        (D) TOPOLOGY: unknown (ii) MOLECULE TYPE: protein (xi) SEQUENCE DESCRIPTION: SEQ ID NO:8:

| Met | Glu | Pro | Leu | Ile | Ser | Ala | Pro | Tyr | Leu | Thr | Thr | Lys | Met | Ser |
|-----|-----|-----|-----|-----|-----|-----|-----|-----|-----|-----|-----|-----|-----|-----|
| 1   |     |     |     | 5   |     |     |     |     | 10  |     |     |     | 15  |     |

| Ala | Pro | Ala | Thr | Leu | Asp | Ala | Ala | Cys | Ile | Phe | Cys | Lys | Ile | Ile | Lys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ser | Glu | Ile | Pro | Ser | Phe | Lys | Leu | Ile | Glu | Thr | Lys | Tyr | Ser | Tyr | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Phe | Leu | Asp | Ile | Gln | Pro | Thr | Ala | Glu | Gly | His | Ala | Leu | Ile | Ile | Pro |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Lys | Tyr | His | Gly | Ala | Lys | Leu | His | Asp | Ile | Pro | Asp | Glu | Phe | Leu | Thr |
|-----|-----|-----|-----|-----|-----|-----|-----|-----|-----|-----|-----|-----|-----|-----|-----|
| 65  |     |     |     | 70  |     |     |     |     | 75  |     |     |     |     | 80  |     |

| Asp | Ala | Met | Pro | Ile | Ala | Lys | Leu | Asp | Thr | Tyr | Asn | Val | Leu | Gln | Asn |
|-----|-----|-----|-----|-----|-----|-----|-----|-----|-----|-----|-----|-----|-----|-----|-----|
|     |     |     | 85  |     |     |     |     | 90  |     |     |     |     | 95  |     |     |

| Asn | Gly | Lys | Ile | Ala | His | Gln | Glu | Val | Asp | His | Val | His | Phe | His | Leu |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Ile | Pro | Lys | Arg | Asp | Glu | Lys | Ser | Gly | Leu | Ile | Val | Gly | Trp | Pro | Ala |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Gln | Glu | Thr | Asp | Phe | Asp | Lys | Leu | Gly | Lys | Leu | His | Lys | Glu | Leu | Leu |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ala | Lys | Leu | Glu | Gly | Ser | Asp |
|-----|-----|-----|-----|-----|-----|-----|
| 145 |     |     |     | 150 |     |     |

(2) INFORMATION FOR SEQ ID NO:9:

(i) SEQUENCE CHARACTERISTICS:
        (A) LENGTH: 455 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:9:

AAGAAAACCG GANAGACTTT GAAGCACGTT CACGTCCACG TTNTTCCCGG GAAGGCTGGA    60

```
AAACTTTCAC AGGAATGACA GCATCTATGA GGAGCTCCCA GAAANATGAC AAGGAGGACT    120

TTCCTGCCTC TTGGAGATCA GAGGAGGAAA TGGCAGCAGA AAGCCGCAGC TCTGCGGGTC    180

TACTTTCAGT GACACAGATC CTGAATTCCA GCAAAAGAGC TATTGCCAAC CAGTTTGAAN    240

ACCGCCCCCC CGCCTCTCCC CAAGAGGAAC TGAATCAGCA TGAAAATGCA GTTTCTTCAT    300

CTCACCATCC TGTANTCTTC AACCAGTGAT CCCCCACCTC GGTCACTCCA ACTCCCTTAA    360

AATACCTAGA CCTAAACGGC TCAGACAGGC AGATTTGAGG TTTCCCCCTG TCTCCTTATT    420

CGGCAGCCTT ATGATTAAAC TTCCNNCTCT GCTGC                              455

(2) INFORMATION FOR SEQ ID NO:10:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (xi) SEQUENCE DESCRIPTION: SEQ ID NO:10:

Ala Ala Glu Xaa Glu Val
1               5

(2) INFORMATION FOR SEQ ID NO:11:

(i) SEQUENCE CHARACTERISTICS:
        (A) LENGTH: 15 amino acids
        (B) TYPE: amino acid
        (D) TOPOLOGY: unknown (ii) MOLECULE TYPE: peptide (xi) SEQUENCE DESCRIPTION: SEQ ID NO:11:

Gly Cys Arg Ile Arg Arg Gln Gly Glu Thr Ser Asn Leu Pro Val
1               5                   10                  15

(2) INFORMATION FOR SEQ ID NO:12:

(i) SEQUENCE CHARACTERISTICS:
        (A) LENGTH: 19 amino acids
        (B) TYPE: amino acid
        (D) TOPOLOGY: unknown (ii) MOLECULE TYPE: peptide (xi) SEQUENCE DESCRIPTION: SEQ ID NO:12:

Gly Ser Trp Ser Asp Arg Gly Gly Ser Leu Val Glu Xaa Tyr Arg
1               5                   10                  15
Met Val Arg (2) INFORMATION FOR SEQ ID NO:13:

(i) SEQUENCE CHARACTERISTICS:
        (A) LENGTH: 36 amino acids
        (B) TYPE: amino acid
        (D) TOPOLOGY: unknown (ii) MOLECULE TYPE: peptide (xi) SEQUENCE DESCRIPTION: SEQ ID NO:13:

Arg Asn Cys Ile Phe Met Leu Ile Gln Phe Leu Leu Gly Arg Gly Gly
1               5                   10                  15
Gly Ala Xaa Phe Lys Leu Val Gly Asn Ser Ser Phe Ala Gly Ile Gln
            20                  25                  30
```

```
Asp Leu Cys His
        35
```

(2) INFORMATION FOR SEQ ID NO:14:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO:14:

```
Thr Arg Arg Ala Ala Ala Phe Cys Cys His Phe Leu Leu
1               5                   10
```

(2) INFORMATION FOR SEQ ID NO:15:

(i) SEQUENCE CHARACTERISTICS:
        (A) LENGTH: 35 amino acids
        (B) TYPE: amino acid
        (D) TOPOLOGY: unknown (ii) MOLECULE TYPE: peptide (xi) SEQUENCE DESCRIPTION: SEQ ID NO:15:

```
Ser Pro Arg Gly Arg Lys Val Leu Leu Val Xaa Phe Leu Gly Ala Pro
1               5                   10                  15

His Arg Cys Cys His Ser Cys Glu Ser Phe Pro Ala Phe Pro Gly Xaa
                20                  25                  30

Thr Trp Thr
        35
```

(2) INFORMATION FOR SEQ ID NO:16:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (xi) SEQUENCE DESCRIPTION: SEQ ID NO:16:

```
Gln Gln Xaa Xaa Lys Phe Asn His Lys Ala Ala Glu
1               5                   10
```

(2) INFORMATION FOR SEQ ID NO:17:

(i) SEQUENCE CHARACTERISTICS:
        (A) LENGTH: 37 amino acids
        (B) TYPE: amino acid
        (D) TOPOLOGY: unknown (ii) MOLECULE TYPE: peptide (xi) SEQUENCE DESCRIPTION: SEQ ID NO:17:

```
Gly Asp Arg Gly Lys Pro Gln Ile Cys Leu Ser Glu Pro Phe Arg Ser
1               5                   10                  15

Arg Tyr Phe Lys Gly Val Gly Val Thr Glu Val Gly Asp His Trp Leu
                20                  25                  30

Lys Xaa Thr Gly Trp
        35
```

(2) INFORMATION FOR SEQ ID NO:18:

(i) SEQUENCE CHARACTERISTICS:
        (A) LENGTH: 8 amino acids

```
      (B) TYPE: amino acid
      (D) TOPOLOGY: unknown (ii) MOLECULE TYPE: peptide (xi) SEQUENCE DESCRIPTION: SEQ ID NO:18:

Asp Glu Glu Thr Ala Phe Ser Cys
1               5

(2) INFORMATION FOR SEQ ID NO:19:

(i) SEQUENCE CHARACTERISTICS:
      (A) LENGTH: 91 amino acids
      (B) TYPE: amino acid
      (D) TOPOLOGY: unknown (ii) MOLECULE TYPE: peptide (xi) SEQUENCE DESCRIPTION: SEQ ID NO:19:

Phe Ser Ser Ser Trp Gly Glu Ala Gly Gly Arg Xaa Ser Asn Trp Leu
1               5                  10                  15

Ala Ile Ala Leu Leu Leu Glu Phe Arg Ile Cys Val Thr Glu Ser Arg
            20                  25                  30

Pro Ala Glu Leu Arg Leu Ser Ala Ala Ile Ser Ser Ser Asp Leu Gln
        35                  40                  45

Glu Ala Gly Lys Ser Ser Leu Ser Xaa Phe Trp Glu Leu Leu Ile Asp
50                  55                  60

Ala Val Ile Pro Val Lys Val Phe Gln Pro Ser Arg Glu Xaa Arg Gly
65                  70                  75                  80

Arg Glu Arg Ala Ser Lys Ser Xaa Arg Phe Ser
                85                  90

(2) INFORMATION FOR SEQ ID NO:20:

(i) SEQUENCE CHARACTERISTICS:
      (A) LENGTH: 36 amino acids
      (B) TYPE: amino acid
      (D) TOPOLOGY: unknown (ii) MOLECULE TYPE: peptide (xi) SEQUENCE DESCRIPTION: SEQ ID NO:20:

Ser Arg Xaa Gly Ser Leu Ile Ile Arg Leu Pro Asn Lys Glu Thr Gly
1               5                  10                  15

Gly Asn Leu Lys Ser Ala Cys Leu Ser Arg Leu Gly Leu Gly Ile Leu
            20                  25                  30

Arg Glu Leu Glu
        35

(2) INFORMATION FOR SEQ ID NO:21:

(i) SEQUENCE CHARACTERISTICS:
      (A) LENGTH: 7 amino acids
      (B) TYPE: amino acid
      (D) TOPOLOGY: unknown (ii) MOLECULE TYPE: peptide (xi) SEQUENCE DESCRIPTION: SEQ ID NO:21:

Pro Arg Trp Gly Ile Thr Gly
1               5

(2) INFORMATION FOR SEQ ID NO:22:

(i) SEQUENCE CHARACTERISTICS:
```

```
        (A) LENGTH: 32 amino acids
        (B) TYPE: amino acid
        (D) TOPOLOGY: unknown (ii) MOLECULE TYPE: peptide (xi) SEQUENCE DESCRIPTION: SEQ ID NO:22:

Arg Xaa Gln Asp Gly Glu Met Lys Lys Leu His Phe His Ala Asp Ser
1               5                  10                 15

Val Pro Leu Gly Glu Arg Arg Gly Gly Xaa Gln Thr Gly Trp Gln
            20                  25                 30

(2) INFORMATION FOR SEQ ID NO:23:

(i) SEQUENCE CHARACTERISTICS:
        (A) LENGTH: 44 amino acids
        (B) TYPE: amino acid
        (D) TOPOLOGY: unknown (ii) MOLECULE TYPE: peptide (xi) SEQUENCE DESCRIPTION: SEQ ID NO:23:

Leu Phe Cys Trp Asn Ser Gly Ser Val Ser Leu Lys Val Asp Pro Gln
1               5                  10                 15

Ser Cys Gly Phe Leu Leu Pro Phe Pro Pro Leu Ile Ser Lys Arg Gln
            20                  25                 30

Glu Ser Pro Pro Cys His Xaa Ser Gly Ser Ser Ser
            35                  40

(2) INFORMATION FOR SEQ ID NO:24:

(i) SEQUENCE CHARACTERISTICS:
        (A) LENGTH: 5 amino acids
        (B) TYPE: amino acid
        (D) TOPOLOGY: unknown (ii) MOLECULE TYPE: peptide (xi) SEQUENCE DESCRIPTION: SEQ ID NO:24:

Met Leu Ser Phe Leu
1               5

(2) INFORMATION FOR SEQ ID NO:25:

(i) SEQUENCE CHARACTERISTICS:
        (A) LENGTH: 22 amino acids
        (B) TYPE: amino acid
        (D) TOPOLOGY: unknown (ii) MOLECULE TYPE: peptide (xi) SEQUENCE DESCRIPTION: SEQ ID NO:25:

Lys Phe Ser Ser Leu Pro Gly Xaa Asn Val Asp Val Asn Val Leu Gln
1               5                  10                 15

Ser Xaa Ser Gly Phe Leu
            20

(2) INFORMATION FOR SEQ ID NO:26:

(i) SEQUENCE CHARACTERISTICS:
        (A) LENGTH: 25 amino acids
        (B) TYPE: amino acid
        (D) TOPOLOGY: unknown (ii) MOLECULE TYPE: peptide (xi) SEQUENCE DESCRIPTION: SEQ ID NO:26:
```

```
Lys Lys Thr Gly Xaa Thr Leu Lys His Val His Val His Val Xaa Pro
1               5                  10                 15
Gly Lys Ala Gly Lys Leu Ser Gln Glu
                20              25
```

(2) INFORMATION FOR SEQ ID NO:27:

(i) SEQUENCE CHARACTERISTICS:
        (A) LENGTH: 33 amino acids
        (B) TYPE: amino acid
        (D) TOPOLOGY: unknown (ii) MOLECULE TYPE: peptide (xi) SEQUENCE DESCRIPTION: SEQ ID NO:27:

```
Gly Ala Pro Arg Xaa Met Thr Arg Arg Thr Phe Leu Pro Leu Gly Asp
1               5                  10                 15
Gln Arg Arg Lys Trp Gln Gln Lys Ala Ala Ala Leu Arg Val Tyr Phe
                20                  25                 30
Gln
```

(2) INFORMATION FOR SEQ ID NO:28:

(i) SEQUENCE CHARACTERISTICS:
        (A) LENGTH: 22 amino acids
        (B) TYPE: amino acid
        (D) TOPOLOGY: unknown (ii) MOLECULE TYPE: peptide (xi) SEQUENCE DESCRIPTION: SEQ ID NO:28:

```
Ile Pro Ala Lys Glu Leu Leu Pro Thr Ser Leu Xaa Thr Ala Pro Pro
1               5                  10                 15
Pro Leu Pro Lys Arg Asn
                20
```

(2) INFORMATION FOR SEQ ID NO:29:

(i) SEQUENCE CHARACTERISTICS:
        (A) LENGTH: 28 amino acids
        (B) TYPE: amino acid
        (D) TOPOLOGY: unknown (ii) MOLECULE TYPE: peptide (xi) SEQUENCE DESCRIPTION: SEQ ID NO:29:

```
Ile Ser Met Lys Met Gln Phe Leu His Leu Thr Ile Leu Xaa Ser Ser
1               5                  10                 15
Thr Ser Asp Pro Pro Pro Arg Ser Leu Gln Leu Pro
                20                  25
```

(2) INFORMATION FOR SEQ ID NO:30:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide (xi) SEQUENCE DESCRIPTION: SEQ ID NO:30:

```
Thr Ala Gln Thr Gly Arg Phe Glu Val Ser Pro Cys Leu Leu Ile Arg
1               5                  10                 15
Gln Pro Tyr Asp
                20
```

(2) INFORMATION FOR SEQ ID NO:31:

(i) SEQUENCE CHARACTERISTICS:
        (A) LENGTH: 5 amino acids
        (B) TYPE: amino acid
        (D) TOPOLOGY: unknown (ii) MOLECULE TYPE: peptide (xi) SEQUENCE DESCRIPTION: SEQ ID NO:31:

Thr Ser Xaa Ser Ala
1               5

(2) INFORMATION FOR SEQ ID NO:32:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (xi) SEQUENCE DESCRIPTION: SEQ ID NO:32:

Arg Lys Pro Xaa Arg Leu
1               5

(2) INFORMATION FOR SEQ ID NO:33:

(i) SEQUENCE CHARACTERISTICS:
        (A) LENGTH: 28 amino acids
        (B) TYPE: amino acid
        (D) TOPOLOGY: unknown (ii) MOLECULE TYPE: peptide (xi) SEQUENCE DESCRIPTION: SEQ ID NO:33:

Ser Thr Phe Thr Ser Thr Xaa Phe Pro Gly Arg Leu Glu Asn Phe His
1               5                   10                  15

Arg Asn Asp Ser Ile Tyr Glu Glu Leu Pro Glu Xaa
                20                  25

(2) INFORMATION FOR SEQ ID NO:34:

(i) SEQUENCE CHARACTERISTICS:
        (A) LENGTH: 42 amino acids
        (B) TYPE: amino acid
        (D) TOPOLOGY: unknown (ii) MOLECULE TYPE: peptide (xi) SEQUENCE DESCRIPTION: SEQ ID NO:34:

Gln Gly Gly Leu Ser Cys Leu Leu Glu Ile Arg Gly Gly Asn Gly Ser
1               5                   10                  15

Arg Lys Pro Gln Leu Cys Gly Ser Thr Phe Ser Asp Thr Asp Pro Glu
                20                  25                  30

Phe Gln Gln Lys Ser Tyr Cys Gln Pro Val
            35                  40

(2) INFORMATION FOR SEQ ID NO:35:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:35:

```
Xaa Pro Pro Pro Arg Leu Ser Pro Arg Gly Thr Glu Ser Ala
1               5                   10
```

(2) INFORMATION FOR SEQ ID NO:36:

(i) SEQUENCE CHARACTERISTICS:
        (A) LENGTH: 57 amino acids
        (B) TYPE: amino acid
        (D) TOPOLOGY: unknown (ii) MOLECULE TYPE: peptide (xi) SEQUENCE DESCRIPTION: SEQ ID NO:36:

```
Lys Cys Ser Phe Phe Ile Ser Pro Ser Cys Xaa Leu Gln Pro Val Ile
1               5                   10                  15

Pro His Leu Gly His Ser Asn Ser Leu Lys Ile Pro Arg Pro Lys Arg
            20                  25                  30

Leu Arg Gln Ala Asp Leu Arg Phe Pro Pro Val Ser Leu Phe Gly Ser
            35                  40                  45

Leu Met Ile Lys Leu Xaa Xaa Leu Leu
50                  55
```

(2) INFORMATION FOR SEQ ID NO:37:

(i) SEQUENCE CHARACTERISTICS:
        (A) LENGTH: 108 amino acids
        (B) TYPE: amino acid
        (D) TOPOLOGY: unknown (ii) MOLECULE TYPE: peptide (xi) SEQUENCE DESCRIPTION: SEQ ID NO:37:

```
Glu Asn Arg Xaa Asp Phe Glu Ala Arg Ser Arg Pro Arg Xaa Ser Arg
1               5                   10                  15

Glu Gly Trp Lys Thr Phe Thr Gly Met Thr Ala Ser Met Arg Ser Ser
            20                  25                  30

Gln Lys Xaa Asp Lys Glu Asp Phe Pro Ala Ser Trp Arg Ser Glu Glu
            35                  40                  45

Glu Met Ala Ala Glu Ser Arg Ser Ser Ala Gly Leu Leu Ser Val Thr
50                  55                  60

Gln Ile Leu Asn Ser Ser Lys Arg Ala Ile Ala Asn Gln Phe Glu Xaa
65                  70                  75                  80

Arg Pro Pro Ala Ser Pro Gln Glu Glu Leu Asn Gln His Glu Asn Ala
            85                  90                  95

Val Ser Ser His His Pro Val Xaa Phe Asn Gln
            100                 105
```

(2) INFORMATION FOR SEQ ID NO:38:

(i) SEQUENCE CHARACTERISTICS:
        (A) LENGTH: 22 amino acids
        (B) TYPE: amino acid
        (D) TOPOLOGY: unknown (ii) MOLECULE TYPE: peptide (xi) SEQUENCE DESCRIPTION: SEQ ID NO:38:

```
Ser Pro Thr Ser Val Thr Pro Thr Pro Leu Lys Tyr Leu Asp Leu Asn
1               5                   10                  15

Gly Ser Asp Arg Gln Ile
            20
```

(2) INFORMATION FOR SEQ ID NO:39:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (xi) SEQUENCE DESCRIPTION: SEQ ID NO:39:

```
Gly Phe Pro Leu Ser Pro Tyr Ser Ala Ala Leu
1               5                   10
```

(2) INFORMATION FOR SEQ ID NO:40:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (xi) SEQUENCE DESCRIPTION: SEQ ID NO:40:

```
Leu Asn Phe Xaa Leu Cys Cys
1               5
```

(2) INFORMATION FOR SEQ ID NO:41:

(i) SEQUENCE CHARACTERISTICS:
        (A) LENGTH: 48 amino acids
        (B) TYPE: amino acid
        (D) TOPOLOGY: unknown (ii) MOLECULE TYPE: peptide (xi) SEQUENCE DESCRIPTION: SEQ ID NO:41:

```
Glu Gln Ser Val Lys Val Arg Ser Ala Ile Tyr Ile Gln Thr Val Glu
1               5                   10                  15

Gly Arg Glu Arg Glu Arg Arg Tyr Pro Arg Asn Thr Cys Leu Leu Arg
                20                  25                  30

Pro Ser Ile Lys Ala Leu Cys Ile Leu Pro Leu Arg Thr Pro Lys Arg
            35                  40                  45
```

(2) INFORMATION FOR SEQ ID NO:42:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (xi) SEQUENCE DESCRIPTION: SEQ ID NO:42:

```
Gln Ser Ser Glu Arg Leu Gln Leu
1               5
```

(2) INFORMATION FOR SEQ ID NO:43:

(i) SEQUENCE CHARACTERISTICS:
        (A) LENGTH: 28 amino acids
        (B) TYPE: amino acid
        (D) TOPOLOGY: unknown (ii) MOLECULE TYPE: peptide (xi) SEQUENCE DESCRIPTION: SEQ ID NO:43:

```
Gly His Val Val Gln Ile Trp Pro Thr Ser His Gln Ala Leu Cys Ser
1               5                   10                  15
```

```
Val Ser Gln Asn Arg Thr Val Leu Arg Ser Cys Glu
            20              25
```

(2) INFORMATION FOR SEQ ID NO:44:

(i) SEQUENCE CHARACTERISTICS:
        (A) LENGTH: 50 amino acids
        (B) TYPE: amino acid
        (D) TOPOLOGY: unknown (ii) MOLECULE TYPE: peptide (xi) SEQUENCE DESCRIPTION: SEQ ID NO:44:

```
Glu Thr Cys Gly Thr Arg Asp Met Ser Leu Cys Ala Arg Cys Gly Gln
1               5                   10                  15
Trp Glu Arg Phe His Asp Leu Arg Pro Asp Glu Val Gly Arg Phe Val
            20                  25                  30
Ser Asp Asp Pro Glu Ser Ser Gly Gln Trp Leu Xaa Lys His Phe Pro
        35                  40                  45
Gly Asp
    50
```

(2) INFORMATION FOR SEQ ID NO:45:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (xi) SEQUENCE DESCRIPTION: SEQ ID NO:45:

```
Ser Thr Glu Asn Ser Leu
1               5
```

(2) INFORMATION FOR SEQ ID NO:46:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (xi) SEQUENCE DESCRIPTION: SEQ ID NO:46:

```
Arg Ser Val Val Leu Ser Thr Ser Arg Arg Trp Lys Gly Glu Lys Glu
1               5                   10                  15
Lys Glu Gly Ile Leu Gly Ile Pro Ala Cys Leu Asp Pro Leu
            20                  25                  30
```

(2) INFORMATION FOR SEQ ID NO:47:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (xi) SEQUENCE DESCRIPTION: SEQ ID NO:47:

```
Lys Leu Cys Ala Ser Cys His
1               5
```

(2) INFORMATION FOR SEQ ID NO:48:

(i) SEQUENCE CHARACTERISTICS:
        (A) LENGTH: 93 amino acids (B) TYPE: amino acid
(D) TOPOLOGY: unknown (ii) MOLECULE TYPE: peptide (xi) SEQUENCE DESCRIPTION: SEQ ID NO:48:

Gly Leu Arg Arg Gly Ser Ser Leu Leu Lys Asp Phe Asn Cys Glu Asp
1               5                   10                  15

Met Ser Phe Arg Phe Gly Gln His Leu Ile Lys Pro Ser Val Val Phe
            20                  25                  30

Leu Lys Thr Glu Leu Ser Phe Ala Leu Val Asn Arg Lys Pro Val Val
                35                  40                  45

Pro Gly Thr Cys Pro Cys Val Pro Ala Ala Ser Gly Ser Ala Ser
        50              55                  60

Met Thr Cys Val Leu Met Lys Trp Ala Asp Leu Phe Gln Thr Thr Gln
65                  70                  75                  80

Arg Val Arg Asp Ser Gly Trp Xaa Asn Ile Phe Leu Gly
                85                  90

(2) INFORMATION FOR SEQ ID NO:49:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (xi) SEQUENCE DESCRIPTION: SEQ ID NO:49:

Pro Leu Arg Thr Val Cys Lys Gly Pro
1               5

(2) INFORMATION FOR SEQ ID NO:50:

(i) SEQUENCE CHARACTERISTICS:
        (A) LENGTH: 17 amino acids
        (B) TYPE: amino acid
        (D) TOPOLOGY: unknown (ii) MOLECULE TYPE: peptide (xi) SEQUENCE DESCRIPTION: SEQ ID NO:50:

Cys Tyr Leu His Pro Asp Gly Gly Arg Glu Arg Lys Arg Lys Lys Val
1               5                   10                  15

Ser (2) INFORMATION FOR SEQ ID NO:51:

(i) SEQUENCE CHARACTERISTICS:
        (A) LENGTH: 5 amino acids
        (B) TYPE: amino acid
        (D) TOPOLOGY: unknown (ii) MOLECULE TYPE: peptide (xi) SEQUENCE DESCRIPTION: SEQ ID NO:51:

Glu Tyr Leu Pro Ala
1               5

(2) INFORMATION FOR SEQ ID NO:52:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide (xi) SEQUENCE DESCRIPTION: SEQ ID NO:52:

Thr Leu Tyr Lys Ser Ser Val His Pro Ala Thr Glu Asp Ser Glu Glu
1               5                  10                  15

Val Ala Val Phe
            20

(2) INFORMATION FOR SEQ ID NO:53:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide (xi) SEQUENCE DESCRIPTION: SEQ ID NO:53:

Lys Thr Ser Thr Val Arg Thr Cys Arg Ser Asp Leu Ala Asn Ile Ser
1               5                  10                  15

Ser Ser Pro Leu
            20

(2) INFORMATION FOR SEQ ID NO:54:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (xi) SEQUENCE DESCRIPTION: SEQ ID NO:54:

Cys Phe Ser Lys Gln Asn Cys Pro Ser Leu Leu
1               5                  10

(2) INFORMATION FOR SEQ ID NO:55:

(i) SEQUENCE CHARACTERISTICS:
        (A) LENGTH: 22 amino acids
        (B) TYPE: amino acid
        (D) TOPOLOGY: unknown (ii) MOLECULE TYPE: peptide (xi) SEQUENCE DESCRIPTION: SEQ ID NO:55:

Ile Gly Asn Leu Trp Tyr Gln Gly His Val Leu Val Cys Pro Leu Arg
1               5                  10                  15

Pro Val Gly Ala Leu Pro
            20

(2) INFORMATION FOR SEQ ID NO:56:

(i) SEQUENCE CHARACTERISTICS:
        (A) LENGTH: 23 amino acids
        (B) TYPE: amino acid
        (D) TOPOLOGY: unknown (ii) MOLECULE TYPE: peptide (xi) SEQUENCE DESCRIPTION: SEQ ID NO:56:

Ser Gly Pro Ile Cys Phe Arg Arg Pro Arg Glu Phe Gly Thr Val Val
1               5                  10                  15

Gly Xaa Thr Phe Ser Trp Gly
            20

(2) INFORMATION FOR SEQ ID NO:57:

(i) SEQUENCE CHARACTERISTICS:
        (A) LENGTH: 17 amino acids
        (B) TYPE: amino acid
        (D) TOPOLOGY: unknown (ii) MOLECULE TYPE: peptide (xi) SEQUENCE DESCRIPTION: SEQ ID NO:57:

Val Pro Arg Lys Met Phe Xaa Gln Pro Leu Ser Arg Thr Leu Trp Val
1               5                   10                  15
Val (2) INFORMATION FOR SEQ ID NO:58:

(i) SEQUENCE CHARACTERISTICS:
        (A) LENGTH: 122 amino acids
        (B) TYPE: amino acid
        (D) TOPOLOGY: unknown (ii) MOLECULE TYPE: peptide (xi) SEQUENCE DESCRIPTION: SEQ ID NO:58:

Asn Lys Ser Ala His Phe Ile Arg Thr Gln Val Met Glu Ala Leu Pro
1               5                   10                  15

Leu Ala Ala Gly Thr Gln Gly His Val Pro Gly Thr Thr Gly Phe
                20                  25                  30

Leu Phe Thr Arg Ala Lys Asp Ser Ser Val Leu Arg Asn Thr Thr Glu
                35                  40                  45

Gly Leu Met Arg Cys Trp Pro Asn Leu Asn Asp Met Ser Ser Gln Leu
                50                  55                  60

Lys Ser Phe Arg Arg Leu Leu Pro Leu Arg Ser Pro Gln Trp Gln Asp
65                  70                  75                  80

Ala Gln Ser Phe Tyr Arg Gly Ser Lys Gln Ala Gly Ile Pro Arg Ile
                85                  90                  95

Pro Ser Phe Ser Phe Ser Pro Phe His Arg Leu Asp Val Asp Ser Thr
                100                 105                 110

Thr Asp Leu Tyr Arg Leu Phe Ser Val Asp
            115                 120

(2) INFORMATION FOR SEQ ID NO:59:

(i) SEQUENCE CHARACTERISTICS:
        (A) LENGTH: 60 amino acids
        (B) TYPE: amino acid
        (D) TOPOLOGY: unknown (ii) MOLECULE TYPE: peptide (xi) SEQUENCE DESCRIPTION: SEQ ID NO:59:

Ser Pro Gly Lys Cys Xaa Ser Asn His Cys Pro Glu Leu Ser Gly Ser
1               5                   10                  15

Ser Glu Thr Asn Arg Pro Thr Ser Ser Gly Arg Arg Ser Trp Lys Arg
                20                  25                  30

Ser His Trp Pro Gln Arg Ala His Lys Asp Met Ser Leu Val Pro Gln
            35                  40                  45

Val Ser Tyr Ser Gln Glu Arg Arg Thr Val Leu Phe
50                  55                  60

(2) INFORMATION FOR SEQ ID NO:60:

(i) SEQUENCE CHARACTERISTICS:

(A) LENGTH: 6 amino acids
            (B) TYPE: amino acid
            (D) TOPOLOGY: unknown (ii) MOLECULE TYPE: peptide (xi) SEQUENCE DESCRIPTION: SEQ ID NO:60:

Glu Thr Leu Gln Arg Ala
1               5

(2) INFORMATION FOR SEQ ID NO:61:

(i) SEQUENCE CHARACTERISTICS:
            (A) LENGTH: 5 amino acids
            (B) TYPE: amino acid
            (D) TOPOLOGY: unknown (ii) MOLECULE TYPE: peptide (xi) SEQUENCE DESCRIPTION: SEQ ID NO:61:

Asp Val Gly Gln Ile
1               5

(2) INFORMATION FOR SEQ ID NO:62:

(i) SEQUENCE CHARACTERISTICS:
            (A) LENGTH: 6 amino acids
            (B) TYPE: amino acid
            (D) TOPOLOGY: unknown (ii) MOLECULE TYPE: peptide (xi) SEQUENCE DESCRIPTION: SEQ ID NO:62:

Thr Thr Cys Pro His Ser
1               5

(2) INFORMATION FOR SEQ ID NO:63:

(i) SEQUENCE CHARACTERISTICS:
            (A) LENGTH: 44 amino acids
            (B) TYPE: amino acid
            (D) TOPOLOGY: unknown (ii) MOLECULE TYPE: peptide (xi) SEQUENCE DESCRIPTION: SEQ ID NO:63:

Ser Leu Ser Glu Asp Cys Tyr Leu Phe Gly Val Leu Ser Gly Arg Met
1               5                   10                  15

His Arg Ala Phe Ile Glu Gly Leu Ser Arg Gln Val Phe Leu Gly Tyr
            20                  25                  30

Leu Leu Ser Leu Ser Leu Pro Ser Thr Val Trp Met
            35                  40

(2) INFORMATION FOR SEQ ID NO:64:

(i) SEQUENCE CHARACTERISTICS:
            (A) LENGTH: 12 amino acids
            (B) TYPE: amino acid
            (D) TOPOLOGY: unknown (ii) MOLECULE TYPE: peptide (xi) SEQUENCE DESCRIPTION: SEQ ID NO:64:

Ile Ala Leu Arg Thr Phe Thr Asp Cys Ser Gln Trp
1               5                   10

(2) INFORMATION FOR SEQ ID NO:65:

(i) SEQUENCE CHARACTERISTICS:
           (A) LENGTH: 102 amino acids
           (B) TYPE: amino acid
           (D) TOPOLOGY: unknown (ii) MOLECULE TYPE: peptide (xi) SEQUENCE DESCRIPTION: SEQ ID NO:65:

Pro Gln Glu Asn Val Xaa Pro Thr Thr Val Pro Asn Ser Leu Gly Arg
1               5                  10                  15

Leu Lys Gln Ile Gly Pro Leu His Gln Asp Ala Gly His Gly Ser Ala
            20                  25                  30

Pro Thr Gly Arg Ser Gly His Thr Arg Thr Cys Pro Trp Tyr His Arg
        35                  40                  45

Phe Pro Ile His Lys Ser Glu Gly Gln Phe Cys Phe Glu Lys His Tyr
    50                  55                  60

Arg Gly Leu Asp Glu Met Leu Ala Lys Ser Glu Arg His Val Leu Thr
65                  70                  75                  80

Val Glu Val Phe Gln Lys Thr Ala Thr Ser Ser Glu Ser Ser Val Ala
                85                  90                  95

Gly Cys Thr Glu Leu Leu
            100

(2) INFORMATION FOR SEQ ID NO:66:

(i) SEQUENCE CHARACTERISTICS:
           (A) LENGTH: 5 amino acids
           (B) TYPE: amino acid
           (D) TOPOLOGY: unknown (ii) MOLECULE TYPE: peptide (xi) SEQUENCE DESCRIPTION: SEQ ID NO:66:

Ala Gly Arg Tyr Ser
1               5

(2) INFORMATION FOR SEQ ID NO:67:

(i) SEQUENCE CHARACTERISTICS:
           (A) LENGTH: 15 amino acids
           (B) TYPE: amino acid
           (D) TOPOLOGY: unknown (ii) MOLECULE TYPE: peptide (xi) SEQUENCE DESCRIPTION: SEQ ID NO:67:

Asp Thr Phe Phe Leu Phe Leu Ser Leu Pro Pro Ser Gly Cys Arg
1               5                  10                  15

(2) INFORMATION FOR SEQ ID NO:68:

(i) SEQUENCE CHARACTERISTICS:
           (A) LENGTH: 11 amino acids
           (B) TYPE: amino acid
           (D) TOPOLOGY: unknown (ii) MOLECULE TYPE: peptide (xi) SEQUENCE DESCRIPTION: SEQ ID NO:68:

His Tyr Gly Pro Leu Gln Thr Val Leu Ser Gly
1               5                  10

(2) INFORMATION FOR SEQ ID NO:69:

(i) SEQUENCE CHARACTERISTICS:
           (A) LENGTH: 1409 base pairs

```
          (B) TYPE: nucleic acid
          (C) STRANDEDNESS: single
          (D) TOPOLOGY: unknown (ii) MOLECULE TYPE: DNA (xi) SEQUENCE DESCRIPTION: SEQ ID NO:69:

GAAACTTGTG TGCATACGAA TAATAAAATT CGATAATATT GGAATTTTTA GTCCGCTTTA      60

TCTGTTCCAT GATACTGTTA CTTACATATA TGCAAGACGC TATTTTCTCA TAGTCTGTTT     120

GTTTTTTAAG TATATCAATC TTTCTTATTA TATTCCATAG ACACTTTCGC ACATGACTCT     180

CCAGGGACTC CGCGATATGG GTTGTGAGCA TCGTGAAGCT GAATTCAACC AACAACTTAG     240

ATTCTTACAA TATTCGTAAG CCAGAATGCC AAAACAGCTA TATTTCTCCA AGTTTCCTGT     300

TGGAAGTCAA GTTTTTTATC GTACTAAGGT AAGTTAACGG TCTCATGTGT GTAGATATTG     360

GTGTTTGCAA ACTTTTGTTT GTCATTCTTA TTTATTCTAT AACGGCAGAC AGTTTGTGAT     420

TTTTCTTTGG TTGAGGTCAG CTGCTAACGA TTTTAGTTAT CTGCCGCGTT TGTAAACCTG     480

AAACCAATTT TACCAGGTCA TGTTTTGGTA ATTCCGCAAC GGGCGGTCCC TAGATTGAAA     540

GATTTGACAC CTTCAGAGGT AGGATTCTTA TGCTATTCGA AAAAATAATG GAATCTGCAT     600

ACGCTAACTA ATGAAAACTT AGTTGACGGA TTTGTTTACT TCTGTTCGCA AAGTGCAACA     660

GGTAATCGAA AAGGTGTTTT CGGCATCTGC ATCAAACATT GGTATTCAAG TAAGTACTTT     720

GATAGTCAAG GAATAAATAA AAAAACATAT TCCTTTTCAC ATTCAAAATA AAAAATCGTT     780

TTAATTTAGA AGCTGACATT TTGCTTTTAA CTCAATAGGA TGGTGTAGAC GCTGGTCAAA     840

CAGTTCCTCA TGTACATGTT CACATTATCC CTCGTAAAAA GGCAGATTTT TCAGAAAACG     900

ATCTAGTCTA CAGTGAGTTG GAAAAAAACG AAGGAAATCT TGCTTCCCTT TATCTTACGG     960

GAAATGAGCG GTATGCAGGA GATGAGAGAC CGCCAACCAG TATGAGGCAA GCTATTCCTA    1020

AGGACGAGGA TCGTAAGCCA AGAACACTTG AGGAAATGGA AAAGGAAGCT CAGTGGTTGA    1080

AAGGGTACTT TTCCGAAGAG CAAGAGAAGG AATAAAAAGT TGAAGTACCT CAATACCACA    1140

GGGGTAGTGT TTACGTATGA ATTAAGCTAA ATATTATATG ACCCTTTTTT TTTATTTCAC    1200

CCAAGGTTAC AAGAAAAATT TCCTTTTTTC TCTCTACCCT GCTTACATTG CATCTGTCTG    1260

CTGAGCTTTA GCAACACAAC GTAACCATAC ATATTGTGAT GAACCCTTCT ACAATTCGAT    1320

CGAATTAGCT TCAGTTCCCT ATTTTGATTT TGCTCTCTTT CTTTCATCCT TTCCTCATAA    1380

CCCTACTAGA TATCCATCTT TTTGAATTC                                     1409

(2) INFORMATION FOR SEQ ID NO:70:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:70:

TCTGCTCTGT CCGGTCACA                                                   19

(2) INFORMATION FOR SEQ ID NO:71:

(i) SEQUENCE CHARACTERISTICS:
          (A) LENGTH: 19 base pairs
          (B) TYPE: nucleic acid
          (C) STRANDEDNESS: single
          (D) TOPOLOGY: linear
```

(ii) MOLECULE TYPE: DNA (xi) SEQUENCE DESCRIPTION: SEQ ID NO:71:

ATGTCCTTGT GTGCCCGCT                                                    19

(2) INFORMATION FOR SEQ ID NO:72:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:72:

TGAGGACATG TCGTTCAGAT TTGG                                              24

(2) INFORMATION FOR SEQ ID NO:73:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:73:

CTGTGTCACT GAAAGTAGAC C                                                 21

(2) INFORMATION FOR SEQ ID NO:74:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:74:

CTGTAAAGGT CCGTAGTG                                                     18

(2) INFORMATION FOR SEQ ID NO:75:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:75:

CTGTGTCACT GAAAGTAGAC C                                                 21

(2) INFORMATION FOR SEQ ID NO:76:

(i) SEQUENCE CHARACTERISTICS:
            (A) LENGTH: 8 amino acids
            (B) TYPE: amino acid
            (D) TOPOLOGY: unknown (ii) MOLECULE TYPE: peptide (xi) SEQUENCE DESCRIPTION: SEQ ID NO:76:

Cys Phe Lys Val Xaa Pro Val Phe
1               5

(2) INFORMATION FOR SEQ ID NO:77:

(i) SEQUENCE CHARACTERISTICS:
        (A) LENGTH: 420 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:77:

```
ATCCACTGAG AACAGTCTGT AAAGGTCCGT AGTGCTATCT ACATCCAGAC GGTGGAAGGG      60

AGAGAAAGAG AAAGAAGGTA TCCTAGGAAT ACCTGCCTGC TTAGACCCTC TATAAAAGCT     120

CTGTGCATCC TGCCACTGAG GACTCCGAAG AGGTAGCAGT CTTCTGAAAG ACTTCAACTG     180

TGAGGACATG TCGTTCAGAT TTGGCCAACA TCTCATCAAG CCCTCTGTAG TGTTTCTCAA     240

AACAGAACTG TCCTTCGCTC TTGTGAATAG GAAACCTGTG GTACCAGGGA CATGTCCTTG     300

TGTGCCCGCT GCGGCCAGTG GGAGCGCTTC CATGACCTGC GTCCTGATGA AGTGGGCCGA     360

TTTGTTTCAG ACGACCCAGA GAGTTCGGGA CAGTGGTTGG ANAAACATTT TCCTGGGGAC     420
```

FHIT PROTEINS AND NUCLEIC ACIDS AND METHODS BASED THEREON

This invention was made in part with government support under Grant numbers CA51083, CA39860, CA21124, and CA56336 awarded by the National Cancer Institute. The government has certain rights in the invention.

1. INTRODUCTION

The present invention relates to nucleotide sequences of the tumor suppressor FHIT genes and amino acid sequences of their encoded proteins, as well as derivatives and analogs thereof and antibodies thereto. The present invention relates to the use of nucleotide sequences of FHIT genes and amino acid sequences of their encoded proteins, as well as derivatives and analogs thereof and antibodies thereto, as diagnostic and therapeutic reagents for the detection and treatment of cancer. The present invention also relates to therapeutic compositions comprising Fhit proteins, derivatives or analogs thereof, antibodies thereto, nucleic acids encoding the Fhit proteins, derivatives or analogs, and FHIT antisense nucleic acids.

2. BACKGROUND OF THE INVENTION

Cancer remains one of the most severe health problems in America, accounting for substantial fatality and health costs in society. Tumorigenesis in humans is a complex process involving activation of oncogenes and inactivation of tumor suppressor genes (Bishop, 1991, Cell 64:235–248). Tumor suppressor genes in humans have been identified through studies of genetic changes occurring in cancer cells (Ponder, 1990, Trends Genet. 6:213–218; Weinberg, 1991, Science 254:1138–1146).

There is a close association between particular chromosomal abnormalities, e.g., chromosomal translocations, inversions, and deletions, and certain types of malignancy, indicating that such abnormalities may have a causative role in the cancer process. Chromosomal abnormalities may lead to gene fusion resulting in chimeric oncoproteins, such as is observed in the majority of the tumors involving the myeloid lineage. Alternatively, chromosomal abnormalities may lead to deregulation of protooncogenes by their juxtaposition to a regulatory element active in the hematopoietic cells, such as is observed in the translocation occurring in the lymphocytic lineage (Virgilio et al., 1993, Proc. Natl. Acad. Sci. USA 90:9275–9279). Deletions may cause loss of tumor suppressor genes, leading to malignancy.

Nonrandom chromosomal translocations are characteristic of most human hematopoietic malignancies (Haluska et al., 1987, Ann. Rev. Genet. 21:321–345) and may be involved in some solid tumors (Croce, 1987, Cell 49:155–156). In B and T cells, chromosomal translocations and inversions often occur as a consequence of mistakes during the normal process of recombination of the genes for immunoglobulins (Ig) or T-cell receptors (TCR). These rearrangements juxtapose enhancer elements of the Ig or TCR genes to oncogenes whose expression is then deregulated (Croce, 1987, Cell 49:155–156). In the majority of the cases, the rearrangements observed in lymphoid malignancies occur between two different chromosomes.

The TCL-1 locus on chromosome 14 band q32.1 is frequently involved in the chromosomal translocations and inversions with the T-cell receptor genes observed in several post-thymic types of T-cell leukemias and lymphomas, including T-prolymphocytic leukemias (T-PLL) (Brito-Babapulle and Catovsky, 1991, Cancer Genet. Cytogenet. 55:1–9), acute and chronic leukemias associated with the immunodeficiency syndrome ataxia-telangiectasia (AT) (Russo et al., 1988, Cell 53:137–144; Russo et al., 1989, Proc. Natl. Acad. Sci. USA 86:602–606), and adult T-cell leukemia (Virgilio et al., 1993, Proc. Natl. Acad. Sci. USA 90:9275–9279).

In 1979, a large Italian-American family in Boston was observed to be transmitting a constitutional reciprocal t(3;8) (p14.2;q24) chromosome translocation (Cohen et al., 1979, N. Engl. J. Med. 301:592–595; Wang and Perkins, 1984, Cancer Genet. Cytogenet. 11:479–481) which segregated in the family with early onset, bilateral and multifocal clear cell renal carcinoma (RCC). Follow-up cytogenetic studies in several familial tumors demonstrated that the tumors had lost the derivative 8 chromosome carrying the translocated 3p14-pter region; consequently, the tumors were homozygous for all loci telomeric to the 3p14.2 break (Li et al., 1993, Annals of Internal Medicine 118:106–111). It was suggested that the translocation affects expression of a tumor suppressor gene (Cohen et al., 1979, N. Engl. J. Med. 301:592–595) and several investigators have sought candidate suppressor genes. We had suggested the protein tyrosine phosphatase gamma gene (PTPRG) as a candidate tumor suppressor gene (LaForgia et al., 1991, Proc. Natl. Acad. Sci. USA 88:5036–5040), and that the majority of clear cell RCCs exhibit loss of heterozygosity of a 0.5 Mb region flanking the translocation (Lubinski et al., 1994, Cancer Res. 54:3710–3713; Druck et al., 1995, Cancer Res. 55:5348–5355), although we did not observe aberrations in the remaining PTPRG gene. The 3p14.2 region is also included in deletions in numerous other tumor types, including nasopharyngeal carcinomas (Lo et al., 1994, Int. J. Oncol. 4:1359–1364).

The t(3;8) translocation breakpoint was cloned and a 3 kb transcript of a candidate tumor suppressor gene was detected using a probe from near the breakpoint (Boldog et al., 1993, Proc. Natl. Acad. Sci. USA 90:8509–8513); further details concerning this transcript have not been reported in spite of a later publication from this group relating to this subject, and reporting a YAC contig of approximately 6 Mb DNA spanning the 3p14.2 3;8 translocation breakpoint (Boldog et al., 1994, Genes, Chromosomes & Cancer 11:216–221). It has also been suggested that there may not be a suppressor gene at 3p14.2, that in fact the t(3;8) translocation was a mechanism for losing the von Hippel-Lindau gene, a tumor suppressor gene at 3p25 (Gnarra et al., 1994, Nature Genet. 7:85–90).

Another cytogenetic landmark in chromosome region 3p14.2 is the most common of the constitutive aphidicolin inducible fragile sites, FRA3B, which is cytogenetically indistinguishable from the t(3;8) translocation (Glover et al., 1988, Cancer Genet. Cytogenet. 31:69–73). Fragile sites, of which over 100 have been described in human (for review, see Sutherland, 1991, Genet. Anal. Tech. Appl. 8:1616–166), are regions of the human genome which reveal cytogenetically detectable gaps when exposed to specific reagents or culture conditions; several folate sensitive, heritable, X-linked and autosomal fragile sites have been localized to unstable CCG or CGG repeats (Yu et al., 1991, Science 252:1179–1181; Kremer et al., 1991, Science 252, 1711–1714; Verkerk et al., 1991, Cell 65:905–914; Fu et al., 1991, Cell 67:1047–1058), and for one of these, the FRA11B at 11q23.3, the CCG repeat is within the 5' untranslated region of the CBL2 gene, a known protooncogene (Jones et al., 1995, Nature 376:145–149). Also this fragile site, FRA11B, is associated with Jacobsen (11q–) syndrome, showing a direct link between a fragile site and in vivo chromosome breakage (Jones et al., 1994, Hum. Mol. Genet. 3:2123–2130). Because the induced fragile sites resemble gaps or breaks in chromosomes, it has frequently been speculated that fragile sites could be sites of chromosomal rearrangement in cancer (Yunis and Soreng, 1984, Science 226:1199–1204).

Previously identified fragile sites have also been shown to be hypermethylated (Knight et al., 1993, Cell 74:127–134); thus methylation of a fragile site in a tumor suppressor gene regulatory region might cause loss of transcription of the suppressor gene, serving as one "hit" in the tumorigenic process, as pointed out previously (Jones et al., 1995, Nature 376:145–149). These authors also suggested that an important contribution of fragile site expression in tumorigenesis might be to increase the incidence of chromosome deletion during tumorigenesis.

The FRA3B region has been delineated by studies of several groups using rodent-human hybrids; hybrid cells retaining human chromosome 3 or 3 and X, on a hamster background, were treated with aphidicolin or 6-thioguanine (t select hybrids which had lost the X chromosome) and subclones selected. Subclones retaining portions of chromosome 3 with apparent breaks in region 3p14–p21 were characterized for loss or retention of specific 3p markers to determine the position of 3p14–21 breaks (LaForgia et al., 1991, Proc. Natl. Acad. Sci. USA 88:5036–5040, LaForgia et al., 1993, Cancer Res. 53:3118–3124; Paradee et al., 1995, Genomics 27:358–361).

There remains an unfulfilled need to isolate and characterize the genes associated with digestive tract and other cancers for use as a diagnostic and therapeutic/prophylactic reagent in the detection, treatment, and prevention of such cancers.

Citation of a reference hereinabove shall not be construed as an admission that such reference is prior art to the present invention.

3. SUMMARY OF THE INVENTION

The present invention relates to nucleotide sequences of FHIT genes, and amino acid sequences of their encoded FHIT proteins, as well as derivatives (e.g., fragments) and analogs thereof, and antibodies thereto. The present invention further relates to nucleic acids hybridizable to or complementary to the foregoing nucleotide sequences as well as equivalent nucleic acid sequences encoding a FHIT protein. In a specific embodiment, the FHIT genes and proteins are human genes and proteins.

Mutations (in particular, deletions) of FHIT gene sequences are associated with esophageal, gastric, colon, kidney, and other cancers.

The present invention also relates to expression vectors encoding a FHIT protein, derivative or analog thereof, as well as host cells containing the expression vectors encoding the FHIT protein, derivative or analog thereof. As used herein, "FHIT" shall be used with reference to the FHIT gene, whereas "Fhit" shall be used with reference to the protein product of the FHIT gene.

The present invention further relates to the use of nucleotide sequences of FHIT genes and amino acid sequences of their encoded Fhit proteins as diagnostic reagents or in the preparation of diagnostic agents useful in the detection of cancer or precancerous conditions or hyperproliferative disorders, in particular those associated with chromosomal or molecular abnormalities, in particular at 3p14.2, and/or decreased levels of expression, or expression of dysfunctional forms, of the Fhit protein. The invention further relates to the use of nucleotide sequences of FHIT genes and amino acid sequences of their encoded Fhit proteins as therapeutic/prophylactic agents in the treatment/prevention of cancer, in particular, associated with chromosomal or molecular abnormalities at 3p14.2, and/or decreased levels of expression, or expression of dysfunctional forms, of the Fhit protein.

The invention also relates to Fhit derivatives and analogs of the invention which are functionally active, i.e., they are capable of displaying one or more known functional activities associated with a full-length (wild-type) Fhit protein. Such functional activities include but are not limited to antigenicity [ability to bind (or compete with Fhit for binding) to an anti-Phit antibody], immunogenicity (ability to generate antibody which binds to Fhit), and ability to bind (or compete with Fhit for binding) to a receptor/ligand or substrate for Fhit, and ability to multmerize with Fhit.

The invention further relates to fragments (and derivatives and analogs thereof) of Fhit which comprise one more domains of a Fhit protein, e.g., the histadine triad, and/or retain the antigenicity of a Fhit protein (i.e., are able to be bound by an anti-Fhit antibody).

The FHIT gene and protein sequences disclosed herein, a antibodies to such protein sequences, may be used in assays diagnose cancers, e.g., digestive tract and airway tumors, associated with chromosomal or molecular abnormalities at 3p14.2, and/or decreased Fhit protein levels or activity by detecting or measuring a decrease in FHIT wild-type mRNA from a patient sample or by detecting or measuring a decrease in levels or activity of Fhit protein from a patient sample, or by detecting an aberrant Fhit DNA, mRNA, or protein.

The Fhit protein, or derivatives or analogs thereof, disclosed herein, may be used for the production of anti-Fhit antibodies which antibodies may be used diagnostically in immunoassays for the detection or measurement of Fhit protein in a patient sample. Anti-Fhit antibodies may be used, for example, for the diagnostic detection or measurement of Fhit protein in biopsied cells and tissues.

The present invention also relates to therapeutic compositions comprising Fhit proteins, derivatives or analogs thereof, antibodies thereto, and nucleic acids encoding the Fhit proteins, derivatives or analogs, and FHIT antisense nucleic acids.

The present invention also relates to therapeutic and diagnostic methods and compositions based on Fhit proteins and nucleic acids. Therapeutic compounds of the invention include but are not limited to Fhit proteins and analogs and derivatives (including fragments) thereof; antibodies thereto; nucleic acids encoding the Fhit proteins, analogs, or derivatives, and FHIT antisense nucleic acids.

The invention provides methods for prevention or treatment of disorders of overproliferation (e.g., cancer and hyperproliferative disorders) by administering compounds that promote Fhit activity (e.g., Fhit, an agonist of Fhit; nucleic acids that encode Fhit).

The invention also provides methods of prevention and treatment of disorders of overproliferation, wherein the patient is hemizygous for a dominant-negative FHIT mutation, by administering compounds that specifically antagonize the FHIT mutant nucleic acid or protein (e.g., antibodies or antisense nucleic acids specific to the mutant).

Animal models, diagnostic methods and screening methods for predisposition to disorders, and methods to identify Fhit agonists and antagonists, are also provided by the invention.

The present invention also relates to methods of production of the Fhit proteins, derivatives and analogs, such as, for example, by recombinant means.

In a particular embodiment of the invention described by way of example in Section 6, a human FHIT sequence is disclosed and shown to be mutated in various cancers.

4. DESCRIPTION OF THE FIGURES

FIGS. 1A–1B. Organization of the FHIT gene relative to the 3p14.2 FRA3B and translocation sites. A scheme of the normal 3p14.2 region is shown (A) with the chromosomal region (not to scale) represented by the top line with positions of STS markers (position of D3S1234 relative to the gene is not known), the FRA3B represented by the hybrid c13 break and the t(3;8) translocation break point shown. The dashed portion represents the region involved in the homozygous deletions in tumor cell lines. Three of the YAC clones used in developing the above markers, map and cosmid contig are shown with the cosmid contig below and the distribution of exons in the FHIT transcript shown below the contig. Black and dotted boxes represent coding and noncoding exons, respectively; asterisks indicate exons with start and stop codons. One exon (E5) falls within the defined homozygously deleted region. Exons 1 (E1), 2 (E2) and 3 (E3) fall centromeric to the t(3;8) translocation break and exon 4 (E4) and 6–10 E6–E10) flank the homozygously deleted region on the centromeric and telomeric sides, respectively. Organization of types of aberrant transcripts from tumor cell lines are illustrated in part B, with zigzag regions representing insertions of new sequence, usually repetitive, into the aberrant transcripts. CCL234 and 235 are colon carcinoma-derived cell lines in which homozygous deletion in the fragile region was not detected. In CCL234 RNA, only an abnormal-sized FHIT transcript was detected by RT-PCR amplification and sequencing; the shorter transcript was shown to result from splicing of exon 3 to exon 5, with omission of the noncoding exon 4, leaving the coding region intact. With CCL235 RNA as template, apparently normal and aberrant RT-PCR products were amplified, with the aberrant product resulting from splicing of exon 4 to exon 8 with a repetitive insert of 140 bp (contributing an in frame Met codon) between E4 and E8. RT-PCR amplification of RNA from HeLa cells, a cervical carcinoma-derived cell line which exhibited a deletion or a rearrangement of DNA near the t(3;8) translocation, revealed normal and aberrant-sized products, the smallest product resulting from splicing of exon 4 to exon 9. RT-PCR amplification of RNA from KatoIII, a gastric carcinoma-derived cell line with discontinuous deletions involving the D3S1481 locus and an ~50 kbp region between exons 5 and 6, apparently leaving all FHIT exons intact, resulted in only an aberrant-sized product which is missing exons 4 through 7, with an 86 bp repeat, inserted downstream of exon 3, contributing an in frame Met codon. Amplification of the RT product from HT29, a colon carcinoma-derived cell line with a large deletion (~200 kbp, about the size of the 648D4 YAC), which included exon 5, gave only an aberrant-sized product resulting from splicing of exon 3 to exon 7. Numerous other tumor-derived cell lines from lung carcinoma (1/3 tested), osteosarcoma (1/1), NPC (3/3), ovarian carcinoma (2/2), and hematopoietic (4/5) tumors, exhibited aberrant FHIT transcription products. The RF48 cell line, from a stomach carcinoma without deletion, showed a normal-sized product, as did a lymphoblastoid line with the t(3;8) translocation, a melanoma (WM1158) and a kidney carcinoma (RC17)-derived cell line. Other colon and stomach carcinoma-derived lines with deletion (AGS, LS180, LoVo), or without deletion (Colo320), showed aberrant reverse transcriptase-polymerase chain reaction (RT-PCR) products (not shown).

FIGS. 2A–2B. Structure of normal and aberrant FHIT cDNAs. The nucleotide (SEQ ID NO:1) and predicted amino acid (SEQ ID NO:2) sequences of the FHIT gene are shown (A) with positions of exons indicated by arrowheads above the sequence and positions of primers used in nested PCR and RACE reactions indicated by arrows below the sequence. A schematic presentation of some of the aberrant transcripts observed in uncultured tumor tissues of digestive organs is shown in B. Only transcripts which showed deletion of coding sequence in Table 3 are presented. The top line in B shows the intact FHIT cDNA map. The thick and thin bars show the coding and untranslated regions, respectively. The positions of splice sites are shown by downward arrows, according to the nucleotide numbers shown above in A. The class I transcripts lack exon 5 while class II transcripts retain exon 5 but generally lose exon 8. In the transcripts with asterisks, insertions of various lengths were observed downstream of exon 4. E1–10 indicate exons 1–10.

Figure 3A:
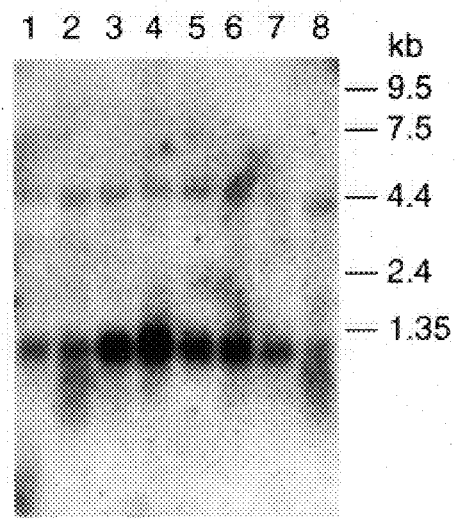
Figure 3B:
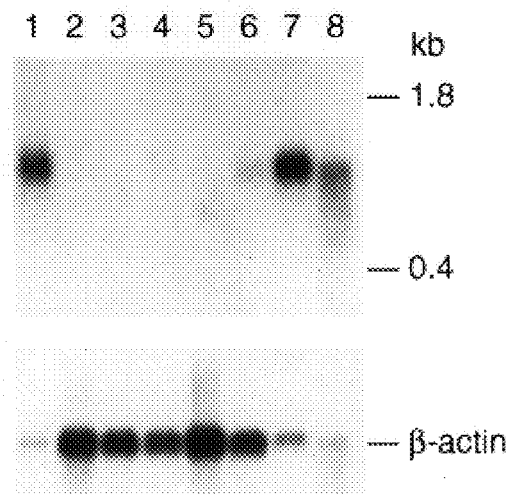
Figure 3C:
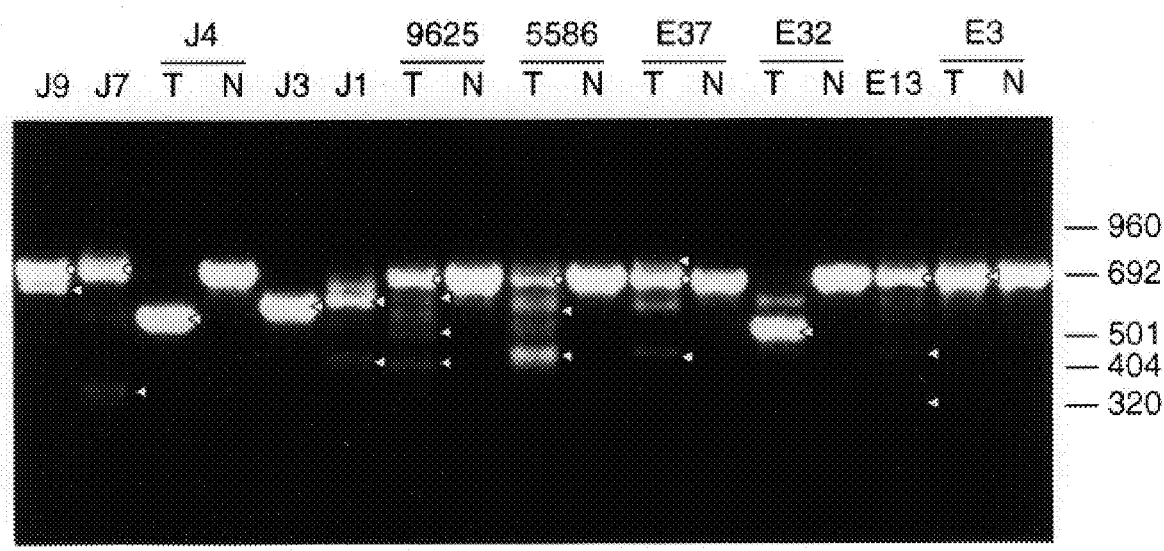

FIGS. 3A–3C. Expression of the FHIT gene in normal tissues and tumors. Northern blot (A, B) and RT-PCR analysis (C) of normal and tumor-derived FHIT mRNA. Panel A shows a northern blot of normal mRNAs (2 µg/lane) from spleen (lane 1), thymus (lane 2), prostate (lane 3), testis (lane 4), ovary (lane 5), small intestine (lane 6), colon (mucosal lining) (lane 7), and peripheral blood leukocytes (lane 8), hybridized with the FHIT cDNA probe. Panel B shows a northern blot of mRNAs (2 µg/lane) from normal small intestine (lane 1) and mRNAs from tumor-derived cell lines: KatoIII (lane 2), HK1(lane 3), LoVo (lane 4), CNE2 (lane 5), CNE1 (lane 6), Colo320 (lane 7), LS180 (lane 8), hybridized with the FHIT cDNA probe (panel B, upper). The same blot was hybridized with a β-actin cDNA probe (panel B, lower). Panel C shows amplified products observed after nested RT-PCR amplification of mRNAs from matched uncultured tumor (T) and normal (N) tissues of the same patients (J4, 9625, 5586, E37, E32, E3), or mRNAs from tumor tissues only (J9, J7, J3, J1, E3). Arrowheads show the positions of amplified products with abnormal DNA sequence. The details of the DNA sequences of corresponding transcripts are shown in Table 2, and FIG. 2B. White dots in the tumor lanes show the position of transcripts with normal DNA sequence.

Figure 4A:
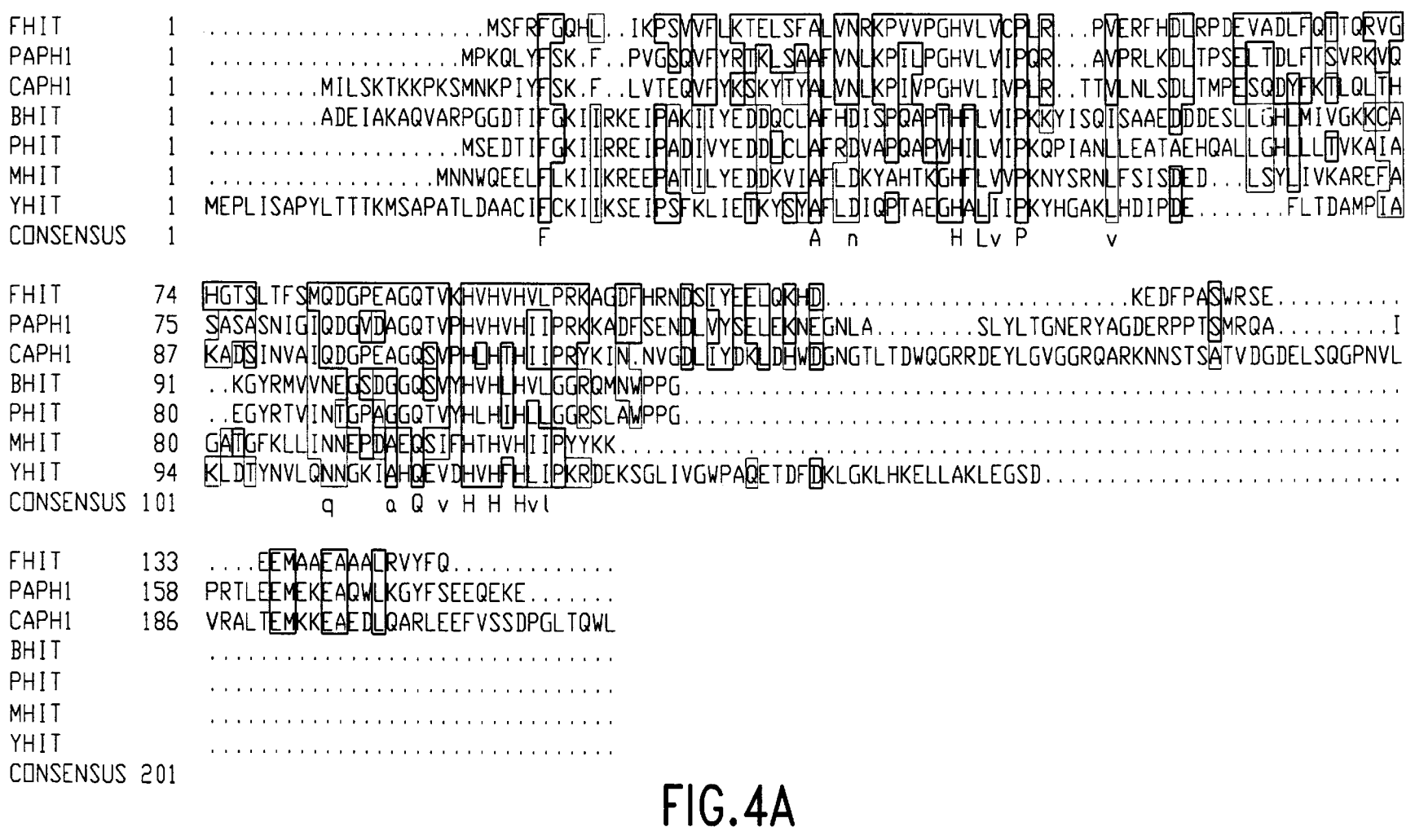
Figure 4B:
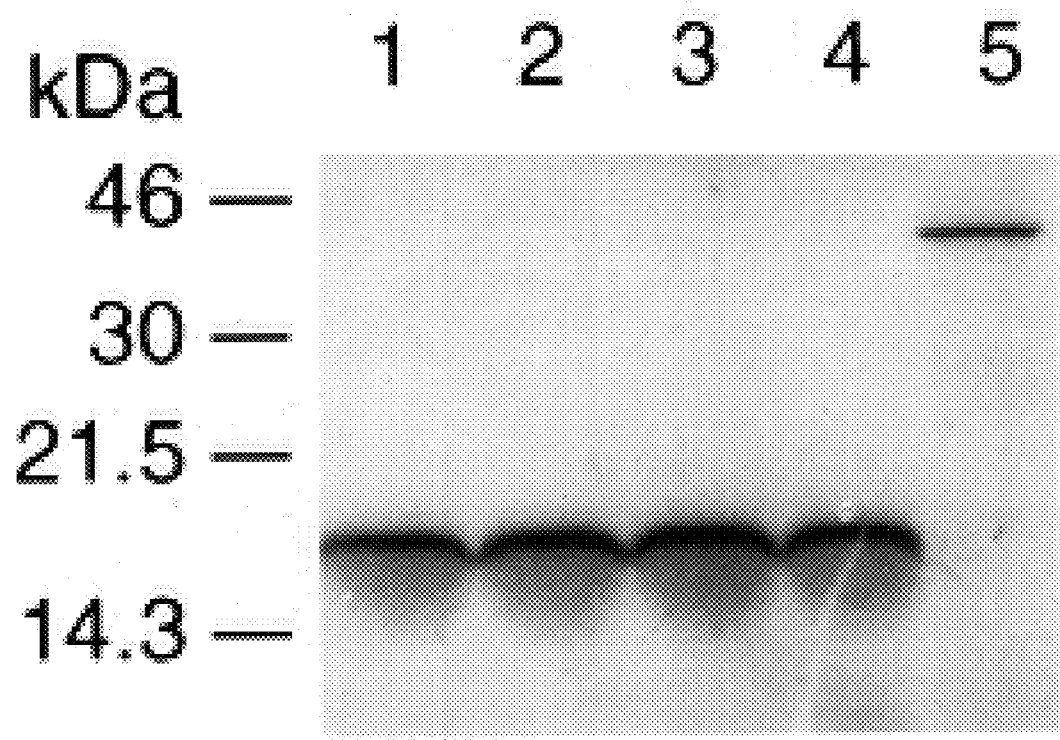

FIGS. 4A–4B. (A) Alignment of amino acid sequences of HIT family proteins and translation of FHIT cDNAs. Alignment was performed using BOXSHADE version 3.0. Outlining in thick lines indicates two or more identical residues at a position; outlining in thin lines shading indicates similarity. The PAPH1 (SEQ ID NO:3) (accession #U32615) and CAPHI (SEQ ID NO:4) (accession #U28374) designate the S. pombe and S. cerevisiae diadenosine 5',5'''-P1, P4 tetraphosphate asymmetric hydrolases (aph1). PHIT (SEQ ID NO:6) indicates the HIT family member from the cyanobacterian Synechococcus Sp. (accession #P32084), BHIT (SEQ ID NO:5), the protein kinase C inhibitor from B. Taurus (bovine; accession #P16436)), MHIT (SEQ ID NO:7) from M. hyorhinis (mycoplasma, accession #M37339), YHIT (SEQ ID NO:8) from S. cerevisiae (accession #Q04344); the Fhit protein is 69% similar to the S. pombe (PAPH1) gene over a length of 109 amino acids. (B) In vitro translation products from recombinant plasmids containing different alleles of the FHIT gene: pFHIT1 with a deletion of noncoding exon 4 (lane 1); pFHIT2 with an insertion of 72 bp between exons 4 and 5 (lane 2); pFHIT3 with a wildtype FHIT lacking exon 1 (lane 3); the pFHIT full-length wildtype gene in Bluescript (lane 4); control reaction, in vitro translation from the pBCAH vector, carrying a portion of the extracellular region of the PTPRG gene (predicted molecular weight 40 kDa) (lane 5).

Figure 5:
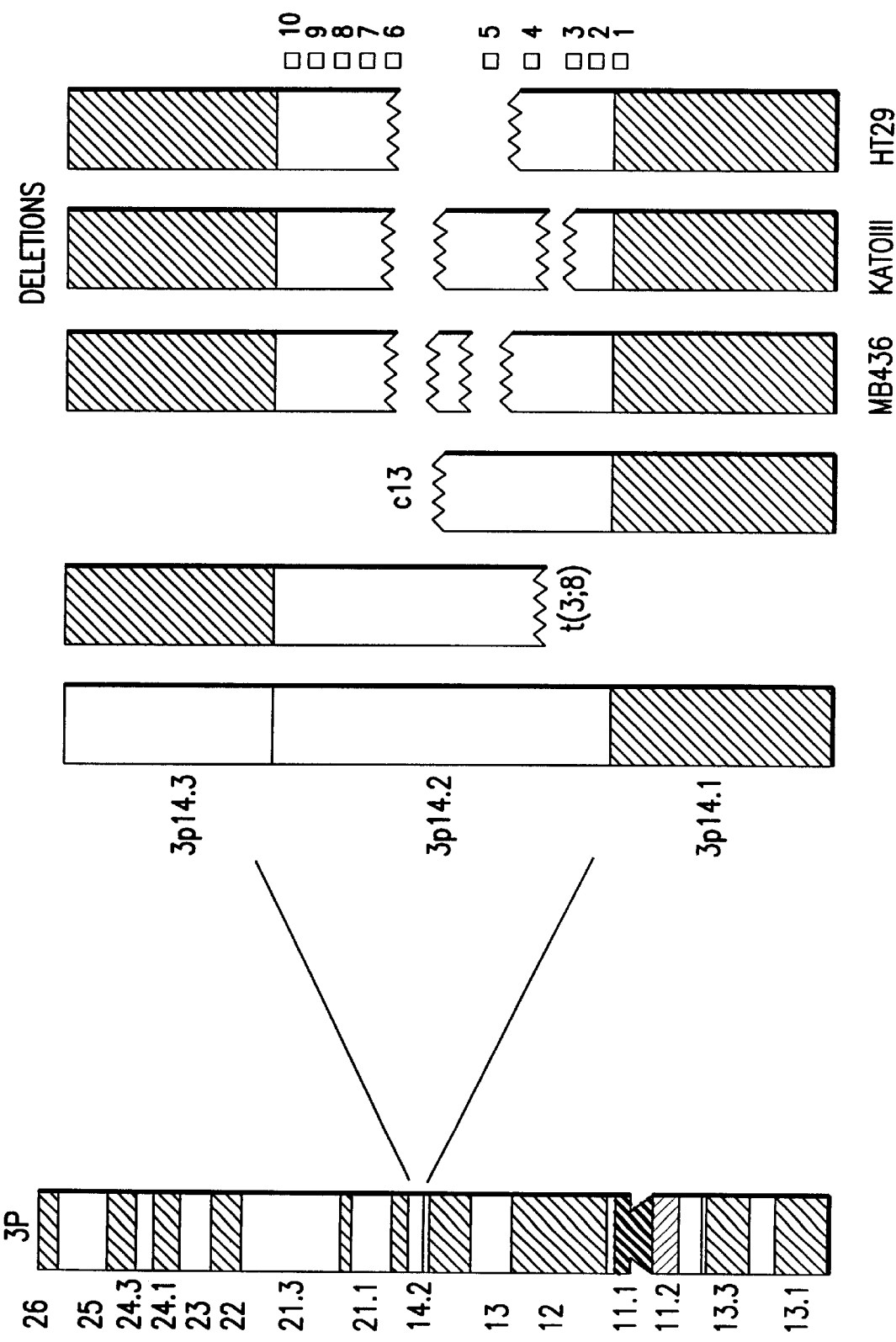

FIG. 5. Organization of the FHIT gene relative to documented chromosome breaks in the 3p14.2 fragile region. One FHIT allele is disrupted in all the translocation carriers of the t(3;8) family, with exons 1, 2 and 3 remaining on the derivative 3 chromosome and exons 4–10, including the entire coding region, being translocated to the derivative 8 chromosome, as illustrated above. The hybrid cell line, c13, with a de novo FRA3B break just telomeric to exon 5, has lost most of the FHIT coding region. The KatoIII cells apparently retain all FHIT exons but encode only an abnormal transcript which lacks exons 4–7 and thus cannot produce Fhit protein. The MB436 and HT29 cells have both lost exon 5 through deletion of different segments of the fragile region.

Figure 6:
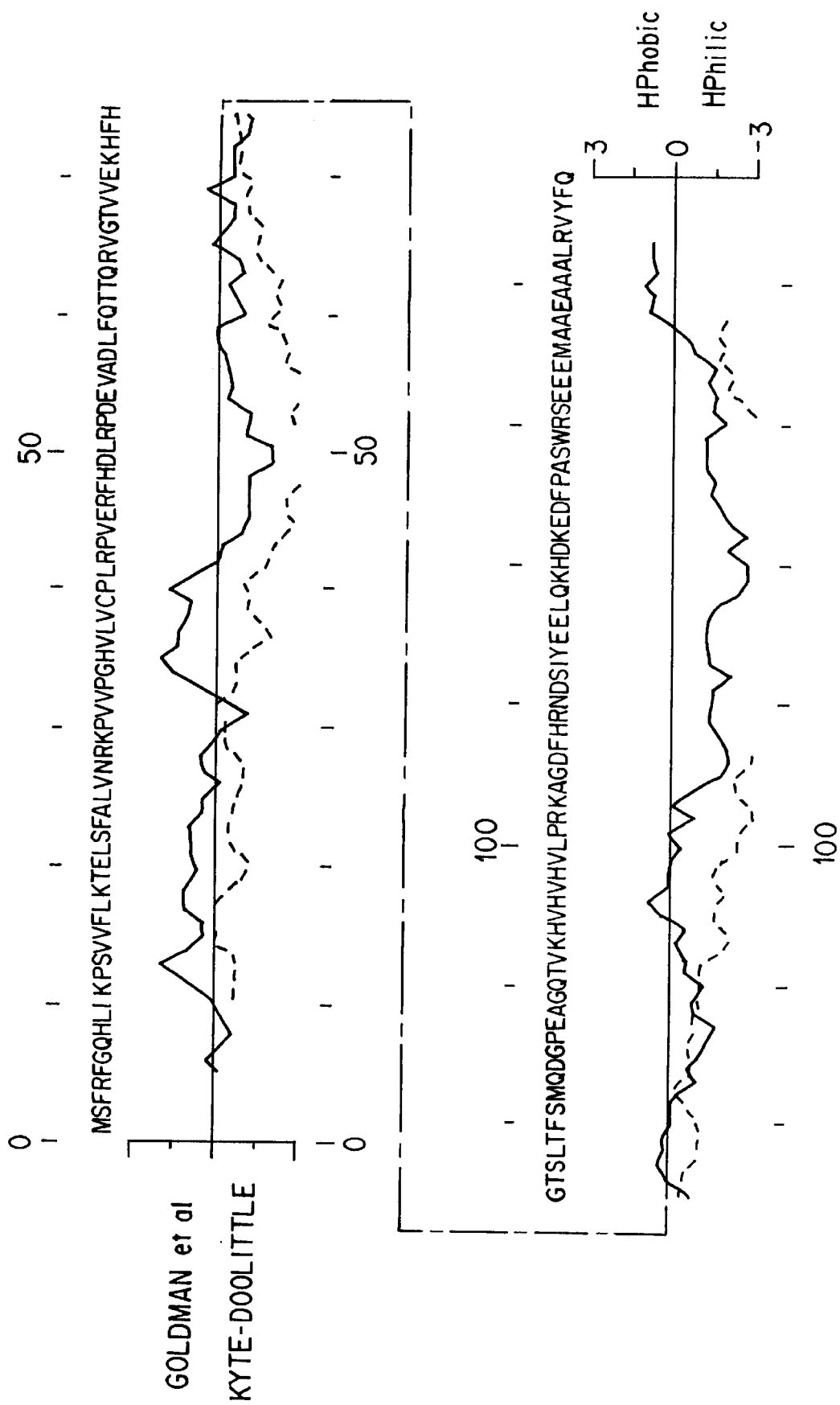

FIG. 6. Hydrophilicity plot of the Fhit deduced protein sequence (SEQ ID NO:2), plotted using the PEPPLOT program of the Wisconsin GCG software for DNA and protein analysis.

FIGS. 7A–7C. Printout of R50713 nucleotide sequence (SEQ ID NO:9) aligned with the FHIT cDNA sequence (cDNA 7F1) (SEQ ID NO:1), and the R11128 nucleotide sequence (SEQ ID NO:77). The FHIT coding region starts at nucleotide 363 and ends at nucleotide 812.

FIG. 8. Translation in all three reading frames, both 5' and 3' directions, of the R50713 EST sequence. 5'3' Frame 1: SEQ ID NOS:10–15 and 76; 5'3' Frame 2: SEQ ID NOS:16–19; 5'3' Frame 3: SEQ ID NOS:20–25; 3'5' Frame 1: SEQ ID NOS:26–31; 3'5' Frame 2: SEQ ID NOS:32–36; 3'5' Frame 3: SEQ ID NOS:37–40.

FIG. 9. Translation in all three reading frames, both 5' and 3' directions, of the R11128 EST sequence. 5'3' Frame 1: SEQ ID NOS:41–44; 5'3' Frame 2: SEQ ID NOS:45–48; 5'3' Frame 3: SEQ ID NOS:49–56; 3'5' Frame 1: SEQ ID NOS:57–58; 3'5' Frame 2: SEQ ID NOS:59–64; 3'5' Frame 3: SEQ ID NOS:65–68.

FIGS. 10A–10D. (A–C) Alignment of yeast (S. pombe) Ap4A hydrolase sequence (U32615) (SEQ ID NO:69) with FHIT cDNA (cDNA 7F1) sequence (SEQ ID NO:1). (D) Result of search for homology stretches between U32615 and cDNA 7F1.

5. DETAILED DESCRIPTION OF THE INVENTION

The present invention relates to nucleotide sequences of FHIT genes and amino acid sequences of their encoded Fhit proteins, as well as derivatives and analogs thereof, and antibodies thereto.

As described by way of example infra, the present inventors have isolated and characterized a human FHIT gene, that is involved in esophageal, gastric, colon, kidney, and other cancers. Mutations in FHIT gene sequences leading to loss of FHIT gene function are associated with cancer.

The present invention further relates to the use of FHIT genes and related nucleic acids and their encoded proteins or derivatives or analogs thereof, and antibodies thereto, in assays for the detection and in treatment/prevention of disease states associated with chromosomal or molecular abnormalities and/or increased expression of FHIT, such as cancer. The present invention also relates to therapeutic compositions comprising Fhit proteins, derivatives or analogs thereof, antibodies thereto, nucleic acids encoding the Fhit proteins, derivatives or analogs, and FHIT antisense nucleic acids.

The FHIT gene sequence can be from one of many different species, including but not limited to, vertebrate, mammalian, bovine, ovine, porcine, equine, rodent and human, in naturally occurring-sequence or in variant form, or from any source, whether natural, synthetic, or recombinant. In a specific embodiment described herein, the FHIT gene sequence is a human sequence. The Fhit protein can be that present in one of many different species, including but not limited to, mammalian, bovine, ovine, porcine, equine, rodent and human, in naturally occurring or variant form, or from any source, whether natural, synthetic, or recombinant. In specific embodiment described herein, the Fhit protein is a human protein.

As defined herein, a Fhit derivative may be a fragment or amino acid variant (e.g., an insertion, substitution and/or deletion derivative) of the Fhit sequence shown in FIG. 2A as long as the fragment or amino acid variant is capable of displaying one or more functional activities associated with a full-length Fhit protein. Such functional activities include but are not limited to antigenicity, i.e., the ability to bind to an anti-Fhit antibody, immunogenicity, i.e., the ability to generate an antibody which is capable of binding a Fhit protein; the ability to inhibit cell proliferation or inhibit tumor growth; the ability to bind (or compete with Fhit for binding) to a substrate for Fhit; ability to multimerize with Fhit; and, possibly, Ap4A or other diadenosine hydrolase activity. The invention provides fragments of a Fhit protein consisting of at least 10 amino acids, or of at least 25 amino acids, or of at least 50 amino acids, or of at least 100 amino acids. Nucleic acids encoding such derivatives or analogs are also within the scope of the invention. A preferred Fhit protein variant is one sharing at least 70% amino acid sequence homology, a particularly preferred Fhit protein variant is one sharing at least 80% amino acid sequence homology and another particularly preferred Fhit protein variant is one sharing at least 90% amino acid sequence homology to the naturally occurring Fhit protein over at least 25, at least 50, at least 75, at least 100, or at least 147 (full-length) contiguous amino acids of the FHIT amino acid sequence. As used herein, amino acid sequence homology refers to amino acid sequences having identical amino acid residues or amino acid sequences containing conservative changes in amino acid residues. In another embodiment, a FHIT homologous protein is one that shares the foregoing percentages of sequences identical with the naturally occurring FHIT protein over the recited lengths of amino acids. Proteins encoded by nucleic acids hybridizable to a FHIT gene under non-stringent, moderately stringent, or stringent conditions are also provided.

The present invention also relates to therapeutic and diagnostic methods and compositions based on Fhit proteins and nucleic acids and anti-Fhit antibodies. The invention provides for treatment or prevention of disorders of overproliferation (e.g., cancer and hyperproliferative disorders) by administering compounds that promote Fhit activity (e.g., Fhit proteins and functionally active analogs and derivatives (including fragments) thereof; nucleic acids encoding the Fhit proteins, analogs, or derivatives, agonists of Fhit).

The invention also provides methods of treatment or prevention of disorders of overproliferation in which the subject is hemizygous for a Fhit dominant-negative mutation by administering compounds to the subject that specifically antagonize, or inhibit, the dominant-negative function of the Fhit mutant gene or protein (e.g., antibodies or Fhit antisense nucleic acids specific to the mutant).

Animal models, diagnostic methods and screening methods for predisposition to disorders are also provided by the invention.

5.1. THE FHIT CODING SEQUENCES

FHIT cDNA, genomic sequences and sequences complementary thereto are FHIT nucleic acids provided by the present invention. In a specific embodiment herein, a FHIT cDNA sequence is provided, thus lacking any introns. Sequences hybridizable thereto, preferably lacking introns, are also provided. Nucleic acids comprising FHIT DNA or RNA exon sequences are also provided; in various embodiments, at least 15, 25 or 50 contiguous nucleotides of FHIT exon sequences are in the nucleic acid. Also included within the scope of the present invention are nucleic acids comprising FHIT cDNA or RNA consisting of at least 8 nucleotides, at least 15 nucleotides, at least 25 nucleotides, at least 50 nucleotides, at least 100 nucleotides, at least 200 nucleotides, or at least 350 nucleotides. In various embodiments, nucleic acids are provided that are less than 2,000, less than 500, less than 275, less than 200, less than 100, or less than 50 bases (or bp, if double-stranded). In various embodiments, the nucleic acids are less than 300 kb, 200 kb, 100 kb, 50 kb, or 10 kb. Nucleic acids can be single-stranded or double-stranded. In specific embodiments, isolated nucleic acids are provided that comprise at least 15 contiguous nucleotides of FHIT coding sequences but which do not comprise all or a portion of any FHIT intron. In a specific embodiment, the nucleic acid comprises at least one FHIT coding exon (exon 5, 6, 7, 8 or 9). In another embodiment, the nucleic acid substantially lacks the PHIT intron between exon 5 and 6, yet contains exon 5 and at least one other FHIT coding exon selected from among exon 6, exon 7, exon 8, and exon 9. In yet another embodiment, the nucleic acid comprises at least one FHIT exon selected from among exon 1, 2, 3, 4 and 5, and contains at least one FHIT exon selected from among exon 6, 7, 8, 9 and 10, and is preferably less than 10 kb in size. In a preferred embodiment the FHIT exon sequences appear in the nucleic acid in the order in which they appear in the genome; in an alternative embodiment, the exon sequences do not appear in the same order. In another embodiment, the nucleic acid comprises all the FHIT exons (exons 1–10) or all the FHIT coding exons (exons 5–9) in contiguous fashion, and thus lacks introns. In yet another specific embodiment, the nucleic acid comprising FHIT gene exon sequences does not contain sequences of a genomic flanking gene (i.e., 5' or 3' to the FHIT gene in the genome). In a specific embodiment herein, a FHIT genomic sequence is provided, thus containing introns.

The invention also provides single-stranded oligonucleotides for use as primers in PCR that amplify a FHIT sequence-containing fragment, e.g., an oligonucleotide having the sequence of a hybridizable portion (at least ~8 nucleotides) of a FHIT gene, and another oligonucleotide having the reverse complement of a downstream sequence in the same strand of the FHIT gene, such that each oligonucleotide primes synthesis in a direction toward the other. The oligonucleotides are preferably in the range of 10–35 nucleotides in length.

The full length cDNA sequence for human FHIT is depicted in FIG. 2A (SEQ ID NO: 1), with the coding region thereof spanning nucleotide numbers 1–441 of FIG. 2A. Sequence analysis of the FHIT cDNA of FIG. 2A reveals an open reading frame of 441 nucleotides, encoding a protein of 147 amino acids (SEQ ID NO:2).

In accordance with the present invention, any polynucleotide sequence which encodes the amino acid sequence of a FHIT gene product can be used to generate recombinant molecules which direct the expression of Fhit. Included within the scope of the present invention are nucleic acids consisting of at least 8 nucleotides that are useful as probes or primers (i.e., a hybridizable portion) in the detection or amplification of FHIT.

In a specific embodiment disclosed herein, the invention relates to the nucleic acid sequence of the human FHIT gene. In a preferred, but not limiting, aspect of the invention, a human FHIT cDNA sequence is that present in plasmid p7Fl as deposited with the ATCC and assigned ATCC Accession Number 69977. Such a sequence can be cloned and sequenced, for example, as described in Section 6, infra. The invention also relates to nucleic acid sequences hybridizable or complementary to the foregoing sequences or equivalent to the foregoing sequences in that the equivalent nucleic acid sequences also encode a protein product displaying Fhit functional activity.

Nucleic acids encoding fragments and derivatives of FHIT are additionally described infra.

The invention also relates to nucleic acids hybridizable to or complementary to the above-described nucleic acids comprising FHIT sequences. In specific aspects, nucleic acids are provided which comprise a sequence complementary to at least 10, 25, 50, 100, or 200 nucleotides or the entire coding region of a FHIT gene. In a specific embodiment, a nucleic acid which is hybridizable to a FHIT nucleic acid, or to a nucleic acid encoding a Fhit derivative, under conditions of low stringency is provided. By way of example and not limitation, procedures using such conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5× SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2× SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which may be used are well known in the art (e.g., as employed for cross-species hybridizations).

In another specific embodiment, a nucleic acid which is hybridizable to a FHIT nucleic acid under conditions of high stringency is provided (see infra).

In a preferred aspect, polymerase chain reaction (PCR) is used to amplify a desired nucleic acid sequence in a library or from a tissue source by using oligonucleotide primers representing known FHIT sequences. Such primers may be used to amplify sequences of interest from an RNA or DNA source, preferably a cDNA library. PCR can be carried out, e.g., by use of a Perkin-Elmer Cetus thermal cycler and Taq polymerase (Gene Amp™). The DNA being amplified can include mRNA or cDNA or genomic DNA from any eukaryotic species. One can choose to synthesize several different degenerate primers, for use in the PCR reactions. It is also possible to vary the stringency of hybridization conditions used in priming the PCR reactions, to allow for greater or lesser degrees of nucleotide sequence homology between the FHIT gene being cloned and the known FHIT gene. Other means for primer dependent amplification of nucleic acids are known to those of skill in the art and can be used.

After successful amplification of a segment of a FHIT gene (e.g., an allelic or polymorphic variant or species homolog of a known FHIT gene) that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding Fhit proteins may be identified. Alternatively, the FHIT gene of the present invention may be isolated through an exon trapping system, using genomic DNA (Nehls et al., 1994, Oncogene 9(8):2169–2175; Verna et al., 1993, Nucleic Acids Res. 21(22):5198:5202; Auch et al., 1990, Nucleic Acids Res. 18(22):6743–6744).

Potentially, any eukaryotic cell can serve as the nucleic acid source for the molecular cloning of the FHIT gene. The nucleic acid sequences encoding FHIT can be isolated from, for example, human, porcine, bovine, feline, avian, equine, canine, rodent, as well as additional primate sources. The DNA may be obtained by standard procedures known in the art from, for example, cloned DNA (e.g., a DNA "library"), by chemical synthesis, by cDNA cloning, or by the cloning of genomic DNA, or fragments thereof, purified from a desired cell. (See, for example, Sambrook et al., 1989, Molecular Cloning, A Laboratory Manual, 2d Ed., Cold Spring Harbor Laboratory Press, Cold Spring Harbor, New York; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions while clones derived from cDNA will contain only FHIT exon sequences. Whatever the source, the gene should be molecularly cloned into a suitable vector for propagation of the gene. In a particular embodiment, a preferred source of nucleic acid for the isolation of FHIT gene sequences is from kidney or stomach or lung cells.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, a FHIT gene of the present invention or its specific RNA, or a fragment thereof, such as a probe or primer, may be isolated and labeled and then used in hybridization assays to detect a generated FHIT gene (Benton, W. and Davis, R., 1977, Science 196:180; Grunstein, M. And Hogness, D., 1975, Proc. Natl. Acad. Sci. USA 72:3961). Those DNA fragments sharing substantial sequence homology to the probe will hybridize under high stringency conditions. The phrase "high stringency conditions" as used herein refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5× SSC (0.75 M NaCl, 0.075 M sodium pyrophosphate, 5× Denhardt's solution, sonicated salmon sperm DNA (50 g/ml), 0.1% SDS, and 10% dextran sulfate at 42° C., with washes at 42° C. in 0.2× SSC and 0.1% SDS.

It is also possible to identify the appropriate fragment by restriction enzyme digestion(s) and comparison of fragment sizes with those expected according to a known restriction map. Further selection can be carried out on the basis of the properties of the gene. Alternatively, the presence of the gene may be detected by assays based on the physical, chemical, or immunological properties of its expressed product. For example, cDNA clones, or genomic DNA clones which hybrid-select the proper mRNAs, can be selected which produce a protein that has similar or identical electrophoretic migration, isolectric focusing behavior, proteolytic digestion maps, binding activity or antigenic properties as known for FHIT. Alternatively, the FHIT protein may be identified by binding of labeled antibody to the putatively FHIT expressing clones, e.g., in an ELISA (enzyme-linked immunosorbent assay)-type procedure.

The FHIT gene can also be identified by mRNA selection by nucleic acid hybridization followed by in vitro translation. In this procedure, fragments are used to isolate complementary mRNAs by hybridization. Such DNA fragments may represent available, purified FHIT DNA of another FHIT gene. Immunoprecipitation analysis or functional assays of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against FHIT protein. A radiolabelled FHIT cDNA can be synthesized using the selected mRNA (from the adsorbed polysomes) as a template. The radiolabelled mRNA or cDNA may then be used as a probe to identify the FHIT DNA fragments from among other genomic DNA fragments.

Alternatives to isolating the FHIT genomic DNA include, but are not limited to, chemically synthesizing the gene sequence itself from a known sequence or making cDNA to the mRNA which encodes the FHIT protein. For example, RNA useful in cDNA cloning of the FHIT gene can be isolated from cells which express FHIT, e.g., kidney or stomach or lung cells. Other methods are known to those of skill in the art and are within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives or the Bluescript vector (Stratagene). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and FHIT gene may be modified by homopolymeric tailing. Recombinant molecules can be introduced into host cells via transformation, transfection, infection, electroporation, or other methods known to those of skill in the art, so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated FHIT gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

Oligonucleotides containing a portion of the FHIT coding or non-coding sequences, or which encode a portion of the FHIT protein (e.g., primers for use in PCR) can be synthesized by standard methods commonly known in the art. Such oligonucleotides preferably have a size in the range of 8 to 25 nucleotides. In a specific embodiment herein, such oligonucleotides have a size in the range of 15 to 25 nucleotides or 15 to 35 nucleotides.

The FHIT sequences provided by the instant invention include those nucleotide sequences encoding substantially the same amino acid sequences as found in native Fhit proteins, and those encoded amino acid sequences with functionally equivalent amino acids, as well as those encoding other Fhit derivatives or analogs, as described infra for Fhit derivatives and analogs.

5.2. EXPRESSION OF THE FHIT GENE

In accordance with the present invention, nucleotide sequences coding for a FHIT protein, derivative, e.g. fragment, or analog thereof, can be inserted into an appropriate expression vector, i.e., a vector which contains the necessary elements for the transcription and translation of the inserted protein-coding sequence, for the generation of recombinant DNA molecules that direct the expression of a FHIT protein. Such FHIT polynucleotide sequences, as well as other polynucleotides or their complements, may also be used in nucleic acid hybridization assays, Southern and Northern blot analysis, etc. In a specific embodiment, a human FHIT gene, or a sequence encoding a functionally active portion of a human FHIT gene is expressed. In yet another embodiment, a derivative or fragment of a human FHIT gene is expressed.

Due to the inherent degeneracy of the genetic code, other DNA sequences which encode substantially the same or a functionally equivalent FHIT amino acid sequence, is within the scope of the invention. Such DNA sequences include those which are capable of hybridizing to the human FHIT sequence under stringent conditions.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within an FHIT sequence, which result in a silent change thus producing a functionally equivalent FHIT protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

The DNA sequences of the invention may be engineered in order to alter a FHIT coding sequence for a variety of ends including but not limited to alterations which modify processing and expression of the gene product. For example, mutations may be introduced using techniques which are well known in the art, e.g., site-directed mutagenesis, to insert new restriction sites, etc.

In another embodiment of the invention, a FHIT gene sequence or a derivative thereof is ligated to a non-FHIT sequence to encode a chimeric fusion protein. A fusion protein may also be engineered to contain a cleavage site located between a FHIT sequence and the non-FHIT protein sequence, so that the FHIT protein may be cleaved away from the non-FHIT moiety. In a specific embodiment, the FHIT amino acid sequence present in the fusion protein consists of at least 10 contiguous amino acids, at least 25 contiguous amino acids, at least 50 contiguous amino acids, at least 75 contiguous amino acids, at least 100 contiguous amino acids, or at least 147 amino acids (full-length) of the Fhit protein sequence.

In an alternate embodiment of the invention, the coding sequence of a FHIT is synthesized in whole or in part, using chemical methods well known in the art. See, for example, Caruthers et al., 1980, Nuc. Acids Res. Symp. Ser. 7:215–233; Crea and Horn, 1980, Nuc. Acids Res. 9(10):2331; Matteucci and Caruthers, 1980, Tetrahedron Letters 21:719; and Chow and Kempe, 1981, Nuc. Acids Res. 9(12):2807–2817. Alternatively, the protein itself could be produced using chemical methods to synthesize an FHIT amino acid sequence in whole or in part. For example, peptides can be synthesized by solid phase techniques, cleaved from the resin, and purified by preparative high performance liquid chromatography. (e.g., see Creighton, 1983, Proteins Structures And Molecular Principles, W. H. Freeman and Co., N.Y. pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49.

In order to express a biologically active FHIT protein or derivative thereof, a polynucleotide sequence encoding a FHIT protein, or a derivative thereof, is inserted into an appropriate expression vector, i.e., a vector which contains the necessary elements for the transcription and translation of the inserted coding sequence. The FHIT gene products as well as host cells or cell lines transfected or transformed with recombinant FHIT expression vectors can be used for a variety of purposes. These include but are not limited to generating antibodies (i.e., monoclonal or polyclonal) that immunospecifically bind a FHIT protein. Anti-FHIT antibodies can be used in detecting or measuring levels of a FHIT protein in patient samples.

5.2.1. EXPRESSION SYSTEMS

Methods which are well known to those skilled in the art can be used to construct expression vectors containing a FHIT coding sequence and appropriate transcriptional/translational control signals. These methods include in vitro recombinant DNA techniques, synthetic techniques and in vivo recombination/genetic recombination. See, for example, the techniques described in Sambrook et al., 1989, Molecular Cloning, A Laboratory Manual 2d ed., Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express a FHIT coding sequence. These include but are not limited to microorganisms such as bacteria transformed with recombinant bacteriophage DNA, plasmid DNA or cosmid DNA expression vectors containing an FHIT coding sequence; yeast transformed with recombinant yeast expression vectors containing an FHIT coding sequence; insect cell systems infected with recombinant virus expression vectors (e.g., baculovirus) containing an FHIT coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing an FHIT coding sequence; or animal cell systems. The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of an FHIT DNA, SV40-, BPV- and EBV-based vectors may be used with an appropriate selectable marker.

In bacterial systems, a number of expression vectors may be advantageously selected depending upon the use intended for the FHIT protein expressed. For example, when large quantities of FHIT protein are to be produced for the generation of antibodies, vectors which direct the expression of high levels of fusion protein products that are readily purified may be desirable. Such vectors include but are not limited to the *E. coli* expression vector pUR278 (Ruther et al., 1983, EMBO J. 2:1791), in which the FHIT coding sequence may be ligated into the vector in frame with the lac Z coding region so that a hybrid AS-lac Z protein is produced; pIN vectors (Inouye & Inouye, 1985, Nucleic acids Res. 13:3101–3109; Van Heeke & Schuster, 1989, J. Biol. Chem. 264:55035509); and the like. pGEX vectors may also be used to express foreign polypeptides as fusion proteins with glutathione S-transferase (GST) (Smith and Johnson, 1988, Gene 7:31–40). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Ed. Wu & Grossman, 1987, Acad. Press, N.Y. 153:516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y. 152:673–684; and The Molecular Biology of the Yeast Saccharomyces, 1982, Eds. Strathern et al., Cold Spring Harbor Press, Vols. I and II.

In cases where plant expression vectors are used, the expression of an FHIT coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

An alternative expression system which could be used to express a FHIT gene is an insect system. In one such system, *Autographa californica* nuclear polyhedrosis virus (AcNPV) is used as a vector to express foreign genes. The virus grows in *Spodoptera frugiperda* cells. A FHIT coding sequence may be cloned into non-essential regions (for example the polyhedrin gene) of the virus and placed under control of an AcNPV promoter (for example, the polyhedrin promoter). Successful insertion of a FHIT coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Virol. 46:584; Smith, U.S. Pat. No. 4,215,051).

In mammalian host cells, a number of viral based expression systems may be utilized. In cases where an adenovirus is used as an expression vector, a FHIT coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a FHIT in infected hosts. (e.g., see Logan & Shenk, 1984, Proc. Natl. Acad. Sci. USA 81:3655–3659). Alternatively, the vaccinia 7.5 K promoter may be used. (See, e.g., Mackett et al., 1982, Proc. Natl. Acad. Sci. USA 79:7415–7419; Mackett et al., 1984, J. Virol. 49:857–864; Panicali et al., 1982, Proc. Natl. Acad. Sci. USA 79:4927–4931).

Specific initiation signals may also be required for efficient translation of an inserted FHIT coding sequences. These signals include the ATG initiation codon and adjacent sequences. In cases where an entire FHIT gene, including its own initiation codon and adjacent sequences, is inserted into the appropriate expression vector, no additional translational control signals may be needed. However, in cases where only a portion of a FHIT coding sequence is inserted, lacking the 5' end, exogenous translational control signals, including the ATG initiation codon, must be provided. Furthermore, the initiation codon must be in phase with the reading frame of a FHIT coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., phosphorylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express a FHIT protein may be engineered. Rather than using expression vectors which contain viral origins of replication, host cells can be transformed with FHIT DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express a FHIT protein. The present invention provides a method for producing a recombinant FHIT protein comprising culturing a host cell transformed with a recombinant expression vector encoding a FHIT protein such that the FHIT protein is expressed by the cell and recovering the expressed FHIT protein.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt- cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147). Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue, L., 1987, In: Current Communications in Molecular Biology, Cold Spring Harbor Laboratory, Ed.).

5.2.2. IDENTIFICATION OF TRANSFECTANTS OR TRANSFORMANTS THAT EXPRESS FHIT

The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of FHIT mRNA transcripts in the host cell; and (d) detection of the gene product as measured by immunoassay or by its biological activity.

In the first approach, the presence of the FHIT coding sequence inserted in the expression vector can be detected by DNA-DNA or DNA-RNA hybridization using probes comprising nucleotide sequences that are homologous to the FHIT coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the human FHIT coding sequence is inserted within a marker gene sequence of the vector, recombinant cells containing the FHIT coding sequence can be identified by the absence of the marker gene function. Alternatively, a marker gene can be placed in tandem with a FHIT sequence under the control of the same or different promoter used to control the expression of the FHIT coding sequence. Expression of the marker in response to induction or selection indicates expression of the FHIT coding sequence.

In the third approach, transcriptional activity of a FHIT gene can be assessed by hybridization assays. For example, RNA can be isolated and analyzed by Northern blot using a probe having sequence homology to a FHIT coding sequence or transcribed noncoding sequence or particular portions thereof. Alternatively, total nucleic acid of the host cell may be extracted and quantitatively assayed for hybridization to such probes.

In the fourth approach, the levels of a FHIT protein product can be assessed immunologically, for example by Western blots, immunoassays such as radioimmunoprecipitation, enzyme-linked immunoassays and the like.

5.3. PURIFICATION OF THE EXPRESSED GENE PRODUCT

Once a recombinant which expresses the FHIT gene sequence is identified, the gene product can be analyzed. This is achieved by assays based on the physical or functional properties of the product, including radioactive labelling of the product followed by analysis by gel electrophoresis, immunoassay, or other detection methods known to those of skill in the art.

Once the FHIT protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay.

Alternatively, once a FHIT protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller et al., 1984, Nature 310:105–111).

In a specific embodiment of the present invention, such FHIT proteins, whether produced by recombinant DNA techniques or by chemical synthetic methods, include but are not limited to those containing, as a primary amino acid sequence, all or part of the amino acid sequence substantially as depicted in FIG. 2A (SEQ ID NO:2), as well as fragments and other derivatives, and analogs thereof.

5.4. GENERATION OF ANTIBODIES TO Fhit

According to the invention, Fhit protein, its fragments or other derivatives, or analogs thereof, may be used as an immunogen to generate antibodies which recognize such an immunogen. Such antibodies include but are not limited to polyclonal, monoclonal, chimeric, single chain, Fab fragments, and an Fab expression library. In a specific embodiment, antibodies to a human Fhit protein are produced.

Various procedures known in the art may be used for the production of polyclonal antibodies to a Fhit protein or derivative or analog. For the production of antibody, various host animals can be immunized by injection with the native Fhit protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a Fhit protein sequence or analog thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. USA 80:2026–2030) or by transforming human B cells with EBV virus in vitro (Cole et al., 1985, in Monoclonal Antibodies and Cancer Therapy, Alan R. Liss, pp. 77–96). In fact, according to the invention, techniques developed for the production of "chimeric antibodies" (Morrison et al., 1984, Proc. Natl. Acad. Sci. USA 81:6851–6855; Neuberger et al., 1984, Nature 312:604–608; Takeda et al., 1985, Nature 314:452–454) by splicing the genes from a mouse antibody molecule specific for FHIT together with genes from a human antibody molecule of appropriate biological activity can be used; such antibodies are within the scope of this invention.

According to the invention, techniques described for the production of single chain antibodies (U.S. Pat. No. 4,946,778) can be adapted to produce Fhit-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for Fhit proteins, derivatives, or analogs.

In a specific embodiment, a molecule comprising a fragment of the Fhit protein is used as an immunogen. For example, since hydrophilic regions are believed most likely to contain antigenic determinants, a peptide corresponding to or containing a hydrophilic portion of a Fhit protein is preferably used as immunogen.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay). For example, to select antibodies which recognize a specific domain of a Fhit protein, one may assay generated hybridomas for a product which binds to a Fhit fragment containing such domain. For selection of an antibody specific to human Fhit, one can select on the basis of positive binding to human Fhit and a lack of binding to, for example, mouse Fhit.

The foregoing antibodies can be used in methods known in the art relating to the localization and activity of the protein sequences of the invention, e.g., for imaging these proteins, measuring levels thereof in appropriate physiological samples, in diagnostic methods, etc.

5.5. STRUCTURE OF THE FHIT GENE AND PROTEIN

The structure of the FHIT gene and protein can be analyzed by various methods known in the art.

5.5.1. GENETIC ANALYSIS

The cloned DNA or cDNA corresponding to the FHIT gene can be analyzed by methods including but not limited to Southern hybridization (Southern, E. M., 1975, J. Mol. Biol. 98:5035 517), Northern hybridization (see, e.g., Freeman et al., 1983, Proc. Natl. Acad. Sci. USA 80:4094–4098), restriction endonuclease mapping (Maniatis, T., 1982, Molecular Cloning, A Laboratory, Cold Spring Harbor, New York), and DNA sequence analysis. Polymerase chain reaction (PCR; U.S. Pat. Nos. 4,683,202, 4,683,195, and 4,889,818; Gyllenstein et al., 1988, Proc. Natl. Acad. Sci. USA 85:7652–7656; Ochman et al., 1988, Genetics 120:621–623; Loh et al., 1989, Science 243:217–220) followed by Southern hybridization with a FHIT-specific probe can allow the detection of the FHIT gene in DNA from various cell types. In one embodiment, Southern hybridization may be used to determine the genetic linkage of FHIT. PCR followed by hybridization assay can also be used to detect or measure FHIT RNA or 3p14.2 chromosomal or molecular abnormalities. Northern hybridization analysis can be used to determine the expression levels of the FHIT gene. Other assays are described in Section 5.11. Various cell types, at various states of development or activity can be tested for FHIT expression. The stringency of the hybridization conditions for both Southern and Northern hybridization, or dot blots, can be manipulated to ensure detection of nucleic acids with the desired degree of relatedness to the specific FHIT probe used.

Restriction endonuclease mapping can be used to roughly determine the genetic structure of the FHIT gene. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499–560), the Sanger dideoxy method (Sanger et al., 1977, Proc. Natl. Acad. Sci. USA 74:5463), the use of T7 DNA polymerase (Tabor and Richardson, U.S. Pat. No. 4,795,699), or use of an automated DNA sequenator (e.g., Applied Biosystems, Foster City, CA).

The cDNA sequence of a representative FHIT gene comprises the sequence substantially as depicted in FIG. 2A (SEQ ID NO: 1), and described in Section 6, infra.

5.5.2. PROTEIN ANALYSIS

The amino acid sequence of the Fhit protein can be derived by deduction from the DNA sequence, or alternatively, by direct sequencing of the protein, e.g., with an automated amino acid sequencer. The amino acid sequence of a representative Fhit protein comprises the sequence substantially as depicted in FIG. 2A (SEQ ID NO: 2), and detailed in Section 6, infra, with the representative mature protein that is shown by amino acid numbers 1–147.

The Fhit protein sequence can be further characterized by a hydrophilicity analysis (Hopp, T. and Woods, K., 1981, Proc. Natl. Acad. Sci. USA 78:3824). A hydrophilicity profile can be used to identify the hydrophobic and hydrophilic regions of the Fhit protein and the corresponding regions of the gene sequence which encode such regions.

Secondary structural analysis (Chou, P. and Fasman, G., 1974, Biochemistry 13:222) can also be done, to identify regions of the Fhit protein that assume specific secondary structures.

Manipulation, translation, and secondary structure prediction, as well as open reading frame prediction and plotting, can also be accomplished using computer software programs available in the art.

Other methods of structural analysis can also be employed. These include but are not limited to X-ray crystallography (Engstom, A., 1974, Biochem. Exp. Biol. 11:713) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, New York).

5.6. Fhit PROTEINS. DERIVATIVES AND ANALOGS

The invention further relates to Fhit proteins, and derivatives (including but not limited to fragments) and analogs of Fhit proteins. Nucleic acids encoding Fhit protein derivatives and protein analogs are also provided. Molecules comprising Fhit proteins or derivatives are also provided. In one embodiment, the Fhit proteins are encoded by the Fhit nucleic acids described in Section 5.1 supra. In particular aspects, the proteins, derivatives, or analogs are of Fhit proteins of animals.

The production and use of derivatives and analogs related to Fhit are within the scope of the present invention. In a specific embodiment, the derivative or analog is functionally active, i.e., capable of exhibiting one or more functional activities associated with a full-length, wild-type Fhit protein. As one example, such derivatives or analogs which have the desired immunogenicity or antigenicity can be used, for example, in immunoassays, for immunization, for inhibition of Fhit activity, etc. As another example, such derivatives or analogs which have hydrolase activity are provided. Derivatives or analogs that retain, or alternatively lack or inhibit, a desired Fhit property of interest (e.g., inhibition of cell proliferation, tumor inhibition), can be used as inducers, or inhibitors, respectively, of such property and its physiological correlates. A specific embodiment relates to a Fhit fragment that can be bound by an anti-Fhit antibody. Derivatives or analogs of Fhit can be tested for the desired activity by procedures known in the art, including but not limited to the assays described infra.

In particular, Fhit derivatives can be made by altering FHIT sequences by substitutions, additions or deletions that provide for functionally equivalent molecules. Due to the degeneracy of nucleotide coding sequences, other DNA sequences which encode substantially the same amino acid sequence as a FHIT gene may be used in the practice of the present invention. These include but are not limited to nucleotide sequences comprising all or portions of FHIT genes which are altered by the substitution of different codons that encode a functionally equivalent amino acid residue within the sequence, thus producing a silent change. Likewise, the Fhit derivatives of the invention include, but are not limited to, those containing, as a primary amino acid sequence, all or part of the amino acid sequence of a Fhit protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or comprising a fragment of a Fhit protein consisting of at least 10 (continuous) amino acids of the Fhit protein is provided. In other embodiments, the fragment consists of at least 20 or 50 amino acids of the Fhit protein. In specific embodiments, such fragments are not larger than 35, 100 or 140 amino acids. Derivatives or analogs of Fhit include but are not limited to those molecules comprising regions that are substantially homologous to Fhit or fragments thereof (e.g., in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a coding FHIT sequence, under stringent, moderately stringent, or nonstringent conditions.

The Fhit derivatives and analogs of the invention can be produced by various methods known in the art. The manipulations which result in their production can occur at the gene or protein level. For example, the cloned FHIT gene sequence can be modified by any of numerous strategies known in the art (Maniatis, T., 1990, Molecular Cloning, A Laboratory Manual, 2d ed., Cold Spring Harbor Laboratory, Cold Spring Harbor, New York). The sequence can be cleaved at appropriate sites with restriction endonuclease(s), followed by further enzymatic modification if desired, isolated, and ligated in vitro. In the production of the gene encoding a derivative or analog of Fhit, care should be taken to ensure that the modified gene remains within the same translational reading frame as Fhit, uninterrupted by translational stop signals, in the gene region where the desired Fhit activity is encoded.

Additionally, the Fhit-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), etc.

Manipulations of the Fhit sequence may also be made at the protein level. Included within the scope of the invention are Fhit protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives of Fhit can be chemically synthesized. For example, a peptide corresponding to a portion of a Fhit protein which comprises the desired domain (see Section 5.6.1), or which mediates the desired activity in vitro, can be synthesized by use of a peptide synthesizer. Furthermore, if desired, nonclassical amino acids or chemical amino acid analogs can be introduced as a substitution or addition into the Fhit sequence. Nonclassical amino acids include but are not limited to the D-isomers of the common amino acids, α-amino isobutyric acid, 4amino-butyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, the Fhit derivative is a chimeric, or fusion, protein comprising a Fhit protein or fragment thereof (preferably consisting of at least a domain or motif of the Fhit protein, or at least 10 amino acids of the Fhit protein) joined at its amino- or carboxy-terminus via a peptide bond to an amino acid sequence of a different protein. In one embodiment, such a chimeric protein is produced by recombinant expression of a nucleic acid encoding the protein (comprising a Fhit-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of FHIT fused to any heterologous protein-encoding sequences may be constructed.

In another specific embodiment, the Fhit derivative is a molecule comprising a region of homology with a Fhit protein. By way of example, in various embodiments, a first protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region or when compared to an aligned sequence of the second region that has been aligned by a computer homology program known in the art. For example, a molecule can comprise one or more regions homologous to a Fhit domain (see Section 5.6.1) or a portion thereof or a full-length Fhit protein.

5.7. ASSAYS OF Fhit PROTEINS, DERIVATIVES AND ANALOGS

The functional activity of Fhit proteins, derivatives and analogs can be assayed by various methods.

For example, in one embodiment, where one is assaying for the ability to bind or compete with wild-type Fhit for binding to anti-Fhit antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

In another embodiment, where a Fhit-binding protein is identified, the binding can be assayed, e.g., by means well-known in the art.

In another embodiment, should a Fhit protein have hydrolase activity, hydrolase assays can be used to measure Fhit hydrolase activity. Such assays can be carried out by methods well known in the art.

In addition, assays known in the art can be used to detect or measure the ability to inhibit cell proliferation, in vitro or in vivo. Other methods will be known to the skilled artisan and are within the scope of the invention.

5.8. THERAPEUTIC USES: TREATMENT AND PREVENTION OF DISORDERS INVOLVING OVERPROLIFERATION OF CELLS

The invention provides for treatment or prevention of various diseases and disorders by administration of a therapeutic compound (termed herein "Therapeutic"). Such "Therapeutics" include but are not limited to: Fhit proteins and analogs and derivatives (including fragments) thereof (e.g., as described hereinabove); antibodies thereto (as described hereinabove); nucleic acids encoding the Fhit proteins, analogs, or derivatives (e.g., as described hereinabove); and Fhit agonists, and antagonists of mutant FHIT genes or proteins (e.g., antibodies or antisense nucleic acids). In a preferred embodiment, disorders involving cell overproliferation are treated or prevented by administration of a Therapeutic that promotes Fhit function. The above is described in detail in the subsections below.

Generally, administration of products of a species origin or species reactivity (in the case of antibodies) that is the same species as that of the patient is preferred. Thus, in a preferred embodiment, a human Fhit protein, derivative, or analog, or nucleic acid, or an antibody to a human Fhit protein or human FHIT antisense nucleic acid, is therapeutically or prophylactically administered to a human patient.

Additional descriptions and sources of Therapeutics that can be used according to the invention are found in Sections 5.1 through 5.7 herein.

A FHIT polynucleotide and its Fhit protein product can be used for therapeutic/ prophylactic purposes for diseases involving cell overproliferation, as well as other disorders associated with chromosomal translocations or inversions or molecular abnormalities associated with the FHIT locus, and/or decreased expression of wild-type FHIT RNA or protein and/or expression of a mutant FHIT RNA or protein and/or expression of a mutant FHIT RNA or protein. A FHIT polynucleotide, and its FHIT protein product, may be used for therapeutic/prophylactic purposes alone or in combination with other therapeutics useful in the treatment of cancer and hyperproliferative or dysproliferative disorders.

Diseases and disorders involving cell overproliferation are treated or prevented by administration of a Therapeutic that promotes (i.e., increases or supplies) Fhit function. Examples of such a Therapeutic include but are not limited to Fhit proteins, derivatives, or fragments that are functionally active, particularly that are active in inhibiting cell proliferation (e.g., as demonstrated in in vitro assays or in animal models), and nucleic acids encoding a Fhit protein or functionally active derivative or fragment thereof (e.g., for use in gene therapy). Other Therapeutics that can be used, e.g., Fhit agonists, can be identified using in vitro assays or animal models, examples of which are described infra.

In specific embodiments, Therapeutics that promote Fhit function are administered therapeutically (including prophylactically): (1) in diseases or disorders involving an absence or decreased (relative to normal or desired) level of Fhit functional protein or of Fhit function, for example, in patients where Fhit protein is lacking, genetically defective, biologically inactive or underactive, or underexpressed; or (2) in diseases or disorders wherein in vitro (or in vivo) assays indicate the utility of Fhit agonist administration. The absence or decreased level in Fhit protein or function can be readily detected, e.g., by obtaining a patient tissue sample (e.g., from biopsy tissue) and assaying it in vitro for RNA or protein levels, structure and/or activity of the expressed Fhit RNA or protein (see Section 5.11 infra re assays used in diagnosis). Many methods standard in the art can be thus employed, including but not limited to immunoassays to detect and/or visualize Fhit protein (e.g., Western blot, immunoprecipitation followed by sodium dodecyl sulfate polyacrylamide gel electrophoresis, immunocytochemistry, etc.) and/or hybridization assays to detect Fhit expression by detecting and/or visualizing Fhit mRNA or cDNA (e.g., Northern assays, dot blots, in situ hybridization, and preferably those assays described in Section 5.11), etc.

Diseases and disorders involving cell overproliferation that can be treated or prevented include but are not limited to malignancies, premalignant conditions (e.g., hyperplasia, metaplasia, dysplasia), benign tumors, hyperproliferative disorders, benign dysproliferative disorders, etc. Examples of these are detailed below.

5.8.1. MALIGNANCIES

Malignancies and related disorders that can be treated or prevented by administration of a Therapeutic that promotes Fhit function (e.g., a full-length Fhit protein or functional derivative thereof or nucleic acid encoding the foregoing) include but are not limited to those listed in Table 1 (for a review of such disorders, see Fishman et al., 1985, Medicine, 2d Ed., J. B. Lippincott Co., Philadelphia):

TABLE 1

MALIGNANCIES AND RELATED DISORDERS

Leukemia acute leukemia
acute lymphocytic leukemia
acute myelocytic leukemia
myeloblastic
promyelocytic
myelomonocytic
monocytic
erythroleukemia
chronic leukemia
chronic myelocytic (granulocytic) leukemia
chronic lymphocytic leukemia
Polycythemia vera Lymphoma Hodgkin's disease
non-Hodgkin's disease
Multiple myeloma
Waldenström's macroglobulinemia
Heavy chain disease Solid tumors sarcomas and carcinomas
fibrosarcoma
myxosarcoma
liposarcoma
chondrosarcoma
osteogenic sarcoma
osteosarcoma
chordoma
angiosarcoma
endotheliosarcoma
lymphangiosarcoma
lymphangioendotheliosarcoma
synovioma
mesothelioma
Ewing's tumor
leiomyosarcoma
rhabdomyosarcoma
colon carcinoma
colorectal carcinoma
pancreatic cancer
breast cancer
ovarian cancer
prostate cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
testicular tumor
lung carcinoma

TABLE 1-continued

MALIGNANCIES AND RELATED DISORDERS
  small cell lung carcinoma
  bladder carcinoma
  epithelial carcinoma
  glioma
  astrocytoma
  medulloblastoma
  craniopharyngioma
  ependymoma
  pinealoma
  hemangioblastoma
  acoustic neuroma
  oligodendroglioma
  menangioma
  melanoma
  neuroblastoma
  retinoblastoma
  nasopharyngeal carcinoma
  esophageal carcinoma In a specific embodiment, digestive tract tumors are treated or prevented, including but not limited to esophageal, stomach, colon, and colorectal cancers. In another specific embodiment, airway cancers such as lung cancers (e.g., small cell lung carcinoma) and nasopharyngeal carcinoma are treated or prevented. In yet other specific embodiments, malignancy or dysproliferative changes (such as metaplasias and dysplasias), or hyperproliferative disorders, are treated or prevented in the head, neck, cervix, kidney, stomach, skin, ovary, bladder, breast, colon, lung, or uterus. In other specific embodiments, sarcoma, or leukemia is treated or prevented. In another particular embodiment, osteosarcoma or renal cell carcinoma is treated or prevented.

5.8.2. PREMALIGNANT CONDITIONS

The Therapeutics of the invention that promote Fhit activity can also be administered to treat premalignant conditions and to prevent progression to a neoplastic or malignant state, including but not limited to those disorders listed in Table 1. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W. B. Saunders Co., Philadelphia, pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

In a preferred embodiment of the invention, a patient in whose DNA is detected a mutation in the FHIT gene, particularly a deletion, and most particularly a homozygous mutation, is thereby determined to have a predisposition to cancer and is treated by administration of a Fhit protein or functional derivative thereof or nucleic acid encoding the same (gene therapy).

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic that promotes Fhit function. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, *Basic Pathology*, 2d Ed., W. B. Saunders Co., Philadelphia, pp. 112–113) etc.)

In a specific embodiment, a Therapeutic of the invention is administered to a human patient to prevent progression to breast, colon, lung, stomach or uterine cancer, or melanoma or sarcoma.

5.8.3. HYPERPROLIFERATIVE AND DYSPROLIFERATIVE DISORDERS

In another embodiment of the invention, a Therapeutic that promotes Fhit activity is used to treat or prevent hyperproliferative or benign dysproliferative disorders. Specific embodiments are directed to treatment or prevention of benign tumors, fibrocystic conditions, and tissue hypertrophy (e.g., prostatic hyperplasia). In specific embodiments, a patient having an intestinal polyp, colon polyp, or esophageal dysplasia is treated by administration of a Therapeutic.

5.8.4. GENE THERAPY

In a specific embodiment, nucleic acids comprising a sequence encoding a Fhit protein or functional derivative thereof, are administered to promote Fhit function, by way of gene therapy. Gene therapy refers to therapy performed by the administration of a nucleic acid to a subject.

A FHIT polynucleotide may be used in the treatment of various disease states associated with chromosome 3p14.2 abnormalities, such as cancers, and/or decreased expression of wild-type FHIT RNA or protein. By introducing FHIT gene sequences into cells, gene therapy can be used to treat conditions associated with under-expression of functional FHIT RNA or protein. Accordingly, the present invention provides a method for treating a disease state associated with a chromosome 3p14.2 abnormality in mammal suffering from a disease state associated with a chromosome 3p14.2 abnormality comprising administering a therapeutically effective amount of a nucleic acid encoding a functional Fhit protein to a mammal suffering from a disease state associated with a chromosome 3p14.2 abnormality. In this embodiment of the invention, the nucleic acid produces its encoded protein that mediates a therapeutic effect by promoting Fhit function, thereby, e.g., inhibiting tumor or cancer appearance or progression.

Any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5):155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the Therapeutic comprises a FHIT nucleic acid that is part of an expression vector that expresses a Fhit protein or fragment or chimeric protein thereof in a suitable host. In particular, such a nucleic acid has a promoter operably linked to the FHIT coding region, said promoter being inducible or constitutive, and, optionally, tissue-specific. In another particular embodiment, a nucleic acid molecule is used in which the FHIT coding sequences and any other desired sequences are flanked by regions that promote homologous recombination at a desired site in the genome, thus providing for intrachromosomal expression of the FHIT nucleic acid (Koller and Smithies, 1989, Proc. Natl. Acad. Sci. USA 86:8932–8935; Zijlstra et al., 1989, Nature 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429–4432) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, a viral vector that contains the FHIT nucleic acid is used. For example, a retroviral vector can be used (see Miller et al., 1993, Meth. Enzymol. 217:581–599). These retroviral vectors have been modified to delete retroviral sequences that are not necessary for packaging of the viral genome and integration into host cell DNA. The FHIT nucleic acid to be used in gene therapy is cloned into the vector, which facilitates delivery of the gene into a patient. More detail about retroviral vectors can be found in Boesen et al., 1994, Biotherapy 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest. 91:225–234.

Adeno-associated virus (AAV) has also been proposed for use in gene therapy (Walsh et al., 1993, Proc. Soc. Exp. Biol. Med. 204:289–300. Herpesviruses can also be used.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, a FHIT nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention. Such stem cells include but are not limited to hematopoietic stem cells (HSC), stem cells of epithelial tissues such as the skin and the lining of the gut, embryonic heart muscle cells, liver stem cells (PCT Publication WO 94/08598, dated Apr. 28, 1994), and neural stem cells (Stemple and Anderson, 1992, Cell 71:973–985).

Epithelial stem cells (ESCs) or keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald, 1980, Meth. Cell Bio. 21A:229; Pittelkow and Scott, 1986, Mayo Clinic Proc. 61:771). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique which provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., 1984, J. Clin. Invest. 73:1377–1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Natl. Acad. Sci. USA 79:3608–3612).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Additional methods that can be adapted for use to deliver a nucleic acid encoding a Fhit protein or functional derivative thereof are described in Section 5.8.5.

5.8.5. ANTAGONIZING DOMINANT-NEGATIVE FHIT MUTATIONS FOR TREATMENT OR PREVENTION OF DISORDERS OF OVERPROLIFERATION

The invention also provides methods of treating or preventing disorders of overproliferation (e.g., cancer, hyperproliferative disorders) in which the patient has a hemizygous FHIT mutation (presumably a dominant-negative FHIT mutation) by specifically antagonizing (administering an antagonist to) the mutant FHIT gene or protein (and not wildtype FHIT or Fhit). Hemizygosity for a FHIT mutation can be detected by observing the presence of both normal and mutant FHIT DNA (e.g., cDNA) or RNA in a sample from a patient, e.g., by methods as described in Sections 5.11 and 6 hereof.

For example, in a specific embodiment, an effective amount of antisense oligonucleotide that inhibits the expression of the mutant FHIT gene, and not the wild-type FHIT gene, is administered. For example, if the hemizygous FHIT mutation in the patient is a deletion of at least a portion of one or more FHIT exons, the antisense oligonucleotide can comprise a hybridizable sequence complementary to the junction formed by the deletion, said junction being present in the mutant FHIT gene but not the wild-type PHIT gene. Thus, the antisense oligonucleotide comprises a sequence complementary to contiguous sequences from two exons not naturally found contiguous in wild-type FHIT cDNA.

In another specific embodiment, an antibody can be used therapeutically or prophylactically to specifically antagonize the hemizygous Fhit mutant protein. For example, such an antibody can specifically recognize an epitope in a Fhit deletion mutant formed by the fusion of sequences not naturally contiguous in the wild-type Fhit protein. For therapeutic purposes, a Fhit mutant protein can be used as immunogen to make anti-Fhit antibodies that neutralize the activity of the Fhit mutant protein and not wild-type Fhit protein. Accordingly, the present invention provides a method for treating a disease state associated with a FHIT abnormality in a mammal suffering from a disease state associated with a FHIT abnormality comprising administering a therapeutically effective amount of an anti-Fhit antibody specific to the abnormal FHIT gene or protein to a mammal suffering from a disease state associated with a FHIT abnormality.

In another specific embodiment, a recombinant nucleic acid consisting of non-FHIT sequences flanked by FHIT sequences so as to promote homologous recombination specifically with a mutant FHIT gene in a patient, is introduced into the patient, in order to "knock out" (inhibit the effect of) the mutant, particularly where such mutant is believed to be a dominant-negative one.

Antisense oligonucleotides are described in further detail below.

5.8.5.1. ANTISENSE REGULATION OF MUTANT FHIT GENE EXPRESSION

In a specific embodiment, mutant function of Fhit or FHIT is specifically inhibited by use of FHIT antisense nucleic acids. The present invention provides the therapeutic or prophylactic use of nucleic acids of at least six nucleotides that are antisense to a gene or cDNA encoding a mutant Fhit. A FHIT "antisense" nucleic acid as used herein refers to a nucleic acid capable of hybridizing to a portion of a FHIT RNA (preferably mRNA) or mutant form thereof by virtue of some sequence complementarity (other than to nonspecific sequences such as a polyA tail). The antisense nucleic acid may be complementary to a coding and/or noncoding region of a FHIT mRNA. Such antisense nucleic acids have utility as Therapeutics that inhibit dominant-negative mutant Fhit function, and can be used in the treatment or prevention of disorders as described supra in Section 5.8 and its subsections.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

The invention further provides pharmaceutical compositions comprising an effective amount of the FHIT antisense nucleic acids of the invention in a pharmaceutically acceptable carrier, as described in Section 5.10.

In another embodiment, the invention is directed to methods for inhibiting the expression specifically of a FHIT mutant nucleic acid sequence in a prokaryotic or eukaryotic cell comprising providing the cell with an effective amount of a composition comprising an FHIT antisense nucleic acid of the invention.

The FHIT antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549).

In a preferred aspect of the invention, a FHIT antisense oligonucleotide is provided, preferably of single-stranded DNA. In a most preferred aspect, such an oligonucleotide comprises a sequence antisense to a junction of two non-normally contiguous sequences in a FHIT gene deletion mutant, most preferably, of a human FHIT gene mutant. The oligonucleotide may be modified at any position on its structure with substituents generally known in the art.

The FHIT antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). These include techniques for chemically synthesizing oligodeoxyribonucleotides well known in the art such as for example solid phase phosphoramidite chemical synthesis. As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

In a specific embodiment, the FHIT antisense oligonucleotide comprises catalytic RNA, or a ribozyme (see, e.g., PCT International Publication WO 90/11364, published Oct. 4, 1990; Sarver et al., 1990, Science 247:1222–1225). Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of mutant FHIT RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

In another embodiment, the oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

In an alternative embodiment, the FHIT antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the FHIT antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the FHIT antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:3942), etc.

The antisense nucleic acids of the invention comprise a sequence complementary to at least a portion of an RNA transcript of a FHIT gene, preferably a human mutant FHIT gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded FHIT antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a FHIT RNA it may contain and still form a stable duplex (or triplex, as the case may be). One skilled in the art can ascertain a tolerable degree of mismatch by use of standard procedures to determine the melting point of the hybridized complex.

The FHIT antisense nucleic acids can be used to treat (or prevent) malignancies or hyperproliferative disorders, of a cell type which has been shown to express mutant FHIT RNA.

Malignant, neoplastic, and pre-neoplastic cells which can be tested for such expression include but are not limited to those described supra in Sections 5.8. In a preferred embodiment, a single-stranded DNA antisense FHIT oligonucleotide is used.

Malignant (particularly, tumor) cell types which express FHIT RNA can be identified by various methods known in the art. Such methods include but are not limited to hybridization with a FHIT-specific nucleic acid (e.g., by Northern hybridization, dot blot hybridization, in situ hybridization), observing the ability of RNA from the cell type to be translated in vitro into Fhit protein, etc. (see the assays described for diagnosis in Section 5.11). In a preferred aspect, primary tumor tissue from a patient can be assayed for FHIT expression prior to treatment.

Pharmaceutical compositions of the invention, comprising an effective amount of a FHIT antisense nucleic acid in a pharmaceutically acceptable carrier, can be administered to a patient having a malignancy which is of a type that expresses mutant FHIT RNA that is specifically antagonized by the antisense nucleic acid.

The amount of FHIT antisense nucleic acid which will be effective in the treatment of a particular disease state or condition will depend on the nature of the disease state or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising FHIT antisense nucleic acids are administered via liposomes, microparticles, or microcapsules. In various embodiments of the invention, it may be useful to use such compositions to achieve sustained release of the FHIT antisense nucleic acids. In a specific embodiment, it may be desirable to utilize liposomes targeted via antibodies to specific identifiable tumor antigens (Leonetti et al., 1990, Proc. Natl. Acad. Sci. USA 87:2448–2451; Renneisen et al., 1990, J. Biol. Chem. 265:16337–16342).

In a particular embodiment of the invention, antisense FHIT oligonucleotides or anti-Fhit antibodies that specifically antagonize a mutant FHIT gene or protein present in a patient, are administered to the patient in combination with administration to the patient of FHIT gene therapy (administration of wild-type Fhit function) or functional Fhit protein or agonists.

5.9. DEMONSTRATION OF THERAPEUTIC OR PROPHYLACTIC UTILITY

The FHIT polynucleotides, FHIT protein products, derivatives and analogs thereof, and antibodies thereto, and antisense nucleic acids of the invention can be tested in vivo for the desired therapeutic or prophylactic activity. For example, such compounds can be tested in suitable animal model systems prior to testing in humans, including but not limited to rats, mice, chicken, cows, monkeys, rabbits, etc. For in vivo testing, prior to administration to humans, any animal model system known in the art may be used.

5.10. THERAPEUTIC/PROPHYLACTIC METHODS AND COMPOSITIONS

The invention provides methods of treatment and prophylaxis by administration to a subject of an effective amount of a Therapeutic, i.e., a FHIT nucleic acid, FHIT protein, derivative or analog thereof, or antibody thereto of the present invention. In a preferred aspect, the Therapeutic is substantially purified. The subject is preferably an animal, including but not limited to animals such as cows, pigs, chickens, etc., and is preferably a mammal, and most preferably human. The subject can be a fetus, child, or adult.

In a specific embodiment, a non-human mammal is the subject.

Formulations and methods of administration that can be employed when the Therapeutic comprises a nucleic acid are described in Sections 5.8.4 and 5.8.5.1 above; additional appropriate formulations and routes of administration can be selected from among those described hereinbelow.

Various delivery systems are known and can be used to administer a Therapeutic of the invention, e.g., encapsulation in liposomes, microparticles, microcapsules, expression by recombinant cells, receptor-mediated endocytosis (see, e.g., Wu and Wu, 1987, J. Biol. Chem. 262:4429–4432), construction of a therapeutic nucleic acid as part of a retroviral or other vector, etc. Methods of introduction include but are not limited to intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In a specific embodiment where the Therapeutic is a nucleic acid encoding a protein therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid therapeutic can be introduced intracellularly and incorporated within host cell DNA for expression, by homologous recombination.

The present invention also provides pharmaceutical compositions. Such compositions comprise a therapeutically effective amount of a therapeutic, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline.

Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.11. DIAGNOSTIC USES

A FHIT polynucleotide and nucleic acids complementary thereto, its Fhit protein product, fragments thereof, and antibodies thereto can be used for diagnostic purposes for disorders involving overproliferation of cells, as well as other disorders associated with chromosomal translocations and inversions or molecular abnormalities associated with the FHIT gene, and/or decreased expression of wild-type FHIT RNA or protein.

Such molecules can also be used in diagnostic assays, such as immunoassays, to detect, prognose, diagnose, or monitor various conditions, diseases, and disorders associated with expression of mutant FHIT transcripts or monitor the treatment thereof. Accordingly, in specific embodiments, cancer or premalignant changes or hyperproliferative or benign dysproliferative disorders in tissue is diagnosed by detecting the presence of one or more mutant FHIT transcripts, alone or in combination with a decrease in expression of wild-type FHIT transcript, in patient samples relative to FHIT expression in an analogous non-diseased sample (from the patient or another person, as determined experimentally or as is known as a standard level in such samples). For diagnostic purposes, a FHIT polynucleotide may be used to detect mutant FHIT gene expression in disease states.

The subject, or patient, is an animal, e.g., a mammal, and is preferably human, and can be a fetus, child, or adult.

As illustrated infra, the FHIT gene sequence is associated with cancers, particularly associated with translocations and deletions within the FHIT gene. In specific embodiments, diseases and disorders involving overproliferation of cells can be diagnosed, or their suspected presence can be screened for, or a predisposition to develop such disorders can be detected, by detecting decreased levels of wild-type Fhit protein, wild-type FHIT RNA, or Fhit functional activity, or by detecting mutations in FHIT RNA, DNA, cDNA, or protein (e.g., translocations or deletions in FHIT nucleic acids, truncations in the FHIT gene or protein, changes in nucleotide or amino acid sequence relative to wildtype Fhit) that cause decreased expression or activity of Fhit or a dominant-negative effect. Such diseases and disorders include but are not limited to those described in Section 5.8 and its subsections. By way of example, levels of Fhit protein can be detected by immunoassay, levels of FHIT RNA can be detected by hybridization assays (e.g., Northern blots, dot blots) or RT-PCR, translocations, deletions, and point mutations in FHIT nucleic acids can be detected by Southern blotting, RFLP analysis, PCR of cDNA using primers that preferably generate a fragment spanning at least most of the FHIT gene, sequencing of the FHIT genomic DNA or cDNA obtained from the patient, etc.

In a preferred embodiment, levels of FHIT mRNA (or cDNA) or protein in a patient sample are detected or measured or analyzed by size and/or sequence, in which aberrant levels, size or sequence indicate that the subject has, or has a predisposition to developing, a malignancy or hyperproliferative disorder; in which the decreased levels are relative to the levels present in an analogous sample from a portion of the body or from a subject not having the malignancy or hyperproliferative disorder, as the case may be.

FHIT gene sequences may be used diagnostically for the detection of diseases states resulting from chromosomal or molecular abnormalities, e.g., translocations, inversions and deletions, involving the FHIT gene. Nucleic acids comprising FHIT nucleotide sequences of at least 8 nucleotides, at least nucleotides, at least 25 nucleotides, at least 50 nucleotides, at least 100 nucleotides, at least 200 nucleotides, at least 300 nucleotides, and preferably less than 500 nucleotides, and the nucleic acids described in Section 5.1, may be used as probes in hybridization assays for the detection and measurement of FHIT gene sequences. Nucleic acids of not more than 5 kilobases, of not more than 10 kilobases, not more than 25 kilobases, not more than 50 kilobases or not more than 70 kilobases which are hybridizable to a FHIT gene, cDNA, or complementary strand can be used as probes in hybridization assays for the detection and measurement of FHIT nucleotide sequences. As an example, the FHIT DNA sequence may be used in hybridization assays, e.g., Southern or Northern analysis, including in situ hybridization assays, of patient's samples to diagnose abnormalities of FHIT expression. Hybridization assays can be used to detect, prognose, diagnose, or monitor malignancies, associated with aberrant changes in FHIT expression and/or activity as described supra. In particular, such a hybridization assay is carried out by a method comprising contacting a sample containing nucleic acid with a nucleic acid probe capable of hybridizing to FHIT DNA (e.g., cDNA) or RNA, under conditions such that hybridization can occur, and detecting or measuring any resulting hybridization. In particular, hybridization assays can be used to detect the presence of abnormalities associated with expression of mutant FHIT mRNA, by hybridizing mRNA or cDNA from a patient sample to a FHIT probe, and analyzing by size and/or sequence the resulting hybridized nucleic acids. For example, assays which can be used include, but are not limited to Northern blots, dot blots, etc. A particular hybridization assay is Northern blot analysis of a patient sample using FHIT gene probes of at least 15 nucleotides up to the full length cDNA sequence shown in FIG. 2A. Another hybridization assay is in situ hybridization analysis of a patient sample using anti-FHIT antibodies or FHIT nucleotide hybridization probes. Such techniques are well known in the art, and are in fact the basis of many commercially available diagnostic kits.

In a specific embodiment, cancer or other disorder of cell overproliferation (e.g., those described in Sections 5.8.1–5.8.3 above), is diagnosed or prognosed by detecting a mutation in the FHIT gene or its produced RNA in a sample derived from a patient. The mutation can be a translocation, deletion, insertion or substitution/point mutation. In a preferred embodiment, the mutation is a deletion of all or a portion of at least one coding exon (i.e., exon 5, 6, 7, 8 or 9), preferably exon 5 or exon 8. In a preferred embodiment, the deletion is a homozygous deletion. In another embodiment, the mutation is a mutation that causes a frameshift upstream of exon 8, or otherwise causes a lack of the wild-type open reading frame (ORF) of exon 8 in the patient's FHIT RNA. In another particular embodiment, the mutation that is detected is an insertion into a coding region of the FHIT gene or an insertion downstream of exon 4, or an insertion in the 5' noncoding region between exon 4 and 5. In a specific embodiment, the mutation in the FHIT gene coding sequence is detected by detecting an aberrant sized FHIT cDNA or mRNA in the subject (i.e., FHIT RNA or cDNA that has a different size than the wild-type FHIT RNA (that is present or expected to be present in normal individuals not having or pre-disposed to a cancer associated with a FHIT mutation, e.g., the ~1.1 kb transcript)).

Polynucleotide sequences of FHIT consisting of at least 8 to 25 nucleotides that are useful as primers in primer dependent nucleic acid amplification methods may be used for the detection of mutant FHIT genomic or RNA sequences in patient samples. Primer dependent nucleic acid amplification methods useful in the present invention include, but are not limited to, polymerase chain reaction (PCR), competitive PCR, cyclic probe reaction, and ligase chain reaction. Such techniques are well known by those of skill in the art. A preferred nucleic acid amplification method of the present invention is reverse transcriptase PCR (RT-PCR) (Siebert et al., 1992, Nature 359:557–558).

In a particular embodiment of the present invention, each primer of a pair of primers for use in a primer dependent nucleic acid amplification method is selected from a different exon of the genomic FHIT nucleotide sequences. For example, if one primer of a pair or primers is selected from exon 1 of the FHIT genomic sequence, the second primer will be selected from exon 2, 3, 4, 5, 6, 7, 8, 9 or 10 of the FHIT genomic sequence. As another example, if one primer of a pair of primers is selected from exon 2 of the FHIT genomic sequence, the second primer will be selected from exon 1, 3, 4, 5, 6, 7, 8, 9 or 10 of the FHIT genomic sequence. Resulting amplified genomic nucleotide sequences will contain amplified intron sequences and will be of a larger size than amplified cDNA nucleotide sequences that will not contain amplified intron sequences. Similarly, amplified cDNA sequences having a deletion mutation can be distinguished from amplified wild-type sequences due to the size difference of the resulting amplified sequences (the deletion mutant will generate a shorter amplified fragment). For amplification of cDNA nucleotide sequences, the primer sequences should be selected from exons sequences that are sufficiently far enough apart to provide a detectable amplified nucleotide sequence.

In a specific embodiment, cancer or other disorder of cell proliferation or a predisposition thereto is detected or diagnosed in a subject by detecting mutation(s) within the FHIT gene as follows: A sample containing RNA of tissue or cells of a patient is obtained, and the RNA is reverse-transcribed into cDNA by methods commonly known in the art; preferably this step is followed by amplifying fragments comprising FHIT coding sequences within the cDNA, and detecting one or more mutation(s) within the FHIT coding sequences within the amplified fragment. The amplification can be by any suitable methods known in the art, and is preferably done by polymerase chain reaction (PCR). RT-PCR is preferred due to the great size (>500 kb) of the FHIT gene in the genome, which renders one unable to amplify a single fragment containing most of the FHIT exons from a genomic sample, whereas amplification of such a fragment is readily accomplished from a cDNA sample. The primers for use in PCR are upstream and downstream primers that prime synthesis by a polymerase toward each other, and are preferably in the range of 8–35 nucleotides, preferably separated by in the range of 10–2,000 nucleotides in the FHIT mRNA. In a preferred embodiment, each primer comprises a hybridizable sequence contained within an exon of the FHIT gene or within 200 nucleotides flanking (5' or 3' to) an exon of the FHIT gene. In a specific embodiment, the first primer hybridizes 5' to exon 5 (preferably containing sequences of exon 4 or 5' thereto) and the second primer hybridizes on the other strand 5' to the intron between exons 5 and 6 (such that an amplified fragment from wild-type FHIT cDNA would contain exon 5). In another specific embodiment, the second primer hybridizes on the other strand 5' to exon 6. In other specific embodiments, the first and second primers respectively hybridize on opposite strands 5' to the 3' terminus of exon 4 and 5' to exon 8; 5' to the 3' terminus of exon 4 and 5' to exon 9; and 5' to exon 1 and 5' to exon 10, such that the resulting amplified fragment would contain the exon sequences normally present between where the primers hybridize should they be present in the cDNA. Thus, for example, in the foregoing examples, the PCR primer pairs are adapted to amplify a fragment of wild-type FHIT cDNA comprising FHIT exon 5, exon 5 plus exon 6, sequences between the 3' terminus of exon 4 and exon 8, sequences between the 3' terminus of exon 4 and exon 9, and exons 1 through 10, respectively. The presence of one or more mutations in the cDNA can be detected by detecting an aberrantly sized (preferably amplified) fragment (compared to those fragment(s) produced by a wild-type FHIT transcript), e.g., by subjecting the cDNA to size separation such as by agarose gel electrophoresis or column chromatography. In a preferred embodiment, the presence of one or more mutations in the cDNA is detected by sequencing of the cDNA, or more preferably, of the isolated fragments amplified from the cDNA.

The amplified fragments can be isolated by methods known in the art, e.g., agarose gel electrophoresis and recovery from the gel band and/or column chromatography. Such sequencing can be carried out by standard methods commonly known in the art, and can be automated or manual.

In yet another specific embodiment, mutation(s) in the FHIT gene or mRNA from a patient can be detected by other methods commonly known in the art, e.g., Northern hybridization. By way of example but not limitation, RNA from a patient's tissue is separated by gel electrophoresis, transferred to a filter or other solid phase, and hybridized to labelled DNA probes. The hybridized RNAs are then visualized by detecting the label. Preferably, numerous DNA probes are used, from different portions of the FHIT cDNA.

In another embodiment, Southern hybridization can be used to detect gross mutations in FHIT DNA. For example, genomic DNA isolated from a patient, separated by gel electrophoresis, transferred to a filter or other solid phase, and hybridized with a FHIT probe (e.g., an oligonucleotide containing a FHIT gene sequence, affixed to a detectable label). Preferably, a multiplicity of FHIT probes are used, hybridizable to sequences within each of the coding exons, and particularly preferably, including probe(s) hybridizable to sequences within exon 5.

In another embodiment, a translocation within the FHIT gene is detected by methods commonly known in the art. For example, in a preferred embodiment, a sample comprising FHIT genomic DNA, or, preferably FHIT cDNA (e.g., cDNA of total polyA mRNA) from a patient is subjected to PCR by use of primers that prime synthesis across the suspected translocation junction. For example, one primer can have a sequence hybridizable to chromosome 3 (preferably within the FHIT gene upstream of exon 4, e.g., a sequence within exon 1, 2 or 3) and one primer can have a sequence hybridizable to chromosome 8 (downstream of the translocation event); amplification of a fragment indicates the presence of a translocation between chromosomes 3 and 8. Additionally or alternatively performing PCR by priming with primers, each having a sequence within the FHIT gene (see e.g., description supra regarding primers for RT-PCR) will result in an amplified fragment only if at least one FHIT allele contains the primer sequences undisrupted by a translocation event in between them.

Detection of homozygous mutations (mutations in both alleles) in FHIT genes are deemed more severe indicators of the presence of, or a predisposition to, cancer than hemizygous mutations (of one allele) in FHIT genes.

As used herein, patient samples which can be used include, but are not limited to, fresh or frozen tissue samples, which can be used in in situ hybridization assays; cell or tissue from biopsies and, in general, patient samples containing nucleic acid, which can be used in assays that measure or quantitate or analyze FHIT nucleic acid.

The FHIT gene sequences of the present invention may be used diagnostically for the detection of chromosome 3p14.2 abnormalities, in particular, translocations with chromosome 8, and deletions. Accordingly, the present invention provides a process for detecting a target sequence indicative of or including a chromosome 3p14.2 abnormality in a sample, comprising the steps of amplifying the target sequence in the sample using a first primer of 8 to 25 nucleotides, preferably 18–25 nucleotides, complementary to the nucleotide sequence of SEQ ID NO: 1, and a second primer complementary to a region telomeric or centromeric to the FHIT gene and detecting any resulting amplified target sequence in which the presence of the amplified target sequence is indicative of the abnormality. The present invention also provides a method of diagnosing a malignancy associated with chromosome 3p14.2 abnormalities in a patient comprising, detecting said chromosome 3p14.2 abnormality according to the method above in which the presence of an amplified target sequence indicative of a mutant FHIT transcript indicates the presence of a cancer or precancerous condition in the patient. The resultant amplified target sequence can be detected on gel electrophoresis and compared with a normal sample or standard that does not contain a chromosome 3p14.2 abnormality. The amplification of genomic DNA target sequences may require generating long PCR products. PCR techniques for generating long PCR products are described in Science (1994) 263:1564–1565; PCR kits for generating long PCR products are available from Perkin Elmer and Takara Shuzo Co., Ltd. The present invention also provides a method for detecting a target nucleotide sequence indicative of or including at least a portion of a chromosome 3p14.2 abnormality (thereby indicative of the presence of or a predisposition to a disorder of cell overproliferation) in a nucleic acid sample, comprising the steps of hybridizing the sample with a nucleic acid probe of not more than 10 kilobases, comprising FHIT cDNA sequences selected from among at least exon 1, 2, 3 or 4 and selected from among at least exon 7, 8 or 9, or a sequence absolutely complementary thereto, and detecting or measuring the amount of any resulting hybridization between the probe and the target sequence within the sample. Alternatively, the probe comprises at least 310 contiguous nucleotides of a FHIT cDNA, or at least 266 contiguous nucleotides of FHIT cDNA coding sequences.

The resultant hybridization between the probe and the target sequence within the sample can be detected using gel electrophoresis and can be compared to a target sequence from a normal sample or standard that does not contain the abnormality. The present invention also provides a method of diagnosing a malignancy associated with a FHIT abnormality in a patient comprising detecting said FHIT abnormality according to the method above in which the presence of the amplified target sequence indicates the presence of a malignancy in the patient. Absolute complementarity between a hybridization probe and a target sequence, although preferred, is not required. A sequence "complementary to at least a portion of", as referred to herein, means a sequence having sufficient complementarity to be able to hybridize with the nucleic acid forming a stable hybridization complex. The ability to hybridize will depend on both the degree of complementarity and the length of the nucleic acid. Generally, the longer the hybridizing nucleic acid, the more base mismatches with a FHIT RNA it may contain and still form a stable duplex (or triplex as the case may be). One skilled in the art can ascertain a tolerable degree of mismatch by use of standard procedures to determine the melting point of the hybridized complex.

An additional aspect of the present invention relates to diagnostic kits for the detection or measurement of FHIT gene sequences and FHIT protein. Kits for diagnostic use are provided, that comprise in one or more containers an anti-Fhit antibody, and, optionally, a labeled binding partner to the antibody. Alternatively, the anti-Fhit antibody can be labeled (with a detectable marker, e.g., a chemiluminescent, enzymatic, fluorescent, or radioactive moiety). A kit is also provided that comprises in one or more containers a nucleic acid probe capable of hybridizing to FHIT RNA. Accordingly, the present invention provides a diagnostic kit comprising, in a container a compound comprising a probe of not more than 10 kilobases and comprising FHIT cDNA sequences comprising at least one of exon 1, 2, 3 or 4 and at least one of exon 7, 8 or 9; or its complement. Alternatively, the probe comprises at least 310 contiguous nucleotides of a FHIT cDNA, or at least 266 contiguous nucleotides of FHIT cDNA coding sequences. Alternatively, the present invention provides a diagnostic kit comprising, in one or more containers, a pair of primers of at least 8–35, preferably 8–25, nucleotides in which at least one of said primers is hybridizable to SEQ ID NO: 1 or its complement and wherein said primers are capable of priming cDNA synthesis in an amplification reaction. In a specific embodiment, a kit can comprise in one or more containers a pair of primers (e.g., each in the size range of 8–35 nucleotides) that are capable of priming amplification [e.g., by polymerase chain reaction (see e.g., Innis et al., 1990, PCR Protocols, Academic Press, Inc., San Diego, Calif.), ligase chain reaction (see EP 320,308) use of Qβ replicase, cyclic probe reaction, or other methods known in the art] under appropriate reaction conditions of at least a portion of a FHIT nucleic acid. The present invention also provides a diagnostic kit in which at least one of the primers is hybridizable to SEQ ID NO: 1 or its complement and in which one of the primers is hybridizable to a DNA sequence located telomeric or centromeric to the FHIT gene. In another embodiment, the kit comprises a primer pair such as described supra for use in diagnostic assays. In a specific embodiment one of the foregoing compounds of the container can be detectably labeled. A kit can optionally further comprise in a container a predetermined amount of a purified Fhit protein or nucleic acid, e.g., for use as a standard or control.

The amplification reaction of the present invention may be a polymerase chain reaction, competitive PCR and competitive reverse-transcriptase PCR (Clementi et al., 1994, Genet Anal Tech Appl 11(1):1–6 and Siebert et al., 1992, Nature 359:557–558); cyclic probe reaction, which allows for amplification of a target sequence using a hybrid RNA/DNA probe and RNase (ID Biomedical); ligase chain reaction (Wu et al., 1989, Genomics 4:560–569). In a particular embodiment, the chromosomal abnormality associated with a FHIT locus can be detected as described in PCT Publication No. WO92/19775, dated Nov. 12, 1992. In a specific embodiment, the FHIT probe used in a hybridization assay is detectably labeled. Such a label can be any known in the art including, but not limited to, radioactive labels, fluorescent labels, biotin, chemiluminescent labels, etc.

In a specific embodiment in which the assay used employs primers, at least one primer can be detectably labeled. In another embodiment, one of a primer pair is attached to a moiety providing for capture, e.g., a magnetic bead.

Anti-FHIT antibodies may be generated and used diagnostically to detect the presence of mutant Fhit protein in patient samples, and/or the absence of wild-type Fhit protein, thereby identifying disease states associated with chromosome 3p14.2 abnormalities such as disorders of cell overproliferation.

For example, in one embodiment, where one is detecting or measuring mutant Fhit protein by assaying for binding to anti-Fhit antibody, various immunoassays known in the art can be used, including but not limited to competitive and noncompetitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, in situ hybridizations, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention. In particular, such an immunoassay is carried out by a method comprising contacting a sample derived from a patient with an anti-Fhit antibody under conditions such that immunospecific binding can occur, and detecting or measuring the amount of any immunospecific binding by the antibody. In a specific embodiment, antibody to a Fhit protein can be used to assay a patient tissue or serum sample for the presence of a FHIT protein where an increased level of FHIT protein is an indication of a diseased condition. In one embodiment of the present invention, the FHIT protein is detected or measured by immunocytochemistry of a patient sample. In another embodiment, assays to measure the levels of FHIT protein or RNA can be used to monitor therapy of disease associated with increased expression of FHIT. For example, a decrease in levels of FHIT RNA or protein after therapy, relative to the level found before therapy, may be indicative of a favorable response to therapy. An increase in such levels after therapy may be indicative of a poor response to therapy.

For detection of Fhit protein sequences, a diagnostic kit of the present invention comprises, in one or more containers, an anti-Fhit antibody which optionally can be detectably labeled. In a different embodiment, the kit can comprise in a container, a labeled specific binding portion of an antibody. As used herein, the term detectable label refers to any label which provides directly or indirectly a detectable signal and includes, for example, enzymes, radiolabelled molecules, fluorescent molecules, particles, chemiluminesors, enzyme substrates or cofactors, enzyme inhibitors, or magnetic particles. Examples of enzymes useful as detectable labels in the present invention include alkaline phosphatase and horse radish peroxidase. A variety of methods are available for linking the detectable labels to proteins of interest and include for example the use of a bifunctional agent, such as, 4,4'-difluoro-3,3'-dinitro-phenylsulfone, for attaching an enzyme, for example, horse radish peroxidase, to a protein of interest. The attached enzyme is then allowed to react with substrate yielding a reaction product which is detectable. The present invention provides a method for detecting a Fhit protein in a patient sample, comprising, contacting the patient sample with an anti-Fhit antibody under conditions such that immunospecific binding can occur, and detecting or measuring the amount of any immunospecific binding by the antibody. The method preferably also comprises subjecting the protein to size fractionation and/or sequence determination.

Samples can be any sample from a patient containing FHIT protein, e.g., tissue sections.

In diagnosing disease states, the functional activity of Fhit proteins, derivatives and analogs may be assayed by various methods. Accordingly, the present invention also provides a method of diagnosing a malignancy or other disorder associated with chromosome 3p14.2 (FHIT) abnormalities in a patient comprising, detecting expression of a mutant Fhit protein in a sample from the patient, in which the presence of a mutant Fhit protein indicates the presence of a malignancy or other disorder associated with FHIT abnormalities in the patient.

In a specific embodiment of the invention, prenatal diagnosis of a disorder of cell overproliferation or a predisposition thereto, is carried out. For example, one can first obtain tissue (e.g., blood cells) from an expectant parent. If one or more of the expectant parents have a FHIT mutation, thus indicating possible inheritance of this mutation by the offspring, amniocentesis or some other method of fetal tissue sampling can then be carried out to obtain fetal cells which can then be tested for the presence of FHIT mutant DNA or RNA or protein by methods as described above (e.g., RT-PCR to detect mutant FHIT RNA).

In another embodiment, the levels of FHIT protein or RNA expression may be used to stage or monitor disease, with the appearance of or an increase in mutant Fhit protein or RNA expression, and/or a decrease of or loss in wild-type Fhit protein or RNA expression, relative to that present in a sample derived from the subject at an earlier time, indicates disease progression.

The ability of antibodies, peptides or other molecules to modulate the effect of Fhit protein on disease states may be monitored. For example, the expression of FHIT gene sequence, or Fhit protein sequences may be detected as described, supra, both before and after administration of a therapeutic composition, e.g., comprising a FHIT nucleotide sequence, Fhit protein sequence, derivative or analog thereof, or antibody thereto, or antisense nucleic acid of the present invention.

In another embodiment, presence of FHIT mutation(s), particularly homozygous ones, can be used as indicators of adverse outcome to therapy or recurrence of the disorder in patients with disorders of cell overproliferation.

Other methods will be known to the skilled artisan and are within the scope of the invention.

5.12. SCREENING FOR Fhit AGONISTS AND ANTAGONISTS

FHIT nucleic acids, proteins, and derivatives also have uses in screening assays to detect molecules that specifically bind to FHIT nucleic acids, proteins, or derivatives and thus have potential use as agonists or antagonists of Fhit, in particular, molecules that thus affect cell proliferation. I a preferred embodiment, such assays are performed to screen for molecules with potential utility as anti-cancer drugs or lead compounds for drug development. The invention thus provides assays to detect molecules that specifically bind to FHIT nucleic acids, proteins, or derivatives. For example, recombinant cells expressing FHIT nucleic acids can be used t recombinantly produce Fhit proteins in these assays, to screen for molecules that bind to a Fhit protein. Molecules (e.g., putative binding partners of Fhit) are contacted with the Fhit protein (or fragment thereof) under conditions conducive to binding, and then molecules that specifically bind to the Fhit protein are identified. Similar methods can be used to screen for molecules that bind to Fhit derivatives or nucleic acids. Methods that can be used to carry out the foregoing are commonly known in the art.

In a specific embodiment of the present invention, a Fhit protein and/or cell line that expresses a Fhit protein can be used to screen for antibodies, peptides, or other molecules that bind to the FHIT protein and thus may act as agonists or antagonists of FHIT protein. For example, anti-Fhit antibodies capable of neutralizing the activity of a dominant-negative mutant Fhit protein may be used to inhibit or prevent a disease state associated with cell overproliferation such as cancer.

Screening of organic or peptide libraries with recombinantly expressed mutant Fhit protein may be useful for identification of therapeutic molecules that function to inhibit the activity of mutant Fhit protein. Screening against wild-type Fhit protein can then be carried out to select for antagonists specific to the mutant Fhit protein, i.e., that do not inhibit (or bind) the wild-type Fhit protein. Synthetic and naturally occurring products can be screened in a number of ways deemed routine to those of skill in the art.

By way of example, diversity libraries, such as random o combinatorial peptide or nonpeptide libraries can be screened for molecules that specifically bind to Fhit. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, R. B., et al., 1992, J. Mol. Biol. 227:711–718); Lenstra, 1992, J. Immunol. Meth. 152:149–157; Kay et al., 1993, Gene 128:59–65; and PCT Publication No. WO 94/18318 dated Aug. 18, 1994.

In vitro translation-based libraries include but are not limited to those described in PCT Publication No. WO 91/0505 dated Apr. 18, 1991; and Mattheakis et al., 1994, Proc. Natl. Acad. Sci. USA 91:9022–9026.

By way of examples of nonpeptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

Screening the libraries can be accomplished by any of a variety of commonly known methods. See, e.g., the following references, which disclose screening of peptide libraries: Parmley and Smith, 1989, Adv. Exp. Med. Biol. 251:215–218; Scott and Smith, 1990, Science 249:386–390; Fowlkes et al., 1992, BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar and Pabo, 1993, Science 263:671–673; and PCT Publication No. WO 94/18318.

In a specific embodiment, screening can be carried out by contacting the library members with a Fhit protein (or nuclei acid or derivative) immobilized on a solid phase and harvesting those library members that bind to the protein (ot nucleic acid or derivative). Examples of such screening methods, termed "panning" techniques are described by way of example in Parmley and Smith, 1988, Gene 73:305–318; Fowlkes et al., 1992, BioTechniques 13:422–427; PCT Publication No. WO 94/18318; and in references cited hereinabove.

In another embodiment, the two-hybrid system for selecting interacting proteins in yeast (Fields and Song, 1989, Nature 340:245–246; Chien et al., 1991, Proc. Natl. Acad. Sci. USA 88:9578–9582) can be used to identify molecules that specifically bind to a Fhit protein or derivative.

5.13. ANIMAL MODELS

The invention also provides animal models.

In one embodiment, animal models for diseases and disorders involving cell overproliferation (e.g., as describe( in Section 5.8.1) are provided. Such an animal can be initially produced by promoting homologous recombination between a FHIT gene in its chromosome and an exogenous FHIT gene that has been rendered biologically inactive (preferably by insertion of a heterologous sequence, e.g., an antibiotic resistance gene). In a preferred aspect, this homologous recombination is carried out by transforming embryo-derived stem (ES) cells with a vector containing the insertionally inactivated FHIT gene, such that homologous recombination occurs, followed by injecting the ES cells into a blastocyst, and implanting the blastocyst into a foster mother, followed by the birth of the chimeric animal ("knockout animal") in which a FHIT gene has been inactivated (see Capecchi, 1989, Science 244:1288–1292). The chimeric animal can be bred to produce additional knockout animals. Such animals can be mice, hamsters, sheep, pigs, cattle, etc., and are preferably non-human mammals. In a specific embodiment, a knockout mouse is produced.

Such knockout animals are expected to develop or be predisposed to developing diseases or disorders involving cell overproliferation (e.g., malignancy) and thus can have use as animal models of such diseases and disorders, e.g., to screen for or test molecules (e.g., potential anti-cancer therapeutics) for the ability to inhibit overproliferation (e.g., tumor formation) and thus treat or prevent such diseases or disorders.

In a different embodiment of the invention, transgenic animals that have incorporated and express a dominant-negative mutant FHIT gene have use as animal models of diseases and disorders involving cell overproliferation. Such animals ca be used to screen for or test molecules for the ability to specifically inhibit the dominant-negative mutant and thus treat or prevent such diseases and disorders.

6. THE HUMAN FHIT GENE, SPANNING THE CHROMOSOME 3p14.2 FRAGILE SITE AND RENAL CARCINOMA ASSOCIATED TRANSLOCATION BREAKPOINT, IS ABNORMAL IN DIGESTIVE TRACT CANCERS

As described herein, we have isolated and characterized a human gene involved in esophageal, gastric, colon, kidney, and other cancers. A 200–300 kilobase (kb) region of chromosome 3p14.2, including the fragile site locus, FRA3B, is involved in homozygous deletions in multiple tumor-derived cell lines and in hemizygous deletions in esophageal, gastric, colon, kidney and other cancers. Exon amplification from a cosmid contig covering this 200–300 kilobase region allowed identification of the human FHIT gene, a member of the zinc-binding histidine triad gene family, which encodes a ubiquitous 1.1 kilobase transcript and a 16.8 kDa protein wit homology to a protein kinase C inhibitor gene, another member of the HIT family.

The FHIT locus is composed of 10 small exons distribute over at least 500 kilobases, with the three 5' most untranslated exons mapping centromeric to the clear cell renal carcinoma associated 3p14.2 translocation breakpoint; the remaining exons map telomeric to this translocation breakpoint with exon 5, the first amino acid coding exon, falling within the homozygously deleted fragile region, FRA3B, and exons 6–10 mapping telomeric to the tumor cell common deleted region and the FRA3B region. Aberrant transcripts of the FHIT locus were found in approximately 50% of esophageal, stomach and colon carcinomas, and the familial t(3;8) renal carcinomas have loss one FHIT allele due to disruption by the translocation.

The aberrant FHIT transcripts usually resulted from abnormal splicing, which often deleted exon 5 or 8, resulting in transcripts which could not encode Fhit protein. Thus, chromosome abnormalities at 3p14.2 and FRA3B, resulting in loss of the Fhit protein, are involved in initiation and/or progression of several important types of human cancer.

6.1. RESULTS

The cosmid contig

From the 648D4 cosmid library, clones were selected initially using the BE758–6, A6URA, A3, and 1300E3, probes, which were distributed across the homozygously deleted region as shown in FIG. 1A. Cosmid end-clones were then isolated an used for the next round of cosmid screening. The cosmid map was assembled by PCR-amplification of the starting STSs (DNA sequence tags) and new ones developed from cosmid ends, using cosmid DNA templates. Additionally, each new STS was tested against the YAC contig (also shown in FIG. 1A), against cell lines with homozygous deletions and rodent-human hybrids retaining portions of chromosome 3 (LaForgia et al., 1993, Cancer Res. 53:3118–3124; Druck et al., 1995, Cancer Res. 55:5348–5355; Bullrich et al., 1995, Cytogenet. Cell Genet. 70:250–254). Six cosmids were assembled into a contig which covered the homozygously deleted region.

To define more precisely the homozygously deleted region, which we will refer to as the fragile region, 42 STS markers, spanning the chromosomal region from the PTPRG locus to D3S1234, derived from cosmid walking and exon trapping, were tested by PCR-amplification for presence in eleven cancer-derived cell lines which had been tested previously with a subset of markers (data not shown; and Lisitsyn et al., 1995 Proc. Natl. Acad. Sci. USA 92:151–155).

Colon carcinoma-derived LoVo, HT29 and SW480 and gastric carcinoma-derived AGS cell lines showed similar large deletions such as depicted by the dotted portion of the top line in FIG. 1A. Colon carcinoma-derived LS180 and breast carcinoma-derived MDA-MB436 cells exhibited discontinuous deletions, covering this same region, with most markers lost but some retained. The gastric carcinoma-derived KatoIII cells appeared to have lost the D3S1481 marker and the telomeric portion of the fragile region, from AP4/5 to D3S2977 (see FIG. 1A). The HKI cells, derived from a nasopharyngeal carcinoma (NPC), had lost the region between D3S1481 and the AP4/5 marker, while CNE2, another NPC-derived cell line had a discontinuous deletion which included a region near the t(3;8) and the region between D3S1481 and D3S2977. HeLa cells also exhibited discontinuous deletions with one deleted region near the t(3;8) and between D3S1481 and AP4/5. The NPC-derived CNE1 cells were tested with most markers without detection of a deletion. Thus, there are many different tumor associated 3p14.2 chromosome breakpoints surrounding the t(3;8), the FRA3B locus and the homozygously deleted region covered by the cosmid contig.

Isolation of cDNAs

The six cosmids covering the homozygous deletion, shown in FIG. 1A, were used in exon trapping experiments aimed at identifying genes within the deleted region. Putative trapped exons were sequenced and sequences analyzed using GRAIL 2 of the ORNL GRAIL server. Several trapped exons were recognized as exons by Grail 2 and were used as probes on northern blots of poly A$^+$RNA from a spectrum of human tissues. Additionally, sequences of trapped exons were compared against nucleotide sequence databases. One exon, trapped from a cosmid 76 subclone (c76, FIG. 1A) matched a number of cDNA sequences from breast (Genbank accession #R53187 and #R86313 and fetal liver and spleen (#R11128) libraries submitted by the Washington University-Merck EST Project. A 23 basepair (bp) oligonucleotide primer designed from this sequence (FIG. 2A, primer X8) was used in primer extension to obtain a 5' extended product of the cDNA by a RACE (Rapid amplification cDNA ends) reaction (Marathon™ cDNA amplification kit, Clontech). The longest product (370 bp) from the RACE reaction detected a ubiquitously expressed 1.1-kb mRNA by northern blot analysis of mRNAs from various normal tissues. The size was similar to the length of the largest cDNA clone isolated from a normal colon cDNA library using the same DNA fragment as a probe. The DNA sequence analysis of this full length clone (FIG. 2A) revealed a long 5' untranslated region of more than 350 bp followed by an initial methionine codon and surrounding sequence which fitted Kozak's rule, an open reading frame (ORF) of 147 amino acids, a 3' untranslated region, a polyadenylation consensus sequence and a poly A tail. Exon sizes varied widely, e.g., exon 5 having 120 nucleotides, exon 6 having 146 nucleotides, and exon 7 having nucleotides. With reference to FIG. 2A, exon 1 consists of nucleotide numbers −362 to −213; exon 2 consists of nucleotide numbers −212 to −164; exon 3 consists of nucleotide numbers −163 to −111; exon 4 consists of nucleotide numbers −110 to −18; exon 5 consists of nucleotide numbers −17 to 103 exon 6 consists of nucleotide numbers 104 to 249; exon 7 consists of nucleotide numbers 250 to 279; exon 8 consists of nucleotide numbers 280 to 348; exon 9 consists of nucleotide numbers 349 to 449; and exon 10 consists of nucleotide number 450 to 733.

A hydrophilicity plot for the Fhit protein was carried out and is shown in FIG. 6.

This FHIT cDNA, as well as the matching sequences from the EST database, were translated and open reading frame (ORF amino acid sequences (FIG. 2A) compared to the protein databases. The longest EST in the 5' direction was R50713 (which contained sequence found in the 3' end of FHIT exon 7, exon 8, and exon 9). The longest EST in the 3' direction was R11128 (which contained sequence found in half of exon 2, and in exons 3–6). EST R53187 had the longest span of sequences corresponding to the FHIT cDNA, including 297 nucleotides identical to the FHIT cDNA sequence from exon 2 through a portion of exon 5. Among the best matches in the database retrieved by computer searches, this 297 nucleotide sequence was the longest stretch of identity with the FHIT cDNA sequence. The next longest stretch of identity was found in EST 11128, with 287 nucleotides identical to the FHIT cDNA sequence starting within exon 2 until 3 bases before the end of exon 6. A printout of the R50713 nucleotide sequence aligned with the FHIT cDNA sequence (cDNA 7F1) and the R11128 nucleotide sequence is shown in FIGS. 7A–7C. As will be noted, neither of the R53187 nor R11128 nucleotide sequences, or any of numerous other EST sequences, span the full FHIT protein coding region. Also, the translations of the R50713, and R11128 sequences in all three reading frames, in both orientations, are shown in FIGS. 8 and 9, respectively, and from none of the translated sequences shown in FIGS. 8 or 9 can the Fhit protein sequence be deduced.

The full length FHIT cDNA probe was then hybridized to northern blots carrying mRNA from a spectrum of tissues. As shown in FIG. 3A, the cDNA detected the ubiquitously expressed 1.1-kb transcript.

Relationship of the cDNA to the genomic map of the region

Oligonucleotide primers from the initially trapped exon were used to generate intron sequences from cosmid 76; these sequences were used in turn to prepare primers and probes to map the exon (E5 in FIG. 1A) on the cosmids, YACs and DNA fro cancer cell lines with deletions, as illustrated in FIG. 1A. Using cDNA as template, oligonucleotide primer pairs bracketing the exons upstream and downstream of exon 5 were then used to amplify cDNA fragments to serve as probes for mapping the 5' and 3' flanking exons on the cosmid contig; these probes demonstrated that the cDNA sequences 5' and 3' of exon 5 were not within the 648D4 cosmid contig covering the homozygous deletions. Thus, cosmid libraries from YACs 850A6, and 750F1, which extend centromeric and telomeric to the fragile region deletions, respectively, as shown in FIG. 1A, were prepared and screened with the 5' and 3' cDNA probes flanking exon 5. Cosmids containing the remaining exons were then used to derive intron sequences using cDNA primers, and the structure of the gene determined as shown in FIG. 1A. T cDNA consisted of 10 exons which were distributed among 3 YAC clones (FIG. 1A); exons 1 through 4 mapped to YAC clone 850A exon 5 was present in all three YAC clones, and exons 6 through 10 mapped to YAC clone 750F1. Only exon 5 fell with the region of homozygous deletion in tumor-derived cell line, i.e. within YAC clone 648D4. The coding region of the ORF began in exon 5 and ended in exon 9, as shown in detail in FIGS. 2A and 2B.

Most interestingly, the first three exons (E1, E2 and E3) of the gene mapped centromeric to the t(3;8) break, between the t(3;8) break and the 5' end of the PTPRG gene, as determined by amplification of these exons from the YAC DNAs and DNAs derived from hybrids carrying portions of chromosome 3, derived from the t(3;8) break and a FRA3B break (data not shown). Thus, this gene became a strong candidate for involvement in initiation of the familial RCCs, because one copy of the gene is disrupted by the translocation.

The homology search in amino acid sequence databases showed a significant homology to a group of proteins which have a histidine triad motif, designated HIT proteins (Seraphin, 1992, J. DNA Sequencing & Mapping 3:177–179). The predicted amino acid sequence of the cDNA for the human gene, designated the Fragile Histidine Triad gene or the FHIT gene, is shown in FIG. 4A compared to the other members of the HIT family. The highest homology of the FHIT protein (~50% identity) is to the yeast diadenosine hydrolases (aph1s), shown in FIG. 4A as PAPH1 and CAPH1, identified in S. pombe and S. cerevisiae, respectively (Huang et al., 1995, Biochem. J. 312:925–932). An alignment of the yeast (S. pombe) Ap4A hydrolase (PAPH1) sequence (U32615) with FHIT (cDNA 7Fl) is shown in FIGS. 10A–10C. There is not extensive homology. When we did a computer search for homology stretches between the yeas hydrolase and the FHIT nucleotide sequences, the result was the small region of nucleotide homology shown in FIG. 10B. The consensus sequence for the HIT family proteins is shown below the amino acid sequences in FIG. 4A.

To recapitulate, the FHIT gene, which may be the human cognate gene for the yeast $Ap_4A$ hydrolase gene, spans a >500 kbp region which includes the t(3;8), the FRA3B and a tumor cell-specific commonly deleted region.

Expression of the FHIT gene

We had placed the BE758–6 locus and microsatellite marker, D3S1300, within the region of common loss in a variety of tumor-derived cell lines and our LOH study of gastric and colon tumors detected a high frequency of allelic deletion, often involving D3S1300, in the region between the t(3;8) and the D3S1234 locus (see FIG. 1A). Now, the localization of both the BE758–6 and D3S1300 loci within the FHIT gene locus, close to the first coding exon, exon 5, suggested that the FHIT gene was the target of deletion in uncultured tumors, as well as tumor-derived cell lines. To begin an analysis of FHIT transcripts in tumor-derived cells, mRNAs from tumor-derived cell lines and normal tissues was studied by northern analysis.

Poly $A^+$RNA from normal tissues and a number of NPC, colon and gastric tumor-derived cell lines, with and without apparent deletions in the fragile region, was tested for hybridization to the FHIT cDNA on northern blots (FIGS. 3A an B).

A low level of expression of the FHIT gene occurred in all human tissues tested, as shown in FIG. 3A for spleen, thymus, prostate, testis, ovary, small intestine, colon and peripheral blood lymphocytes. The major transcript was ~1.1 kb with a longer transcript at 5 kb, which was barely detectable or undetectable on some blots. Since the 1.1 kb transcript matches the size of the full-length cDNA, the longer transcript may represent a precursor RNA which is not fully processed. Similar transcripts were seen in mRNA from brain, heart, lung, liver, skeletal muscle, kidney and pancreas, with the putative unprocessed RNA appearing to be more abundant in lung, small intestine and colon on some northern blots.

mRNAs from tumor-derived cell lines with known homozygous deletions in the fragile region exhibited varying levels of FHIT transcripts (FIG. 3B), from barely detectable (FIG. 3B, lanes 2–4, KatoIII, HKI and LoVo mRNA, respectively) to almost a normal level (lane 8, LS180), relative to normal small intestine mRNA (lane 1).

Note that the NPC cell lines with (CNE2, HK1; FIG. 3B, lanes 5, 3) and without (CNE1; FIG. 3B, lane 6) homozygous deletions we had documented expressed barely detectable FHIT mRNA. The NPC-derived cell line, CNE2, exhibited a possible smaller transcript (FIG. 3B, lane 5), while Colo320, a colorectal carcinoma-derived cell line without a deletion, exhibited an apparently normal-sized FHIT transcript (FIG. 3B, lane 7), although it should be noted that size alone does not imply presence of a wildtype transcript. The ~1.1 kb bands could harbor transcripts with one or more small exons missing, since several exons are very small, e.g. exon 7, 30 nucleotides, exon 2, 49 nucleotides, exon 3, 53 nucleotides. One conclusion of the northern analysis is that there was no direct relationship between size or abundance of transcript and detection of homozygous deletions in specific tumor-derived cell lines, suggesting that there may be small deletions in some tumor cell lines which have not been detected with the available markers.

RT-PCR and cDNA sequence analysis of tumor-derived mRNA

In order to look for abnormalities in FHIT transcripts from deleted and nondeleted tumor cell lines, we reverse-transcribed mRNAs with $(dT)_{17}$ primer, amplified the cDNA with 5' and 3' primers and then reamplified using primers inside the original primers (nested PCR), as described in methods. Positions of the primers are shown in FIG. 2A. The amplified products were separated on agarose gels and normal-sized and aberrant fragments were cut from the gels and sequenced (examples of aberrant bands are shown for mRNAs of uncultured tumors in FIG. 3C; RT-PCR products from the tumor cell lines were very similar). The tumor-derived cell lines exhibited a pattern of products ranging from only one apparently normal-sized amplified transcript to numerous aberrant bands without a normal-sized band. Some tumor-derived cell lines exhibited both an apparently normal-sized and one or more aberrant bands. The sequencing of the aberrant bands revealed numerous abnormal products, some examples of which are illustrated in FIG. 1B. Colon tumor-derived CCL235 and CCL234 cell lines did not show deletion of the STS markers tested, but both showed aberrant transcripts, as illustrated, with CCL235 exhibiting a normal-sized product in addition. HT29 and KatoIII cell lines both showed homozygous deletion, but the KatoIII cell line exhibited a deletion of the telomeric portion of the homozygously deleted region and not the region containing exons 4 and 5, nor the region of exon 6, exons which are all missing in the aberrant RT-PCR product, as illustrated in FIG. 1B. Numerous other tumor-derived cell lines also exhibited aberrant RT-PCR products similar to those shown schematically in FIG. 1B (data not shown). Detailed descriptions of similar aberrant products from uncultured tumors (FIG. 3C) are given in Table 2 and FIG. 2B.

Ten cases of uncultured esophagus, nine of stomach and eight of colon tumors were analyzed, and aberrant transcripts were observed in 5, 5 and 3 cases, respectively (summarized in Tables 2 and 3 and illustrated in FIG. 2B.

TABLE 2

Derivation of FHIT RT-PCR Amplified
Products and cDNA Sequences From
Uncultured Tumors of Gastric Organs

| Origin of Tumors | No. of cases analyzed | Cases with aberrant transcripts | |
|---|---|---|---|
| | | Number of cases | Codes [a] |
| Esophagus | 10 | 5 | E3*, E12*, E13* E32*, E37* |
| Stomach | 9 | 5 | J1*, J3, J4*, J7, J9* |
| Colon | 8 | 3 | 9625*, 5586*, 9575* |

[a] In cases with asterisks (*), normal tissues from the same organs were analyzed and did not exhibit alterations in the coding region sequences.

TABLE 3

Aberrant Transcripts Observed in Uncultured Tumors[1]

| Tumor-derived transcript[2] | | Deletion (position[3]) | Insertion[4] | | | Putative protein[5] coded in frame |
|---|---|---|---|---|---|---|
| | | | Size (bp) | Homology | Effect | |
| *E3 | a | 280–348 | 72 | NS | Ex 8 loss | HIT(−) |
| *E12 | a | 280–348 | — | — | Ex 8 loss | HIT(−) |
| — | b | 122–516 | — | — | FS after EX 6 | HIT(−) |
| *E13 | a | −17–249 | — | — | Ex 5 & 6 loss | — |
| — | b | −17–348 | — | — | Ex 5–8 loss | — |
| E32 | — | 280–449 | — | — | Ex 8 & 9 loss | HIT(−) |
| *E37 | a | — | 72 | NS | none | intact |
| — | b | −73–173 | — | — | Ex 5 loss | HIT(+) |
| *9625 | a | 280–348 | — | — | Ex 8 loss | HIT(−) |
| — | b | −17–279 | 87 | Alu | Ex 5–7 loss | — |
| — | c | −110–204 | — | — | Ex 4 & 5 loss | HIT(+) |
| *5586 | a | −17–349 | 135 | Alu | Ex 5–8 loss | — |
| — | b | −17–279 | 37 | NS | Ex 5–7 loss | — |
| *9575 | a | 280–348 | — | — | Ex 8 loss | HIT(−) |
| — | b | 60–181 | — | — | FS after Ex 5 | HIT(−) |
| — | c | −110–348 | — | — | Ex 4–8 loss | — |
| J1 | a | −110–(−17) | — | — | none | intact |
| — | b | −17–279 | — | — | Ex 5–7 loss | — |
| J3 | — | −17–279 | 173 | Alu | Ex 5–7 loss | HIT(+) |
| J4 | — | −17–457 | 305 | Alu | Ex 5–9 loss | — |

TABLE 3-continued

Aberrant Transcripts Observed in Uncultured Tumors[1]

| Tumor-derived transcript[2] | Deletion (position[3]) | Insertion[4] Size (bp) | Insertion[4] Homology | Effect | Putative protein[5] coded in frame |
|---|---|---|---|---|---|
| *J7 | a  −110–249 | — | — | Ex 4–6 loss | — |
| *J9 | a  280–348 | — | — | Ex 8 loss | HIT(−) |

[1]All the aberrant transcripts which involve the coding sequence of the FHIT gene are shown in Figure 3B. Alu, Alu repeat; FS, frameshift; NS, no significant homology; Ex, exon.
[2]In tumors with asterisks (*), normal transcripts without alteration of coding region sequence were also observed.
[3]The positions of the first and last nucleotides of the deletions are shown according to the nucleotide numbers in Figure 2A.
[4]The position of all insertions was downstream of exon 4.
[5]Putative protein coded in frame with the Fhit protein is shown: HIT(+), protein with HIT motif; HIT(−), protein without HIT motif; —, no protein in frame.

The sequence analyses of the aberrant cDNAs revealed absence of various regions between exons 4 and 9 (Table 3 and FIG. 2B), while the RT-PCR and cDNA sequence analyses of normal tissue mRNAs from the same organs did not exhibit any alterations of the coding region sequence (Table 2, E3, E12, E113, E37, J1, J4, J9, 9625, 5586, 9575). In 8 of 13 cases with aberrant transcripts, normal-sized transcripts were also observed (FIG. 3C; E3, E12, E13, E37, 9625, 9575, J7 and J9; E12 and 9575, not shown), while in 5 of 13 cases normal-sized transcripts were not detected (FIG. 3C, J3, J4), or were barely detected (FIG. 3C, E32, 5586, J1). In most of the aberrant transcripts, the beginning and the end of the deleted portions of the transcripts coincided with splice sites (FIG. 2B), suggesting that the cDNA deletions resulted from the loss of genomic regions containing or surrounding the relevant lost FHIT exons. The aberrant transcripts can be classified into two groups (class I and II, FIG. 2B): class I transcripts lack exon 5, which has the initial methionine codon of the FHIT ORF, resulting in the loss of the ORF; class II transcripts have an intact initial methionine codon but do not include exon 8, except for 9575b, which exhibited a frameshift after exon 6. Thus, in all the class II transcripts, the wildtype ORF of exon 8, the histidine triad containing domain, is not present. Moreover, some of the class II transcripts exhibited loss only of exon 8 (FIG. 2B; E3, E12a, 9625a, 9575a, J9a), suggesting that exon 8 was the target of deletion. Since exon 8 encodes the histidine triad motif, it is likely that neither class I nor class II transcripts, constituting the major fraction of aberrant transcripts, can encode a fully functional protein. However, there is an in frame methionine (Met) codon in exon 6 (see FIG. 2B), and in some cases insertions contribute an in frame Met (not shown); thus, the majority of aberrant transcripts could encode partial proteins with or without the HIT domain as indicated in Table 3. Insertions of various lengths, of DNA not derived from the FHIT gene, were observed in some transcripts; insertions were found only downstream of exon 4 (Table 3, 5586a, 5586b, 9625, J3, J4). A minor group of aberrant transcripts retained intact full length ORFs, but were missing exon 4 (Table 3, J1a), or had insertion of 72 bp of DNA sequence in the 5' noncoding region between exon 4 and 5 (Table 3, E37a, and FIG. 1B). It is possible that such insertions affect translation of the ORF.

In order to determine if the wildtype FHIT cDNA and various cDNAs derived from tumor specific transcripts, which retained the entire coding region, could be translated in vitro, several recombinant plasmids were constructed, each containing a FHIT gene downstream from the T7 promoter and lacking the first noncoding exon. The pFHIT1 plasmid carried an aberrant cDNA, missing exon 4, from the CCL234 colon cancer cell line. Plasmid pFHIT2 carried a cDNA from esophageal tumor E37 with an insertion of 72 bp between exon 4 and exon 5. The pFHIT3 plasmid contained the wildtype FHIT gene lacking exon 1. The constructs were used for in vitro translation by rabbit reticulocyte lysate. Analysis of translation products (FIG. 4B) showed the predicted 16.8 kDa protein translated from each cDNA construct.

The FHIT protein

The protein sequence predicted by the FHIT cDNA is very similar (57/109 amino acid identities; 76/109 or 69%, similarities, as calculated by the NCBI BLAST server) to the S. pombe diadenosine 5',5'" $P^1$, $P^4$ tetraphosphate hydrolase, aph1 (Huang et al., 1995, Biochem. J. 312:925–932), as shown in the amino acid alignment in FIG. 4A, where PAPH1 represents the S. pombe sequence.

The S. pombe aph1 enzyme was cloned by purification of the enzyme, amino acid sequencing of the N-terminus and design of primers to amplify a partial cDNA; the full length genomic and a cDNA of 1.2 kbp were then cloned, sequenced and translated (Huang et al., 1995, Biochem. J. 312:925–932). By similar methods, a human hydrolase (APH1) has been cloned, sequenced and translated (Thorne et al., 1995, Biochem. J. 311:717–721) and, surprisingly, does not resemble the S. pombe aph1 gene nor the FHIT gene. Since higher eukaryotes appear to possess a single 16–21 kDa $Ap_4A$ asymmetrical pyrophosphohydrolase (cited in Thorne et al., 1995, Biochem. J. 311:717–721), it is thus not clear if the FHIT gene is a human APH1 enzyme, although it may be a human cognate of the S. pombe aph1 enzyme.

The FHIT gene is also very similar to the S. cerevisiae aph1 gene product (CAPH1 in FIG. 4A) with 40% identity and 62% similarity in the 50 amino acids between 49 and 102 of the FHIT amino acid sequence, and higher similarity in the HIT domain. The other proteins or hypothetical proteins in FIG. 4A are all members of this HIT gene family, a family of proteins present in prokaryotes, yeast and mammals, described by Seraphin, 1992, DNA Sequencing & Mapping 3:177–179. The signature feature of the family is the histidine triad (most commonly HVHVH, amino acids 94–98 of the FHIT protein, FIG. 4A), which for the case of BHIT (FIG. 4A), the bovine inhibitor of protein kinase C (PKCI1) has been shown to be a zinc-binding site (Pearson et al., 1990, J. Biol. Chem. 265:4583–4591; Mozier et al., 1991, FEBS 279:14–18). The Fhit protein product is only 39% similar to the bovine PKCI1 protein over Fhit amino acids 12–100, as calculated by NCBI BLAST. Thus, the FHIT gene is not likely to be the human PKCI1 gene. Functions of the other HIT genes are thus far not known. Furthermore, structural features of family members have not been studied extensively. The PKCI1 protein has a predicted content of 23% α helix and 42% β conformation (31% β sheet and 11% β turn) (Pearson et al., 1990, J. Biol. Chem. 265:4583–4591); the conserved region, including the histidine triad and upstream region were predicted to be mostly random coil alternating with β sheet conformation, with the HIT domain β sheet. This conformation may be preserved in the Fhit protein. Also, the HIT domain consists of basic and hydrophobic amino acids and might be expected to be buried inside the protein, as suggested for the PKCI1 protein (Pearson et al., 1990, J. Biol. Chem. 265:4583–4591).

6.2. DISCUSSION

The meaning of fragile sites for cancer has been a subject of speculation for years and the near coincidence of the chromosomal position of the FRA3B and the t(3;8) translocation at 3p14.2 has been especially intriguing. The FRA3B is constitutive; that is, after treatment of peripheral blood lymphocytes with ~0.4 μM aphidicolin, which interferes with the action of DNA polymerase α, the characteristic gaps in chromosome region 3p14.2 are observed in ~70% of metaphases from all individuals. So the structural basis for the induction of gaps is present in all individuals. It is also known that within the 3p14.2 band, some of the induced gaps represent chromosome breaks, which occur possibly at several sites in the chromatin of an ~200–300 kilobase region (Paradee et al., 1995, Genomics 27:358–361). Thus, the sequences involved in gaps and breaks may occur in more than one site within the fragile region. At other fragile sites such as the folate-sensitive fragile sites on X, FRAXA, FRAXE, FRAXF, the structural basis for the gaps seems to be variable lengths of CCG or CGG triplet repeats and imperfect repeats are more stable than perfect repeats (Chung et al., 1993, Nature Genet. 5:254–258); these fragile sites seem to be single sites of fragility. Perhaps the FRA3B appears to be the most common fragile site because it actually represents a collection of different fragile sites in a small chromosomal region. The specific sequences responsible for the breaks at FRA3B in hybrid cells have not been described but we have observed that many tumor-derived cell lines exhibit apparent discontinuous homozygous deletions. FIG. 5 diagrams the relationship between the various types of chromosome breaks in 3p14.2 and the organization of the FHIT gene relative to the breaks. Note that in FIG. 5, the chromosome breaks and deletions in the KatoIII gastric carcinoma-derived cells leave the coding region intact, but we have observed only aberrant FHIT transcript in this cell line. Thus, inapparent chromosomal abnormalities must account for the lack of normal transcription in KatoIII and other tumor cells; one possibility is that two FHIT alleles are present in KatoIII with hemizygous alterations in the portions of the FHIT genes not homozygously deleted. Another possibility is that alteration near an exon affects splicing. Additionally, some cancer-derived cell lines and uncultured tumors showed transcripts with alterations to noncoding regions of the FHIT transcript. These transcripts were transcribed and translated into full length protein in a coupled system using a reticulocyte lysate for translation (FIG. 4B), but perhaps in the tumor cells from which they were derived, the lack of exon 4 or insertion of new sequences would affect expression of the Fhit protein. Another puzzle, if the FHIT gene acts as a classical suppressor gene with inactivation of both alleles, is the presence of normal-sized transcripts along with aberrant products in the RT-PCR amplification products of tumor-derived cell lines such as CCL235 (colon), A549 (lung) and HeLa (cervical). It is possible that the aberrant transcripts, which in most cases might encode partial Fhit proteins, could interfere with the function of a normal Fhit protein. The normal-sized products from these cell lines have not yet been fully sequenced so it is possible that they do not, in fact, represent normal transcripts. A number of the uncultured tumors also exhibited aberrant and normal-sized products, and sequencing showed that some of these normal-sized products were indeed wildtype products. In these cases, the normal transcripts could have derived from admixed normal cells.

We have not yet observed point mutations within the coding region of any FHIT transcripts, perhaps suggesting that aberrant FHIT genes usually are the result of deletions.

Aphidicolin, which inhibits the action of DNA polymerase α, induces the gaps and breaks observed in the FRA3B region in normal metaphases; thus in the digestive tract tumors and tumor cell lines we have studied, the genomic deletions resulting in aberrant transcription and loss of functional Fhit protein, could have been induced by exposure of these organs to other agents which interfere with DNA replication, such as nicotine, caffeine, possibly alcohol and other known carcinogens. Interestingly, zinc deficiency is associated with a high frequency of esophageal tumors in man (Yang, 1980, Cancer Res. 40:2633–2644) and rat (Fong et al., 1978, J. Natl. Cancer Inst. 61:145–150); zinc deficiency may cause proliferation of the epithelial cells lining the esophagus (Yang et al., 1987, J. Natl. Cancer Inst. 79:1241–1246), so perhaps zinc deficiency mimics loss of the Fhit protein, which may require bound zinc for its function. It is, therefore, interesting that FHIT gene exon 8, carrying the HIT motif, the presumptive zinc binding site, is a target of deletion in numerous digestive tract tumors.

Whether or not this region of 3p14.2 contains repeated CCG or CGG triplets is not yet known, but because there are differences between the rare, inherited folate-sensitive fragile sites which have been characterized, and the common, constitutive, aphidicolin fragile sites, perhaps a different basis for the fragility should be expected. Thus far, we have noted that there are many Alu repeats in the telomeric portion of the fragile region (not shown) and there is a $(TAA)_{15}$ repeat in this same commonly deleted region for which the number of repeats is highly variable. Perhaps other triplet repeats of this type exist in the region. Also in ~9 kilobase pairs of sequenced portions of the cosmid S8 (telomeric portion of the fragile region, see FIG. 1A), several Alu repeats and a LINE element were encountered; the nucleotide content of the sequenced region was 57.4% A and T residues, while the FHIT cDNA nucleotide content was 48% A and T. A high A and T content is characteristic of some characterized origins of DNA replication, especially in yeast and, in fact, although higher eukaryotic origins of replication have not been identified, it has been speculated that Alu repeats may be connected with replication. Another notable feature of the FHIT gene itself is that nearly all the exons end with the sequence AG, the usual sequence for splice acceptor sites. Based on our observation of frequent aberrant splicing in this fragile region, it is tempting to speculate that the region is especially rich in sequences resembling splice acceptor sites.

Interestingly, we have previously observed a homozygous deletion in mouse L cells, which involves several N-terminal exons of the murine Ptprg gene (Wary et al., 1993, Cancer Res. 53:1498–1502), and Pathak et al. (1995, Cancer Genet. Cytogenet. 83:172–173) have shown that mouse colon and mammary tumors as well as melanomas have abnormalities in the proximal region of mouse chromosome 14 where Ptprg (Wary et al., 1993, Cancer Res. 53:1498–1502) and probably Phit loci map.

Studies of FHIT gene RT-PCR products from RNA of numerous cell lines suggested that FHIT gene abnormalities could be important not only in airway and digestive tract tumors such as nasopharyngeal, esophageal, stomach and colorectal carcinomas, but possibly also in ovarian, cervical and lung tumors, osteosarcoma, and some leukemias; also a bladder and breast carcinoma cell line exhibited homozygous deletions in the fragile region (Lisitsyn et al., 1995, Proc. Natl. Acad. Sci. USA 92:151–155; and our data). Thus, uncultured tumors of these types should be tested for FHIT gene abnormalities.

Clear cell RCCs might also be expected to involve FHIT gene aberrations because the FHIT gene is disrupted by the familial RCC translocation break in 3p14.2 and the translocation/FRA3B region is the target of allelic loss in most sporadic clear cell RCCs (Druck et al., 1995, Cancer Res. 55:5348–5355). Since the FHIT ORF is contained in exons 5 through 9, translocated to chromosome 8 in the t(3;8) family, it is possible that both alleles could still be expressed in some or all tissues; we have found a few polymorphisms within the ORF but none yet which distinguishes the two allelic FHIT transcripts in the t(3;8) lymphoblastoid cell lines (data not shown). If the FHIT gene disruption is the first "hit" to a suppressor gene in this family, then the second FHIT allele should be altered in the t(3;8) tumors. Since we have not yet detected point mutations in the FHIT gene, the best way to look for alterations of the FHIT gene in t(3;8) RCCs would be to amplify the FHIT reverse transcript, as done for uncultured tumors in this study. We have done this experiment for RNA from two RCC cell lines and two uncultured RCCS, all from sporadic tumors, and have observed normal-sized products, which have not yet been cloned and sequenced. Nor have we yet observed homozygous deletions in RCCs using a subset of STS markers in the fragile region. Nevertheless, it would be surprising if the FHIT gene is not involved in some sporadic RCCs.

Since the FHIT gene is probably ubiquitously expressed, it may not be surprising if it can serve as a tumor suppressor gene for specific tissues of many different organs, apparently predominantly of the digestive tract, or maybe predominantly organs with epithelial cell linings. Another common denominator of the types of tumor exhibiting aberrant FHIT alleles might be that they are predominantly organs directly exposed to environmental carcinogens; some of the types of tumors exhibiting FHIT gene aberrations occur very frequently in restricted regions of the globe, NPC in China, gastric cancer in southeast Asia, and often there are environmental factors at play. A possible role for EBV in promotion of Chinese NPCs might be through viral DNA integration into the FRA3B region, suggested by the previous experiments of Rassool et al. (1992, Am. J. Hum. Genet. 50:1243–1251), showing apparent preferential integration of exogenous DNA into induced fragile sites in cultured cells. Similarly human papillomaviruses associated with cervical carcinomas might promote induction of the FRA3B, contributing to the loss of heterozygosity on 3p in uterine cancers (Yokota et al., 1989, Cancer Res. 49:3598–3601), and possibly to inactivation of the FHIT gene. Perhaps the t(3;8) family members, carrying one disrupted FHIT gene succumb to kidney tumors rather than colon or esophageal tumors due to specific types of environmental agents to which they are exposed.

We observed strong similarity of the FHIT gene to *S. pombe* and *S. cerevisiae* $Ap_4A$ hydrolases. Specific roles for the diadenosine, $Ap_4A$, have not been defined (Huang et al., 1995, Biochem. J. 312:925–932) and it is not clear that the $Ap_4A$ hydrolase activity is the only or even the major in vivo function of these proteins. Expression of the *S. pombe* aph1 in *S. cerevisiae* did not inhibit growth, but for unknown reasons the *S. pombe* enzyme was not expressed at a high level (Huang et al., 1995, Biochem. J. 312:925–932). Very little is known of the function of the other members of the HIT family. If indeed the FHIT gene is the cognate of the *S. pombe* aph1 gene identified as an $Ap_4A$ hydrolase, then the strong conservation (69% similarity) between the yeast and human gene suggests important functions. Whether the FHIT gene does or does not encode an $Ap_4A$ hydrolase, it is likely that the study of the *S. pombe* and *S. cerevisiae* hydrolase knockouts and other types of mutations will be useful in understanding the functions of the Fhit protein.

There is some suggestion that as an intracellular regulatory molecule, the $AP_4A$ diadenosine may regulate ability of cells to adapt to metabolic stress such as heat, oxidation, and DNA damage; thus deviation from a normal level of $Ap_4A$ may result in inability of cells to adapt to environmental stresses imposed by carcinogens or viruses which cause genetic damage.

6.3. MATERIAL AND METHODS

Tissues and cell lines

Matched normal and cancerous tissues from patients with primary esophageal, colon and stomach carcinomas were obtained immediately after surgery. Tumors were dissected to eliminate normal tissue before preparation of DNA. Many cell lines were obtained from the ATCC. The RC kidney cell lines were kindly provided by E. Lattime.

RNA extraction and reverse transcription Total and poly $A^+$mRNA was extracted from cell lines and tissues using the RNAzol kit (TelTest, Inc., Texas) or the FastTrack Kit (Invitrogen), respectively. To obtain mRNA from tissues, fresh specimens were frozen immediately after excision, and stored at ~85° C. or in liquid nitrogen until extraction of mRNA. RNA was stored as a pellet under ethanol or solubilized in RNAse-free water and kept at ~70° C. Reverse transcription was performed in 30 $\mu$l final volume of 50 mM tris-HCl pH 8.3, 75 mM KCl, 3 mM $MgCl_2$, 10 mM DTT, 2 $\mu$M dNTPs, 500 ng oligo-dT, 600 units MMLV-RT (BRL), 40 units RNasin (Promega), and 2 $\mu$g RNA. This reaction was incubated at 37° C. for 90 min and boiled for 5 min.

DNA sequence analysis cDNA, genomic clones and putative exons were sequenced using primers specific for vector flanking sequences (T3, T7 etc.) and various synthetic oligonucleotides. RT-PCR products were directly sequenced after isolation of bands from low melt agarose and purification by column chromatography (Qiagen, Chatsworth, Calif.). Sequencing of double-stranded plasmids, PCR products and phage or cosmid genomic clones was performed using Taq DyeDeoxy Terminator Cycle Sequencing Kits (Applied Biosystems, Inc. (ABI)); reaction products were electrophoresed and recorded on the 373 or 377 DNA sequencer (ABI). Sequences were analyzed using GCG, BLAST, and GRAIL software.

PCR amplification

The oligonucleotides for generating probes, PCR products and RT-PCR products were designed using the computer program Oligo 4.0 (National Biosciences). For Southern blots, probes were produced by PCR amplification using various FHIT specific primers, as indicated in results. Sequences and positions of some primers are shown in FIG. 2A.

PCR reactions were carried out in 12.5 or 25 µl final volume with 1–100 ng of template, 20–40 ng primers, 10 mM tris-HCl pH 8.3, 50 mM KCl, 0.1 mg/ml gelatin, 15 MM $MgCl_2$, 200–600 mM dNTPs and 0.5–2.5 units Taq polymerase (ABI). The amplifications were performed in a Perkin-Elmer Cetus thermal cycler for 30 cycles of 94° C. for 30 s (for denaturation), 60° C. (varied for specific primer pairs) for 30 s (for annealing), and extending at 72° C. for 30–45 s. The PCR products were visualized in ethidium bromide stained low melting agarose gels. The bands of amplified DNA were excised from gels and purified for labeling or sequencing.

DNA preparation and Southern blot hybridization

Cellular DNAs were isolated and Southern blots prepared using conventional methods. Probes were labeled by random-priming with [$^{32}$P]-dCTP (NEN) and hybridized to membranes in 0.75 M NaCl, 50% formamide at 42° C. overnight. Final washes of membranes were in 0.1× SSC and 0.1% SDS at 65° C. for 30 min.

Hybridized filters were exposed to XAR-2 X-ray film (Kodak) with intensifying screens for times varying from 1 to 72 h.

Identification of YACs

We and others (Boldog et al., 1993, Proc. Natl. Acad. Sci. USA 90:8509–8513; Boldog et al., 1994, Genes Chrom. Cancer 11:216–221; Wilke et al., 1994, Genomics 22:319–326; Michaelis et al., 1995, Cancer Genet. Cytogenet. 81:1–12; Kastury et al., 1996, Genomics, in press) had previously identified the 850A6 clone from the Genethon mega YAC library as containing the D3S1300 and D3S1481 markers (Roche et al., 1994, Hum. Mol. Genet. 3:215). Overlapping YACs were identified by analysis of the Genethon database information.

Identification of region specific STSs

A number of STSs were available from our work with the 850A6 YAC. The A6URA marker was from the 850A6 URA end, A3 as from an Alu-vectorette amplified fragment of 850A6; BE758–6 and D3S1480 amplified fragments were used as probes to select phage genomic clones from which end sequences were obtained and sequence tagged. A phage genomic clone for D3S1300 was selected from the 850A6 phage library and end clone D1300E3 isolated. Other D3S and WI marker primer pairs were obtained from Research Genetics or were synthesized from sequences provided in the WI database. From sequencing of a phage genomic subclone from the 648D4 YAC, a $(TAA)_{15}$ trinucleotide repeat was found and designated locus ph13; the AP4/5 STS was derived from partial sequencing of a cosmid subclone of the 648D4 YAC.

Cosmid mapping

High molecular weight YAC containing yeast DNA in agarose plugs was partially restricted with the Sau3AI enzyme, and subcloned into a cosmid vector. This cosmid library was initially screened with DNA probes derived from STSs previously mapped to this region. The ends of the insert DNAs flanking the cosmid vector were sequenced to find new STSs, which were used as probes to rescreen the cosmid libraries.

Exon trapping and cDNA cloning

The cosmid DNAs were partially restricted with Sau3AI enzyme, run on a 1.0% agarose gel, and fragments larger than 2 kbp cut out and subcloned into the pSPL vector and transfected into COS-7 cells, according to the manufacturer's instructions. The DNA inserts trapped between the splice sites of the vector were sequenced by a primer supplied with the vector (GIBCO/BRL). The cDNA was extended in the 5' direction by PCR-amplification of a total human fetal brain cDNA using an exon-specific primer (X8, nucleotide numbers −19 to −41) and a RACE reaction kit (Clontech). The normal colon cDNA library was purchased from Clontech.

FHIT exon mapping

The genomic sequences of exon-intron junctions of the FHIT gene were determined by sequencing the positive cosmids with primers derived from the cDNA. Localization of each exon of the FHIT gene was determined by PCR amplification using primers derived from each exon with YAC and chromosome 3 hybrid DNAs as templates. The primer sequences used to obtain cDNA probes flanking exon 5 were: 5'TCTGCTCTGTCCGGTCACA3' (SEQ ID NO:70) (nuc. #−355 to −337) with primer X8 (shown in FIG. 2A) for 5' flanking exons; 5'ATGTCCTTGTGTGC-CCGCT3' (SEQ ID NO:71) (nuc. #105 to 123) with 3D2 (see FIG. 2A) for 3' flanking exons.

Northern blot and hybridization

Two µg of mRNAs were electrophoresed through 1.5% agarose gel in 2.2 M formaldehyde and 1×MOPS buffer and blotted to a positively charged membrane by standard procedures. Northern blot filters of multiple normal tissue mRNAs were purchased (Clontech, Palo Alto, Calif.). The FHIT cDNA probe for hybridization was obtained using the FHIT cDNA as template for PCR-amplification with the following primer pair: 5'TGAGGACATGTCGTTCA-GATTGG3' (SEQ ID NO:72), nuc. #−7 to 17; and 5' CTGTGTCACTGAAAGTAGACC3' (SEQ ID NO:73), nuc. #449 to 429. Probes were labeled by random-priming with [$^{32}$P]-dCTP and 2×106 cpm/ml was hybridized to each filter. Hybridizations were at 42° C. for 16 hours in SSPE buffer (5× SSPE, 10× Denhardt's solution, 0.1 mg/ml carrier DNA, 50% formamide, 2% SDS). Final washes were in 0.lx SSC, 0.1% SDS at 50° C for 30 min before exposure at −80° C. to XAR-2 films (Kodak) with intensifying screens on both sides.

Nested RT-PCR and sequencing of cDNAs

First strand cDNAs were synthesized and 1 µl of each product was subjected to a first round of PCR amplification with 30 cycles of 95° C. for 20 sec, 60° C. for 30 sec, and 72° C. for 1 min with 5% dimethylsulfoxide and 0.5 mM spermidine in 10 µl reaction volume under standard conditions, using primers 5U2 and 3D2, indicated in FIG. 2A. One µl of the reaction products, after 20-fold dilution, was subjected to a second round of PCR amplification using nested primers 5U1 and 3D1 (shown in FIG. 2A), under the conditions noted above, except the reaction volume was 30 µl. The PCR products were run on 1.5% agarose gels, stained with ethidium bromide, purified and 2.5 ng sequenced using the 5U1 primer.

In vitro transcription and translation

Three different fragments of DNA, containing the FHIT gene were obtained by PCR, using oligonucleotides UR5 (5'CTGTAAAGGTCCGTAGTG3' (SEQ ID NO:74), nuc. #−171 to −154 in FIG. 2A) and 06 (5'CTGTGTCACTGAAAGTAGACC3' (SEQ ID NO:75), the reverse complement of nuc. #429–449). Amplifications were performed in 100µl final volume of 10 mM Tris-HCl (pH 8.9), 50 mM KCl, 1.5 mM $MgCl_2$, 200 µM deoxynucleotide triphosphates, 10 ng RT-PCR products and 2.5 U Taq polymerase using an Omni Gene Thermal Cycler. 25 PCR cycles consisted of 94° C. 1 min, 52° C. 1 min and an extension step at 72° C. 45 sec. PCR products were separately inserted in a PCRII plasmid using the TA cloning system (Invitrogen). Recombinant vectors, containing the normal FHIT and aberrant genes under the control of the T7 promoter, were sequenced and used for in vitro transcription and translation.

The in vitro transcription and translation reactions were performed by TnT Coupled reticulocyte systems (Promega) in a final volume of 50 μl containing ½volume rabbit reticulocyte lysate, 1 μg recombinant plasmid DNA, 10 U T7 polymerase, 20 μM amino acid mixture without methionine, 40 μM $^{35}$S-methionine (Amersham) and 40 U RNasin ribonuclease inhibitor. Reactions were carried out for 90 min at 30° C. The synthesized proteins were analyzed by SDS polyacrylamide gel electrophoresis (SDS-PAGE) and autoradiography.

7. DEPOSIT OF MICROORGANISMS

E. coli strain DH5α carrying plasmid p7F1, containing a full-length FHIT cDNA as a BamHI-XbaI insert into the pBluescript SK$^+$vector (Stratagene) was deposited on Jan. 30, 1996, with the American Type Culture Collection, 1201 Parklawn Drive, Rockville, Md. 20852, under the provisions of the Budapest Treaty on the International Recognition of the Deposit of Microorganisms for the Purposes of Patent Procedures, and assigned accession number 69977.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method of diagnosing or screening for the presence a predisposition for developing a cancer in a subject comprising measuring the level of Fhit protein in a sample derived from the subject, in which a decrease in the level of Fhit protein in the sample, relative to the level of Fhit protein found in an analogous sample from a subject not having the disease or disorder or a standard Fhit protein level in analogous samples from a subject not having the disease or disorder or not having a predisposition developing the disease or disorder, indicates the presence of the disease or disorder or a predisposition for developing the disease or disorder.

2. A method of diagnosing or screening for the presence of or a predisposition for developing a cell in a subject comprising detecting one or more mutations in FHIT DNA or RNA derived from the subject in which the presence of said one or more mutations indicates the presence of the disease or disorder or a predisposition for developing the disease or disorder.

3. The method according to claim 2 in which a mutation in an exon of a FHIT DNA or RNA is detected.

4. The method according to claim 3 in which a mutation in a FHIT DNA or RNA coding sequence is detected.

5. The method according to claim 3 in which the mutation is a deletion of at least a portion of the FHIT coding sequence.

6. The method according to claim 5 in which the mutation is a deletion of at least all or a portion of FHIT exon 5.

7. The method according to claim 3 in which the mutation causes a lack of the wild-type open reading frame of exon 8 in a FHIT RNA in the subject.

8. The method according to claim 3 in which the mutation is detected by detecting the presence of a FHIT RNA of aberrant size or sequence when compared to wild-type FHIT RNA.

9. The method according to claim 8 in which the presence of a FHIT RNA of aberrant size or sequence is detected by a method comprising reverse-transcribing RNA from the subject into cDNA.

10. The method according to claim 9 in which the cDNA is subjected to polymerase chain reaction using oligonucleotide primers adapted to amplify a fragment of wild-type FHIT cDNA comprising FHIT exon 5.

11. The method according to claim 9 in which the cDNA is subjected to polymerase chain reaction using oligonucleotide primers adapted to amplify a fragment of wildtype FHIT cDNA comprising FHIT exon sequences between the 3' terminus of exon 4 and exon 8.

12. The method according to claim 3 in which the subject is a human fetus.

13. The method according to claim 3 in which the subject is a human child or adult.

14. The method according to claim 3 in which the mutation is detected by a method comprising contacting RNA or cDNA made therefrom from the subject with a nucleic acid probe capable of specifically hybridizing to FHIT RNA or cDNA under conditions such that hybridization can occur, and detecting or measuring the amount of any hybridization between the RNA or cDNA and the nucleic acid probe.

15. The method according to claim 4 in which the mutation is detected by a method comprising contacting a sample containing protein from the subject with an anti-Fhit antibody under conditions such that immunospecific binding can occur, and detecting or measuring the amount of any immunospecific binding by the antibody.

16. The method according to claim 4 in which the mutation is detected by a method comprising subjecting FHIT RNA from the subject to in vitro translation.

17. A method of identifying a molecule that specifically binds to a ligand selected from the group consisting of a Fhit protein and a fragment of a Fhit protein that is functionally active, comprising (a) contacting said ligand with a plurality of molecules under conditions conducive to binding between said ligand and the molecules; and (b) identifying a molecule within said plurality that specifically binds to said ligand.

18. A method of monitoring a disease involving cell overproliferation in a subject comprising measuring the amount of FHIT RNA or cDNA in a sample derived from the subject, in which an increase in mutant FHIT RNA or cDNA or a decrease or loss in wild-type FHIT RNA or cDNA relative to that present in a sample derived from the subject at an earlier time, indicates disease progression.

19. A method of detecting a predisposition toward an adverse therapeutic outcome or toward recurrence of a disorder involving cell overproliferation in a subject comprising detecting one or more mutations in a FHIT gene in the subject.

20. A method of diagnosing or screening for the presence of or a predisposition for developing a cancer in a subject comprising measuring the level of FHIT cDNA or RNA in a sample derived from the subject, in which a decrease in the level of FHIT cDNA or RNA in the sample, relative to the level of FHIT cDNA or RNA found in a analogous sample from a subject not having the disease or disorder or a standard FHIT cDNA or RNA level in analogous samples from a subject not having the disease or disorder or not having a predisposition for developing the disease or disorder, indicates the presence of the disease or disorder or a predisposition for developing the disease or disorder.

21. A method of diagnosing or screening for the presence of or a predisposition for developing a cancer in a subject comprising measuring the level of Fhit functional activity in a sample derived from the subject, in which a decrease in the level ot Fhit functional activity in the sample, relative to the level of Fhit functional activity found an analogous sample from a subject not having the disease or disorder or a standard Fhit functional activity level in analogous samples from a subject not having the disease or disorder or not having a predisposition for developing the disease or disorder, indicates the presence of the disease or disorder or a predisposition for developing the disease or disorder.

22. A method of diagnosing or screening for the presence of or a predisposition for developing cancer in a subject comprising detecting one or more mutations in Fhit protein derived from the subject in which the presence of said one or more mutations indicates the presence of the disease or disorder or a predisposition for developing the disease or disorder.

23. A method of identifying a molecule that specifically binds to a ligand that is a nucleic acid encoding a Fhit protein or encoding a Fhit fragment, comprising
   (a) contacting said ligand with a plurality of molecules under conditions conducive to binding between said ligand and the molecules; and
   (b) identifying a molecule within said plurality that specifically binds to said ligand.

24. A method of monitoring a cancer in a subject comprising measuring the amount of Fhit protein in a sample derived from the subject, in which an increase in mutant Fhit protein expression, or a decrease or loss in wild-type Fhit protein relative to that present in a sample derived from the subject at an earlier time, indicates disease progression.

* * * * *